(12) United States Patent
Weber et al.

(10) Patent No.: US 12,139,614 B2
(45) Date of Patent: Nov. 12, 2024

(54) PHOTOACTIVATABLE FLUORESCENT DYES WITH HYDROPHILIC CAGING GROUPS AND THEIR USE

(71) Applicant: Max-Planck-Gesellschaft zur Foerderung der Wissenschaften e. V., Munich (DE)

(72) Inventors: Michael Weber, Goettingen (DE); Stefan W. Hell, Goettingen (DE); Alexey Butkevich, Goettingen (DE)

(73) Assignee: Max-Planck-Gesellschaft zur Foerderung der Wissenschaften e. V., Munich (DE)

( * ) Notice: Subject to any disclaimer, the term of this patent is extended or adjusted under 35 U.S.C. 154(b) by 323 days.

(21) Appl. No.: 17/410,879

(22) Filed: Aug. 24, 2021

(65) Prior Publication Data

US 2022/0064452 A1   Mar. 3, 2022

(30) Foreign Application Priority Data

Aug. 28, 2020   (EP) ..................... 20193361

(51) Int. Cl.
*C09B 11/24* (2006.01)
*C12Q 1/6818* (2018.01)

(52) U.S. Cl.
CPC ............ *C09B 11/24* (2013.01); *C12Q 1/6818* (2013.01)

(58) Field of Classification Search
CPC .............................. C09B 11/24; C12Q 1/6818
See application file for complete search history.

(56) References Cited

U.S. PATENT DOCUMENTS

| 5,635,608 A | 6/1997 | Haugland et al. |
| 2012/0122136 A1 | 5/2012 | Szczepanik et al. |

FOREIGN PATENT DOCUMENTS

| JP | 2017222609 A | 12/2017 |
| JP | 2019196349 A | 11/2019 |

(Continued)

OTHER PUBLICATIONS

Balzarotti et al. (2017). Nanometer resolution imaging and tracking of fluorescent molecules with minimal photon luxes. Science, 355(6325), 606-612.

(Continued)

*Primary Examiner* — Robert J Eom
(74) *Attorney, Agent, or Firm* — CAESAR RIVISE, PC

(57) ABSTRACT

Disclosed are photoactivable fluorescent dye compounds of formula I:

(Continued)

wherein: n=0, 1, 2, 3; X is selected from O, CRR', SiRR' and GeRR', where R and R' represent independently alkyl, cycloalkyl, alkenyl, alkynyl or aryl; Y is H, $SO_3H$ or $SO_3M$, with M being a positively charged counterion, in particular selected from $NH_4^+$ and cations of organic ammonium compounds; $R^1$ is H, $CO_2H$, C(O)NH-linker-$CO_2H$, C(O)O-ligand, C(O)NH-ligand or C(O)NH-linker-ligand; $R^2$ may represent H, unsubstituted or substituted alkyl (including cycloalkyl); $R^3$ and $R^4$ may represent independently H or F; $R^5$ is H, Me, $CO_2H$, C(O)NH-linker-$CO_2H$, C(O)O-ligand, C(O)NH-ligand or C(O)NH-linker-ligand; wherein the ligand moiety at each occurrence represents a reactive group or tag, capable to form a covalent or non-covalent bond or molecular complex with a target chemical entity or substance. Methods of using the compounds in imaging of fixed and living cells are also disclosed.

20 Claims, 5 Drawing Sheets

(56) References Cited

FOREIGN PATENT DOCUMENTS

| | | |
|---|---|---|
| WO | 2006114409 A1 | 11/2006 |
| WO | 2011029459 A1 | 3/2011 |
| WO | 2017201531 A1 | 11/2017 |
| WO | 2018133859 A1 | 7/2018 |

OTHER PUBLICATIONS

Belov et al. (2010). Rhodamines NN: a novel class of caged fluorescent dyes. Angewandte Chemie International Edition, 49(20), 3520-3523.
Belov et al. (2014). Masked rhodamine dyes of five principal colors revealed by photolysis of a 2-diazo-1-indanone caging group: synthesis, photophysics, and light microscopy applications. Chemistry-A European Journal, 20(41), 13162-13173.
Borowiak et al. (2020). Optical manipulation of F-actin with photoswitchable small molecules. Journal of the American Chemical Society, 142(20), 9240-9249.
Bottanelli et al. (2016). Two-colour live-cell nanoscale imaging of intracellular targets. Nature communications, 7 (1), 1-5.
Bucevicius et al. (2019). Rhodamine-Hoechst positional isomers for highly efficient staining of heterochromatin. Chemical science, 10(7), 1962-1970.
Bueckers et al. (2011). Simultaneous multi-lifetime multi-color STED imaging for colocalization analyses. Optics express, 19(4), 3130-3143.
Butkevich et al. (2016). Fluorescent rhodamines and fluorogenic carbopyronines for super-resolution STED microscopy in living cells. Angewandte Chemie International Edition, 55(10), 3290-3294.
Butkevich et al. (2017). Hydroxylated Fluorescent Dyes for Live-Cell Labeling: Synthesis, Spectra and Super-Resolution STED. Chemistry (Weinheim an der Bergstrasse, Germany), 23(50), 12114-12119.
Butkevich et al. (2018). Two-color 810 nm STED nanoscopy of living cells with endogenous SNAP-tagged fusion proteins. ACS chemical biology, 13(2), 475-480.
Chen et al. (2012). Second-generation covalent TMP-tag for live cell imaging. Journal of the American Chemical Society, 134(33), 13692-13699.
Gautier et al. (2008). An engineered protein tag for multiprotein labeling in living cells. Chemistry & biology, 15(2), 128-136.
Gee et al. (2001). Caged Q-rhodamine dextran: a new photoactivated fluorescent tracer. Bioorganic & medicinal chemistry letters, 11(16), 2181-2183.
Godin et al. (2014). Super-resolution microscopy approaches for live cell imaging. Biophysical journal, 107(8), 1777-1784.
Grimm et al. (2011). Synthesis of rhodamines from fluoresceins using Pd-catalyzed C-N cross-coupling. Organic etters, 13(24), 6354-6357.
Grimm et al. (2013). Carbofluoresceins and carborhodamines as scaffolds for high-contrast fluorogenic probes. ACS chemical biology, 8(6), 1303-1310.
Grimm et al. (2015). A general method to improve fluorophores for live-cell and single-molecule microscopy. Nature methods, 12(3), 244-250.
Grimm et al. (2016). Bright photoactivatable fluorophores for single-molecule imaging. Nature methods, 13(12), 985-988.
Grimm et al. (2016). Synthesis of a far-red photoactivatable silicon-containing rhodamine for super-resolution microscopy. Angewandte Chemie International Edition, 55(5), 1723-1727.
Grimm et al. (2017). General synthetic method for Si-fluoresceins and Si-rhodamines. ACS central science, 3(9), 975-985.
Hauke et al. (2017). Specific protein labeling with caged fluorophores for dual-color imaging and super-resolution microscopy in living cells. Chemical science, 8(1), 559-566.
Henares et al. (2013). Novel fluorescent probe for highly sensitive bioassay using sequential enzyme-linked immunosorbent assay-capillary isoelectric focusing (ELISA-CIEF). Analyst, 138(11), 3139-3141.
Ji et al. (2017). Photodegradable hydrogels for external manipulation of cellular microenvironments with real-time monitoring. RSC advances, 7(39), 24331-24337.
Juillerat et al. (2003). Directed evolution of O6-alkylguanine-DNA alkyltransferase for efficient labeling of fusion proteins with small molecules in vivo. Chemistry & biology, 10(4), 313-317.
Li et al. (2018). Switchable fluorophores for single-molecule localization microscopy. Chemical reviews, 118(18), 9412-9454.
Los et al. (2008). HaloTag: a novel protein labeling technology for cell imaging and protein analysis. ACS chemical biology, 3(6), 373-382.
Miller et al. (2005). In vivo protein labeling with trimethoprim conjugates: a flexible chemical tag. Nature methods, 2 (4), 255-257.
Nelson et al. (2004). 2-Amino-O 4-benzylpteridine derivatives: potent inactivators of O 6-alkylguanine-DNA alkyltransferase. Journal of medicinal chemistry, 47(15), 3887-3891.
Poc et al. (2020). Interrogating surface versus intracellular transmembrane receptor populations using cell-impermeable SNAP-tag substrates. Chemical science, 11(30), 7871-7883.
Ratz et al. (2015). CRISPR/Cas9-mediated endogenous protein tagging for RESOLFT super-resolution microscopy of iving human cells. Scientific reports, 5(1), 1-6.
Sahl et al. (2017). Fluorescence nanoscopy in cell biology. Nature reviews, Molecular cell biology, 18(11), 685-701.
Sahl et al. (2019). High-resolution 3D light microscopy with STED and RESOLFT. High resolution imaging in microscopy and ophthalmology, 3-32.
Srikun et al. (2010). Organelle-targetable fluorescent probes for imaging hydrogen peroxide in living cells via SNAP-Tag protein labeling. Journal of the American Chemical Society, 132(12), 4455-4465.
Veetil et al. (2017). Cell-targetable DNA nanocapsules for spatiotemporal release of caged bioactive small molecules. Nature nanotechnology, 12(12), 1183-1189.
Wang et al. (2014). The covalent trimethoprim chemical tag facilitates single molecule imaging with organic fluorophores. Biophysical journal, 106(1), 272-278, S1-S3.
Winter et al. (2017). Multicolour nanoscopy of fixed and living cells with a single STED beam and hyperspectral detection. Scientific reports, 7(1), 1-11.
Wysocki et al. (2011). Facile and general synthesis of photoactivatable xanthene dyes. Angewandte Chemie International Edition, 50(47), 11206-11209.

(56) References Cited

OTHER PUBLICATIONS

Ye et al. (2018). Tandem payne/dakin reaction: A new strategy for hydrogen peroxide detection and molecular imaging. Angewandte Chemie, 57, 10173-10177.
English abstract for JP 2017222609 A (2017).
English abstract for JP 2019196349 A (2019).

A

B

C

PHOTOACTIVATABLE FLUORESCENT DYES WITH HYDROPHILIC CAGING GROUPS AND THEIR USE

BACKGROUND OF THE INVENTION

Fluorescent dyes and reactive labels derived therefrom are widely used as indispensable markers in biology, analytical chemistry and optical microscopy. In cell imaging, their brightness, tunable properties and photostability provide an important advantage over genetically encoded fluorescent protein labels. In particular, with the development of fluorescence nanoscopy (superresolution microscopy) techniques, overcoming the Abbe's light diffraction limit by differentiation between the distinct molecular states of the emitters, the development of fluorescent dyes with tightly controlled photophysical properties becomes ever more important.

In most fluorescence nanoscopy techniques, key to achieving the subdiffraction resolution is the precise spatiotemporal control of the dye molecule subpopulations in the emitting and non-emitting states with a dedicated shaped or patterned light beam. This switching beam can either: 1) rapidly force the excited fluorophore molecules back down into the non-emitting ground state ($S_1 \rightarrow S_0$ transition by stimulated emission) immediately post-excitation; 2) induce photochemical isomerization between the geometric isomers of the dye, only one of which undergoes efficient excitation into the emitting $S_1$ state under chosen imaging conditions; or 3) induce a distinct photochemical reaction, irreversibly converting a non-emitting (dark) label molecule into a fluorophore. The latter type of photoactivatable labels are commonly termed caged dyes (in most cases the caging group being a photocleavable protecting group of a suitable type).

Caged dyes represent particularly useful labels for a variety of single molecule localization microscopy (SMLM) methods [Chem. Rev. 2018, 118, 9412-9454], such as photoactivated localization microscopy (PALM), due to minimal fluorescence background and high contrast upon photoactivation. The photons, repeatedly emitted by individual molecules in sparse subsets of photoactivated labels, can be localized from multiple camera readouts followed by photobleaching of the activated molecules. Iterating the photoactivation/localization cycles allows to reconstruct the super-resolved image with down to 10-20 nm precision in the best case scenario. Most importantly, the recently developed minimal photon fluxes (MINFLUX) technique [e.g. Balzarotti et al., Science 2017, 355, 606-612], combining single fluorescent molecules as emitters with position localization derived from the local minimum of a shaped excitation beam, improves the resolution to the theoretical limit corresponding to the molecular size of the fluorophore (1-3 nm for small organic molecules). The fluorescent labels of the present invention are designed to conform to the needs of these techniques.

Another potential application of the caged fluorescent labels of the present invention is their use in stimulated emission depletion (STED) imaging to obtain multicolor images or to add additional features to the acquisition. For the most commonly used triarylmethane fluorophores with small Stokes shifts (20-30 nm in terms of excitation/fluorescence emission wavelength maxima), there exists a limit on the number of imaging color channels attainable with a single depletion laser. This limit depends on the hardware and the software implementation of the STED microscope and, in the literature, two-color imaging was reliably demonstrated with a variety of dye combinations in fixed and living cells using commercial instruments [Bottanelli et al., Nat. Commun. 2016, 7, 10778; Bucevičius et al., Chem. Sci. 2019, 10, 1962]. With additional signal processing based on differences in the fluorescence lifetimes of the labels [Bückers et al., Optics Express 2011, 19(4), 3130-3143] or their emission spectra differences [Winter et al., Sci. Rep. 2017, 7, 46492], the number of channels could be increased to three or four for select samples. Application of the caged STED labels of the present invention, together with the STED dyes developed in previous studies, will allow to reduplicate the attainable number of color channels in STED nanoscopy.

Diverse caging strategies have been proposed for the fluorophores used in superresolution imaging applications. In particular, transformation of the lactone ring of the rhodamine fluorophores into the corresponding cyclic α-diazoketones, 1,2,3-thiadiazoles or N-nitroso(thio)amides represents an efficient caging strategy [Belov et al., Angew. Chem. Int. Ed. 2010, 49, 3520-3523; Hell et al., WO2011/029459A1]. The most widely accepted α-diazoketone-caged dyes (named rhodamines NN) undergo photoinduced Wolff rearrangement upon irradiation with 360-420 nm light, converting into the fluorescent 2'-carboxymethyl- or 2'-methylrosamine products. This strategy has been extended to a variety of substituted diazoketone-caged rhodamines [Belov et al., Chem. Eur. J. 2014, 20, 13162-13173], carbo- and Si-rhodamines [Grimm et al., Nat. Methods 2016, 13(12), 985-988; Lavis et al., WO2017/201531A1]. The significant drawback of the diazoketone-caged dyes is the varying efficiency of the photoactivation depending on the substitution pattern of the caged triarylmethane fluorophore due to the concomitant formation of non-fluorescent byproducts. While the diazoketone labels have been successfully employed in SMLM techniques, including live-cell imaging, their application in STED nanoscopy has been limited by the two-photon uncaging with the high intensity 775 nm depletion laser beam [Belov et al., Chem. Eur. J. 2014, 20, 13162-13173].

Another well-established caging strategy applicable to triarylmethane fluorophores relies on the installation of photocleavable carbamate protecting groups onto the amino groups of the unsubstituted or N,N'-disubstituted rhodamines (N,N,N',N'-tetrasubstituted rhodamine dyes, such as TMR or SiR, cannot be caged using this approach) [Grimm et al., Org. Lett. 2011, 13(24), 6354-6357; Wysocki et al., Angew. Chem. Int. Ed. 2011, 50, 11206-11209; Grimm et al., ACS Chem. Biol. 2013, 8, 1303-1310; Grimm et al., Angew. Chem. Int. Ed. 2016, 55, 1723-1727]. The most commonly used photolabile N-protecting groups were of 4,5-dialkoxy-2-nitrobenzyloxycarbonyl type, in particular nitroveratryloxycarbonyl (NVOC), easily cleavable upon irradiation with 405 nm light. Similarly, fluorescein dyes have been protected as O,O'-bis(2-nitrobenzyl) ethers [Hauke et al., Chem. Sci., 2017, 8, 559-566]. Introduction of these benzyl ethers and benzyl carbamate protecting groups adds significantly to the bulkiness and hydrophobicity of the caged fluorescent label, potentially leading to technical problems related to aggregation and precipitation of labeled antibodies, loss of selectivity or affinity with self-labeling tag proteins. Beside the imaging applications, the photocleavable carbamate-protected rhodamines have been employed as fluorogenic enzyme substrates [Henares et al., Analyst 2013, 138, 3139-3141], chemosensors [Ye et al., Angew. Chem. Int. Ed. 2018, 57, 10173-10177], photoactivatable fluorescent tracers [Gee et al., Bioorg. Med. Chem. Lett. 2001, 2181-2183] or as fluorescent indicators of the covalently attached targeted payload release [Veetil et al., Nature Nanotech. 2017, 12, 1183-1189]. Some improvement of the aqueous solubility, photolysis rate and quantum yields of the 2-nitrobenzyl carbamate-protected rhodamine dyes has been achieved with the introduction of the carboxylate group in α-position of the 2-nitrobenzyl group [Haugland et al., U.S. Pat. No. 5,635,608].

In view of this prior art, the main object underlying the present invention is the provision of new photoactivatable fluorescent dyes and labels with favorable properties which overcome or alleviate the above outlined drawbacks of the fluorescent dyes and labels of the prior art.

This object has been achieved according to the present invention by providing the photoactivatable dyes of the invention and the use thereof. Other aspects and more specific embodiments of the invention are described below.

DESCRIPTION OF THE INVENTION

The novel compounds of the invention are photoactivatable triarylmethane fluorescent dyes having their amino groups protected in the form of 2-nitrobenzyl carbamates, appropriately substituted on the benzyl ring to tune to the desired photoactivation/deprotection wavelength and impart the necessary hydrophilic properties. The novel compounds of the invention have the general structural formula I below:

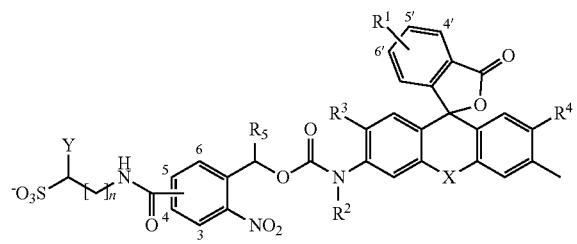

wherein:
n=0, 1, 2, 3;
X is selected from O, CRR', SiRR' and GeRR', where R and R' represent independently alkyl, cycloalkyl, alkenyl, alkynyl or aryl;
Y is H, $SO_3H$ or $SO_3M$, with M being a positively charged counterion, in particular selected from $NH_4^+$ and cations of organic ammonium compounds;
$R^1$ is H, $CO_2H$, C(O)NH-linker-$CO_2H$, C(O)O-ligand, C(O)NH-ligand or C(O)NH-linker-ligand
$R^2$ may represent H, unsubstituted or substituted alkyl (including cycloalkyl);
$R^3$ and $R^4$ may represent independently H or F;
$R^5$ is H, Me, $CO_2H$, C(O)NH-linker-$CO_2H$, C(O)O-ligand, C(O)NH-ligand or C(O)NH-linker-ligand;

wherein the ligand moiety at each occurrence represents a reactive group or tag, capable to form a covalent or non-covalent bond or molecular complex with a target chemical entity or substance; and wherein

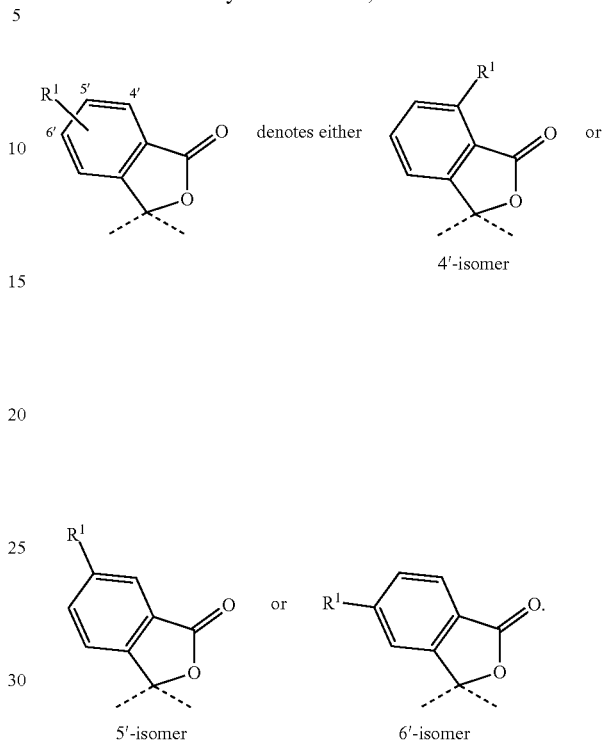

More specifically, the ligand moiety may comprise or represent a reactive group which is selected from an activated ester, in particular a N-hydroxysuccinimidyl or pentafluorophenyl ester, an activated carbonate, in particular N-hydroxysuccinimidyl carbonate, an amine, a thiol, an azide, an alkene or alkyne, including a bicyclic and/or strained alkene or alkyne, a maleimide, a tetrazine group, or a ligand which is selected from the group comprising a HaloTag ligand, a SNAP-Tag ligand, a CLIP-Tag ligand, a TMPTag ligand, or a ligand for a protein which is a functional analog of these protein tags, biotin, a taxoid moiety, in particular paclitaxel, docetaxel, cabazitaxel, larotaxel or a structurally related compound, phalloidin, jasplakinolide and other high-affinity ligands.

The linker moiety may be any chemical group capable to connect two parts of a molecule through covalent bonds. More specifically, the linker group may be for example an alkyl (polymethylene) chain —$(CH_2)_n$—, where n=1-20, a disubstituted cycloalkyl such as trans-1,4-cyclohexanediyl, a polyglycine chain of type —$(NHCH_2C(=O))_n$—, where n=1-10, a glycine-serine peptide linker of type $(GS)_n$, $(GGS)_n$, $(GGGS)_n$ or $(GGGGS)_n$, where n=1-10, or a PEG chain of type —$(CH_2CH_2O)_n$— or —$(CH_2CH_2O)_{n-1}$—$CH_2CH_2$—, where n=1-100.

More specific embodiments of compounds of the present invention are the photoactivatable (caged) dyes of the general structural formula I belonging to the classes of rhodamine dyes (Ia; X=O), carborhodamine dyes (Ib; X=CRR'), silicorhodamine dyes (Ic; X=SiRR'), germanorhodamine dyes (Id; X=GeRR') bearing the hydrophilic carbamate caging groups:

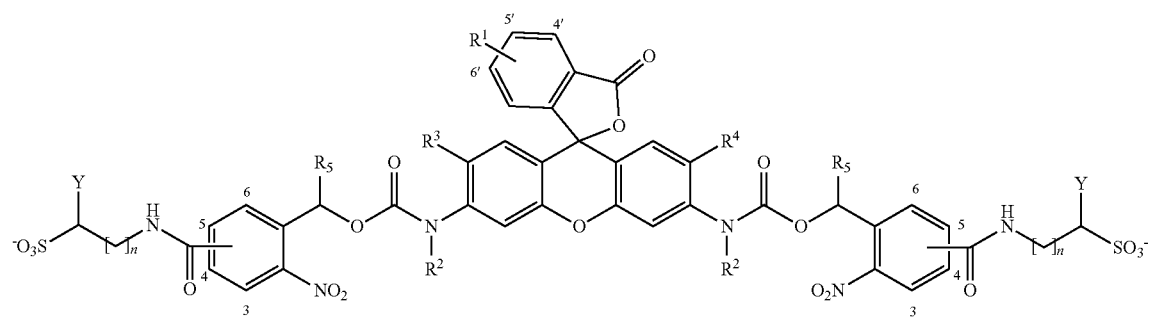
Ia
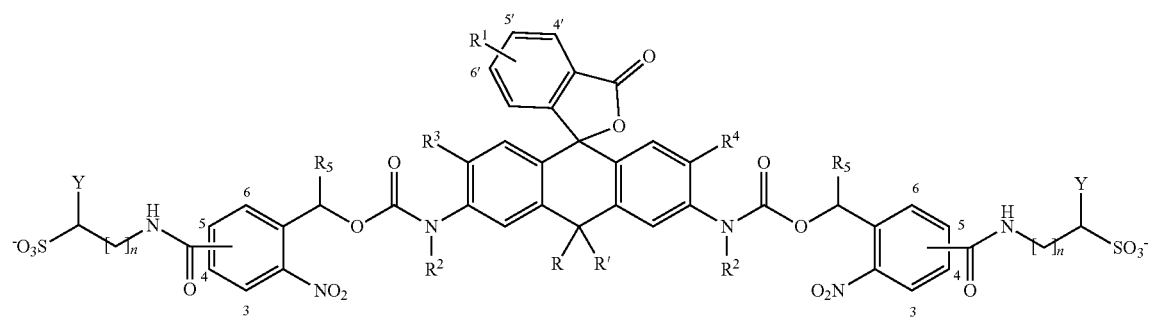
Ib
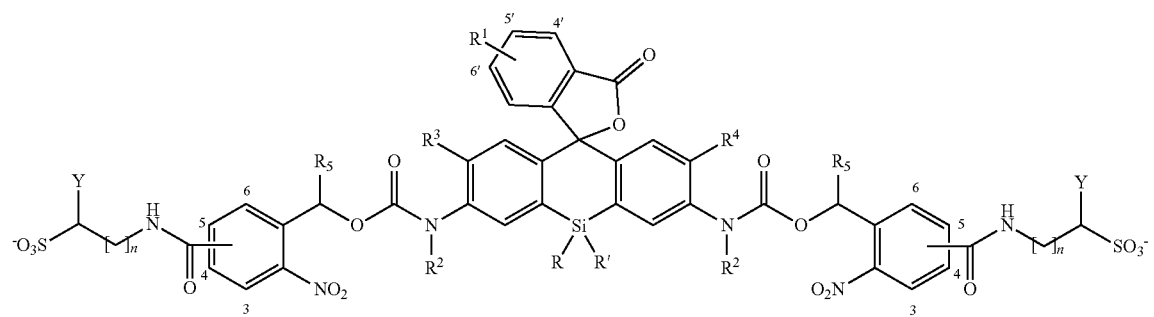
Ic
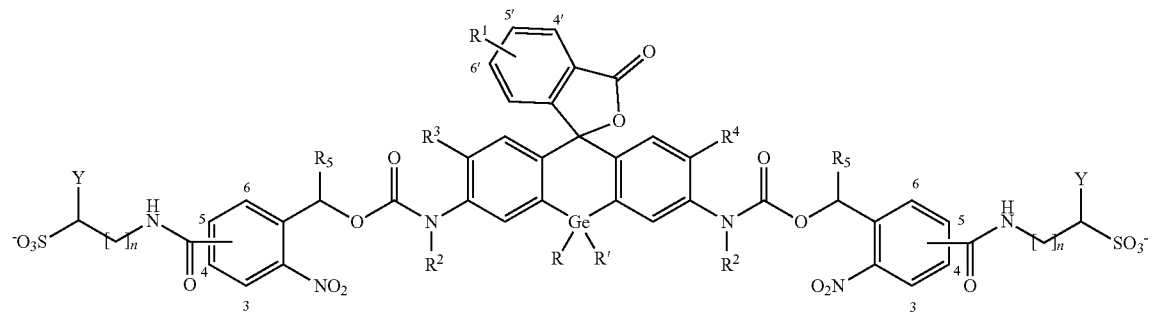
Id
wherein n, Y, R¹, R², R³, R⁴, R₅, R, R' are defined as above.

Even more specific embodiments of the compounds represented by formula I have a structural formula selected from:
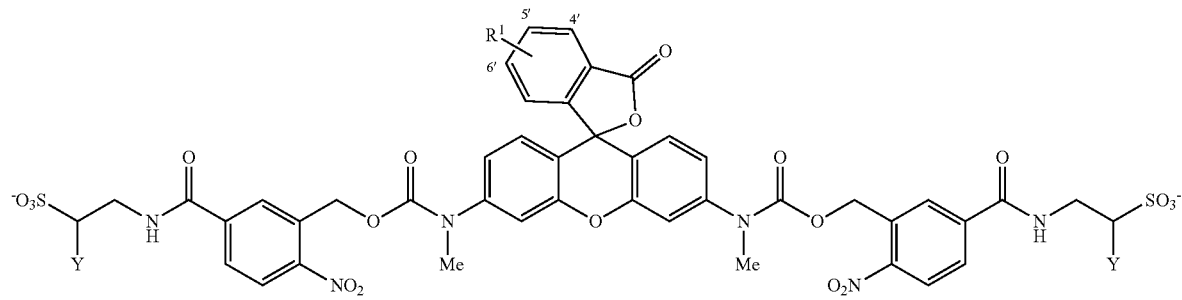
IIa
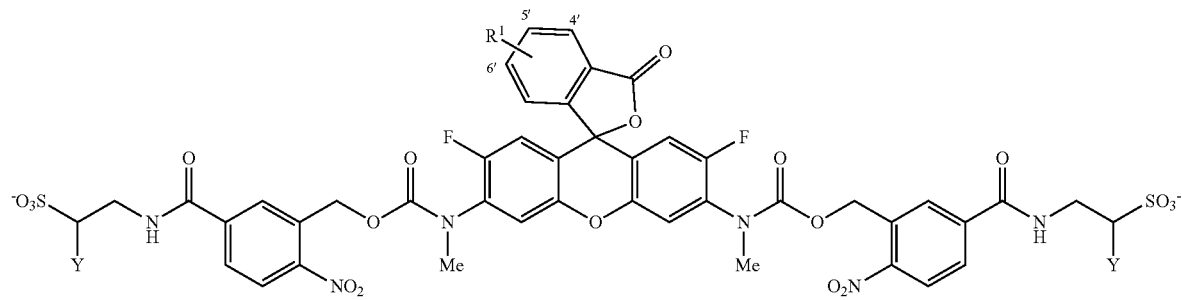
IIb
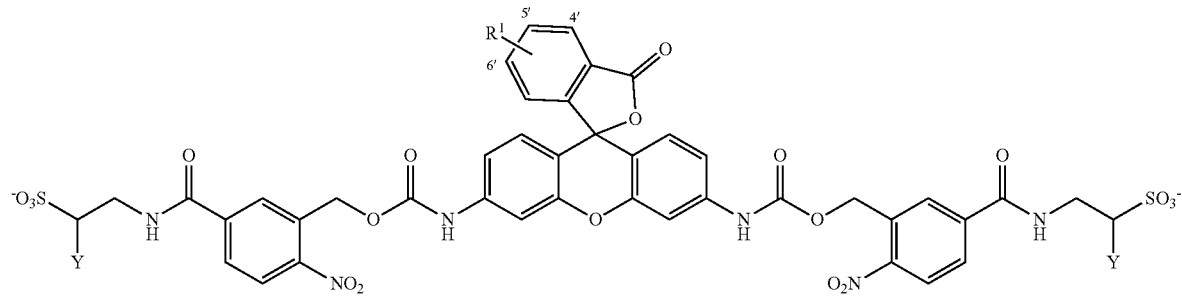
IIc
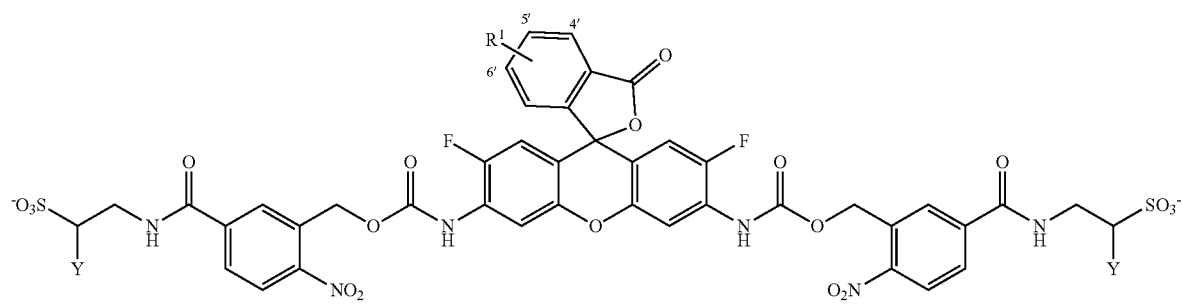
IId -continued
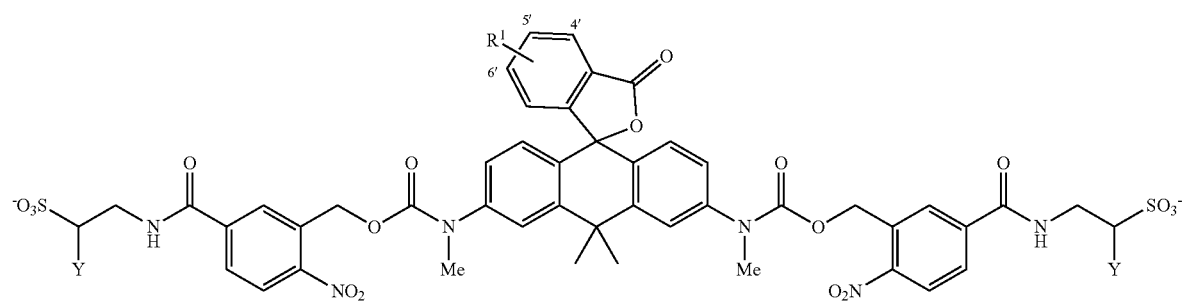
IIe
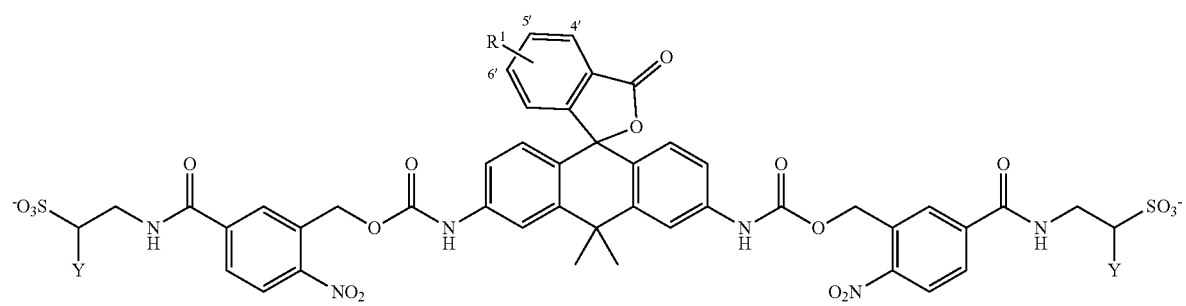
IIf
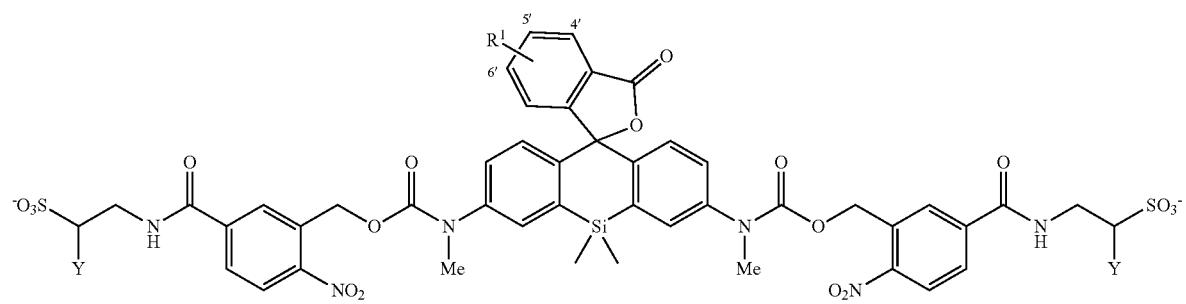
IIg
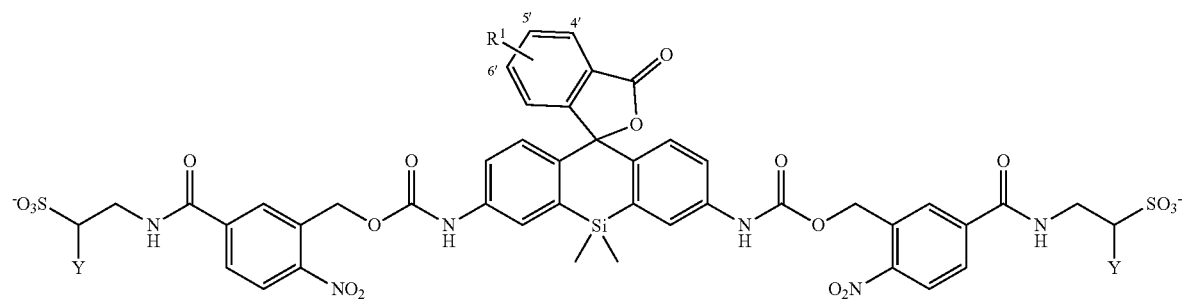
IIh
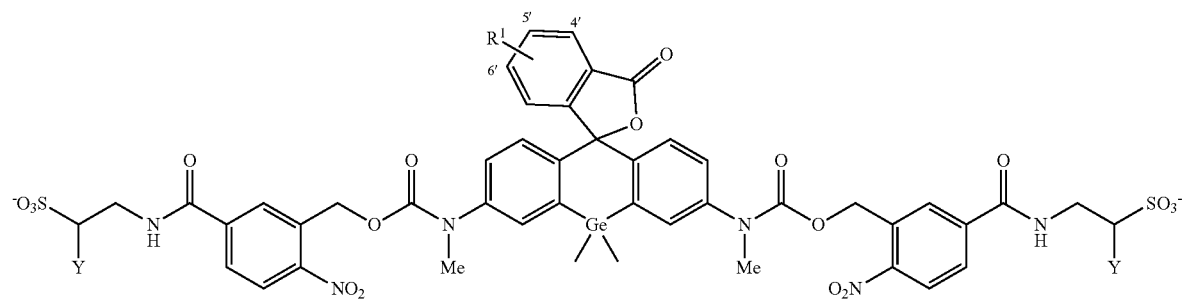
IIi

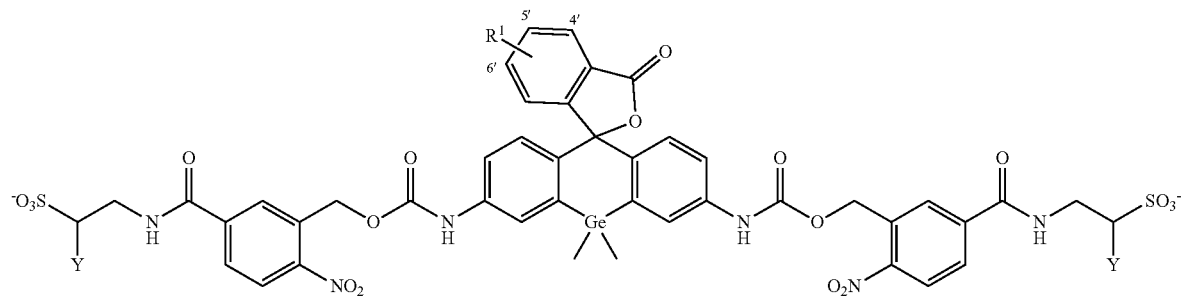

IIj wherein Y and R¹ are defined as above.

In further more specific embodiments of the compounds represented by any one of formulae IIa-j, R¹ represents a substituent group C(O)—Z and Z may represent OH, NH-linker-CO₂H, O-ligand, NH-ligand or NH-linker-ligand as defined above. These compounds wherein R¹ represents a substituent group C(O)—Z in any one of formulae IIa-j are referred herein to as compounds of the corresponding formulae IIIa-IIIj and may be a 4'-isomer, a 5'-isomer or a 6'-isomer of a compound of formulae IIIa-IIIj as represented by one of the following formulae 4'-IIIa-IIIj, 5'-IIIa-IIIj or 6'-IIIa-IIIj:

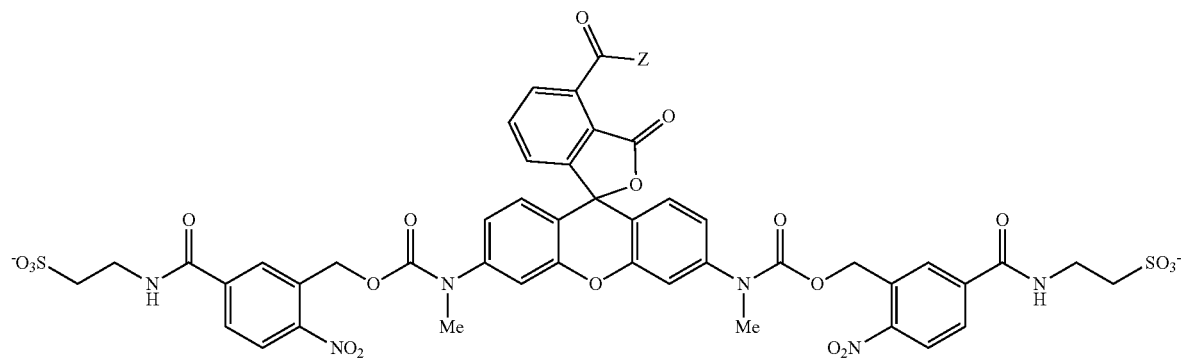

4'-IIIa

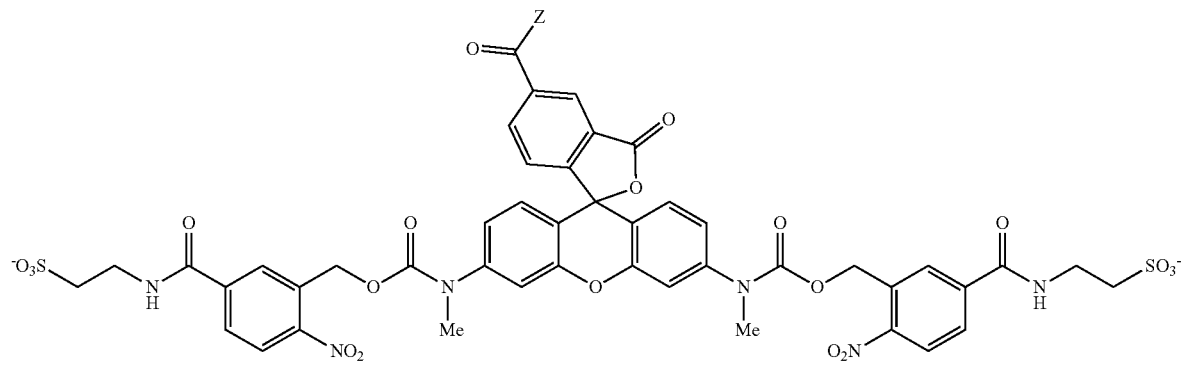

5'-IIIa

6'-IIIa
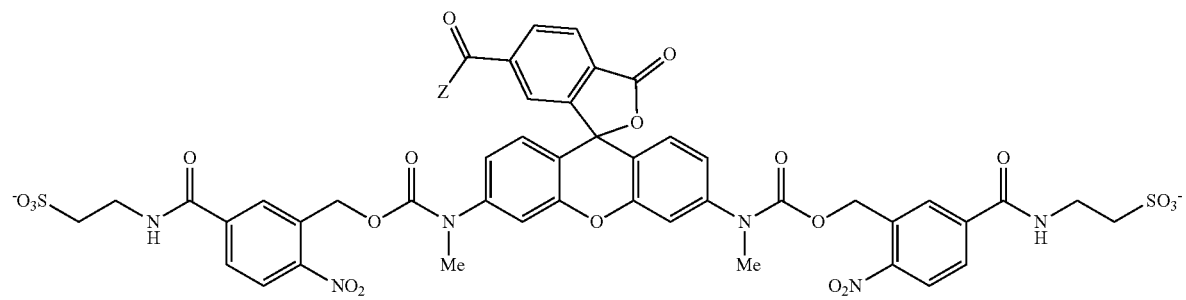
4'-IIIb
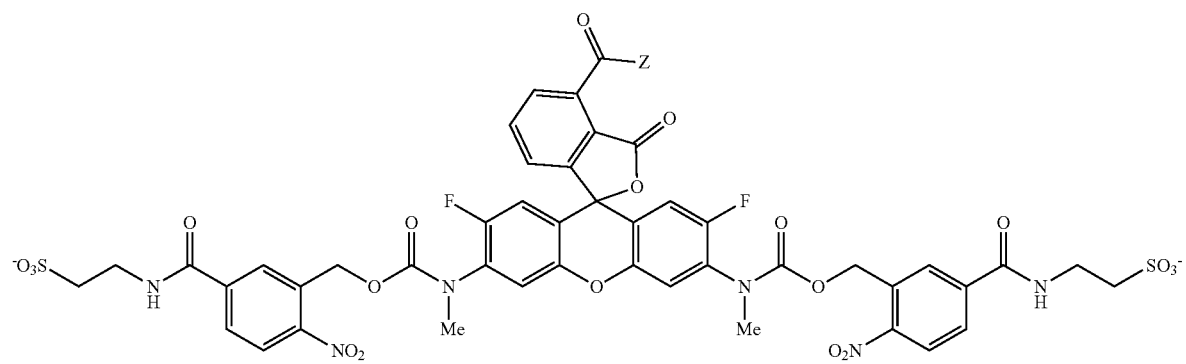
5'-IIIb
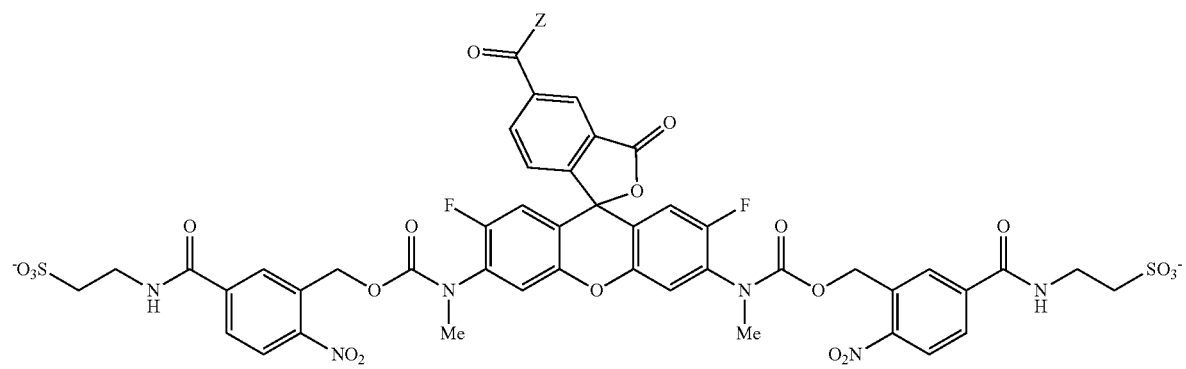
6'-IIIb
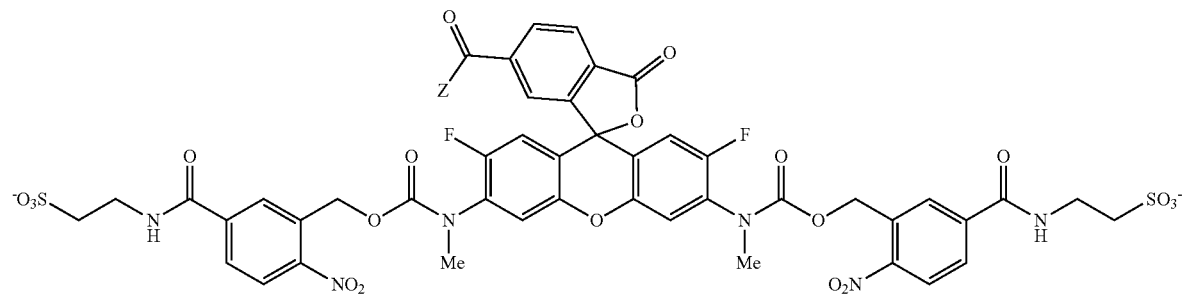

4'-IIIc
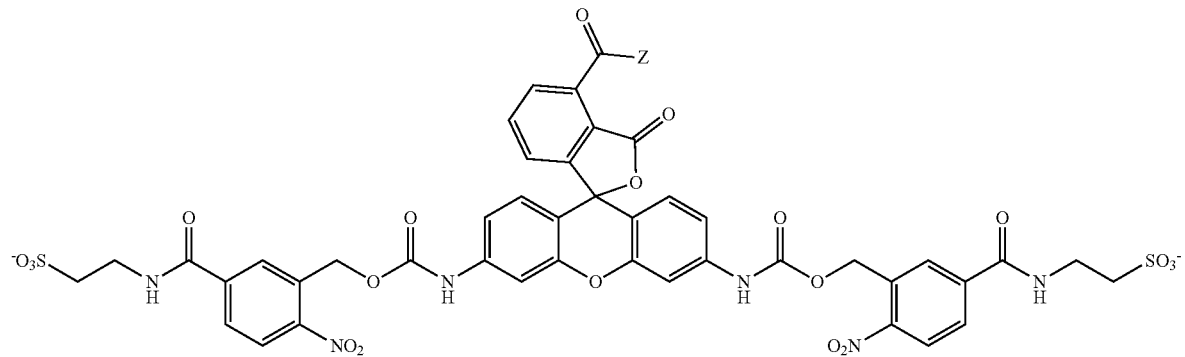
5'-IIIc
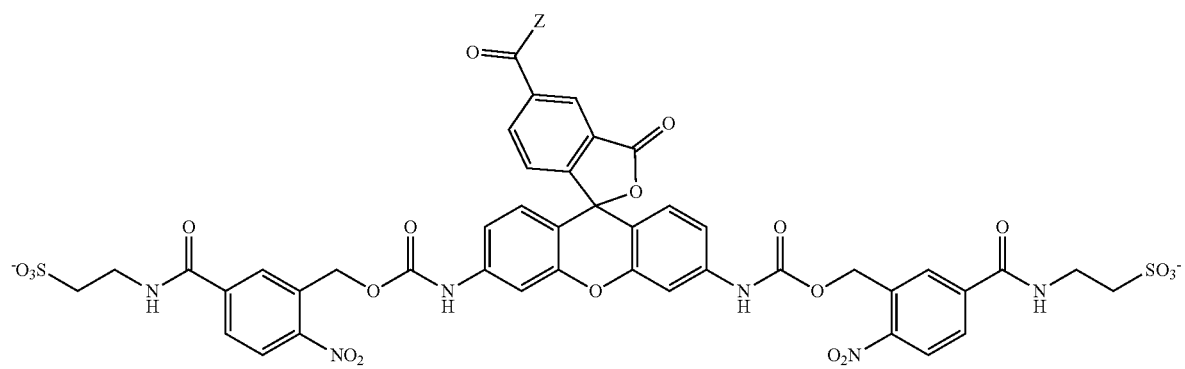
6'-IIIc
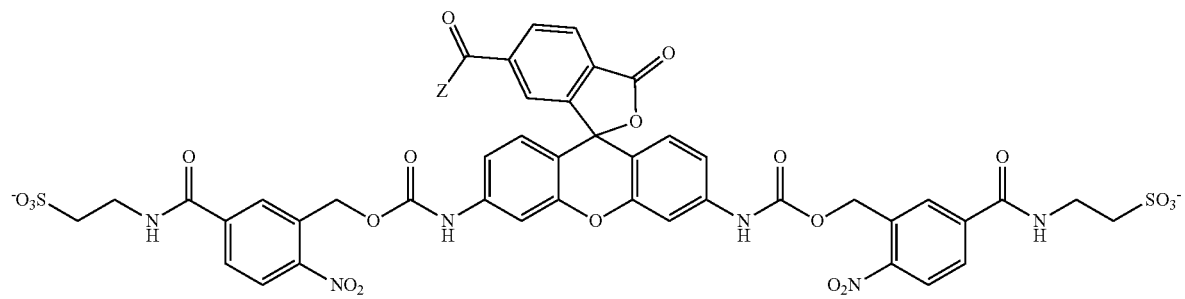
4'-IIId
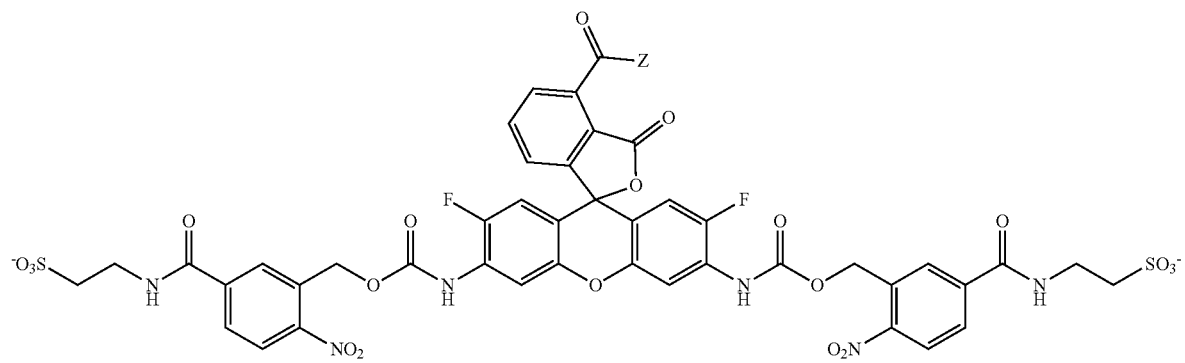

5'-IIId
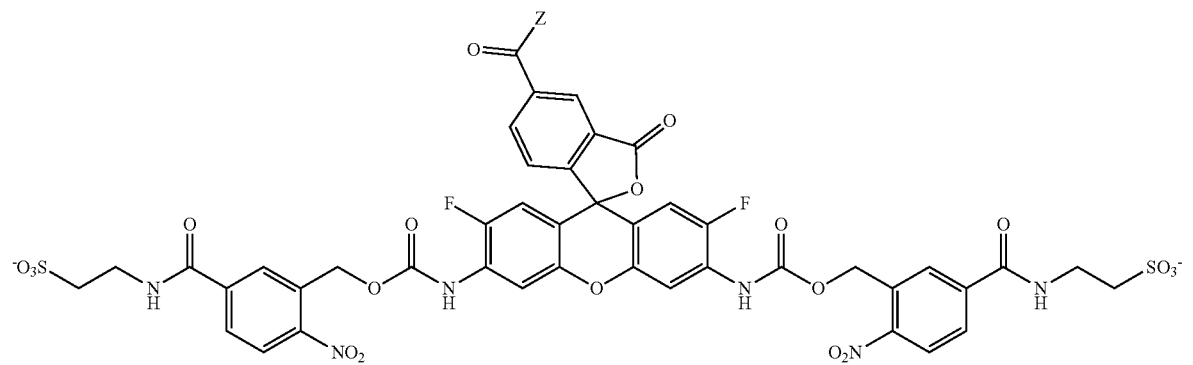
6'-IIId
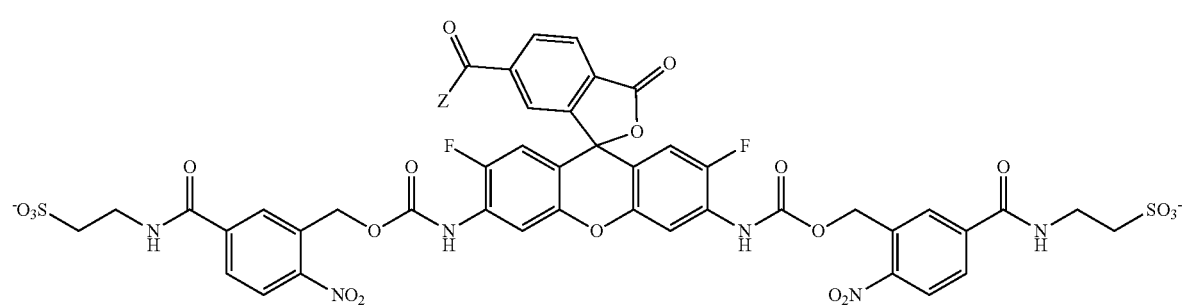
4'-IIIe
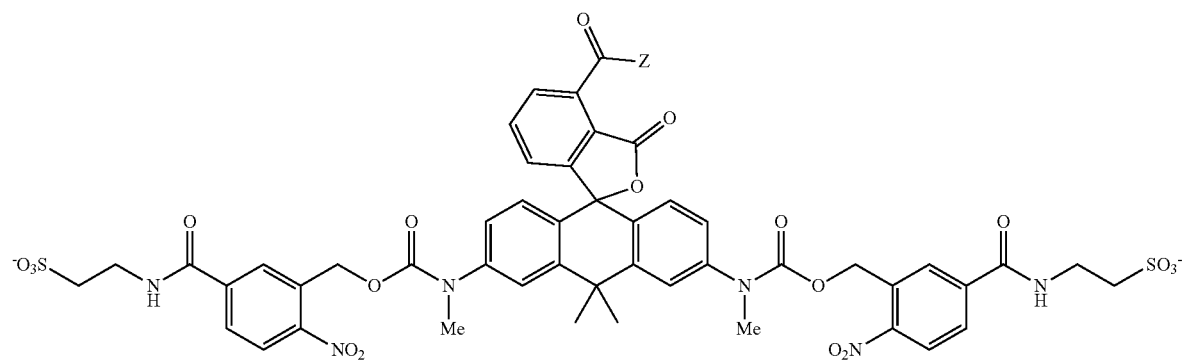
5'-IIIe
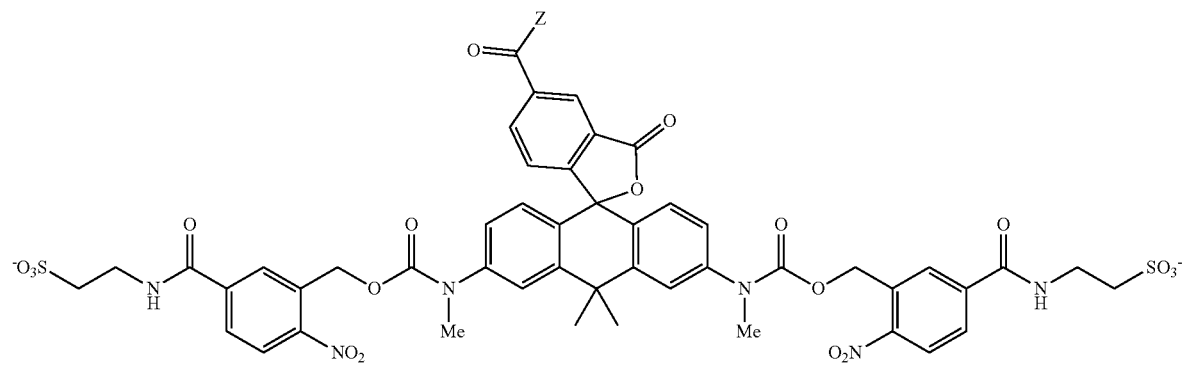

-continued
6'-IIIe
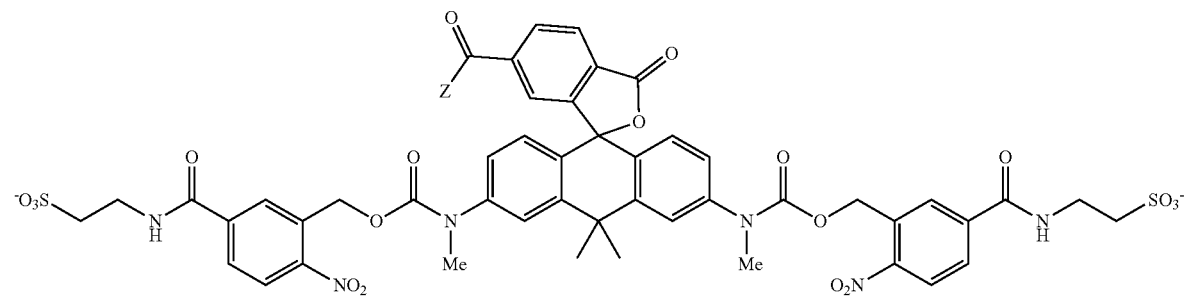
4'-IIIf
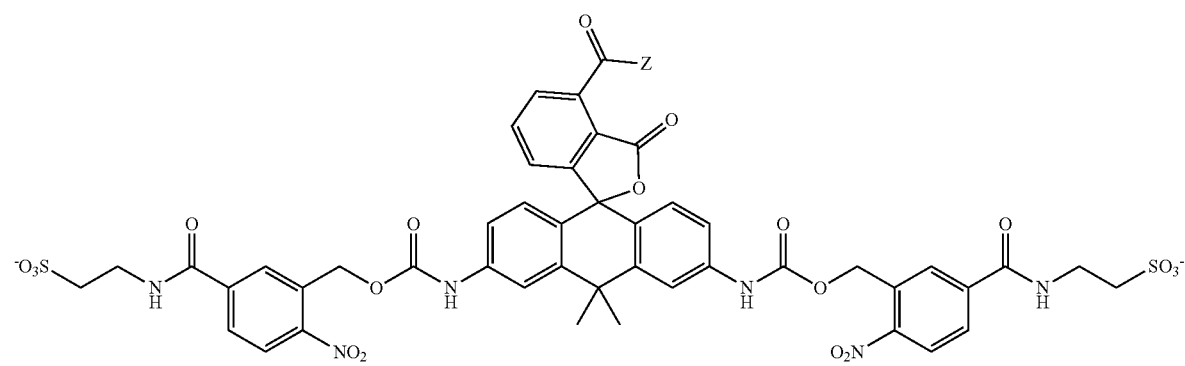
5'-IIIf
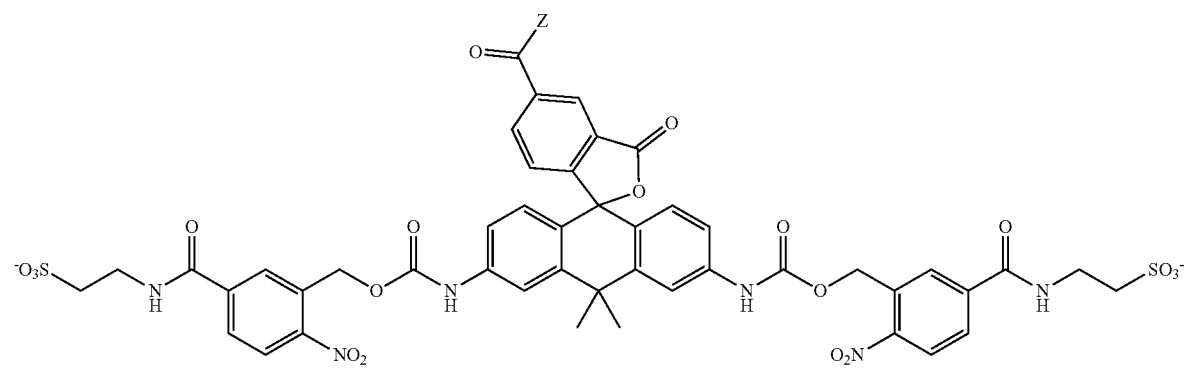
6'-IIIf
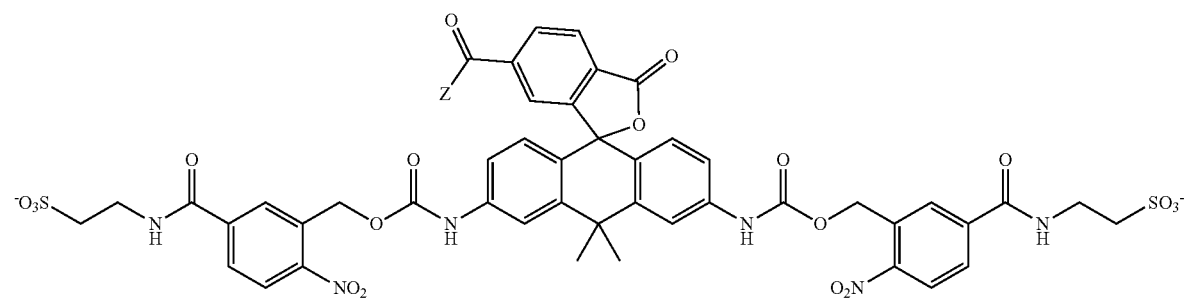

-continued
4'-IIIg
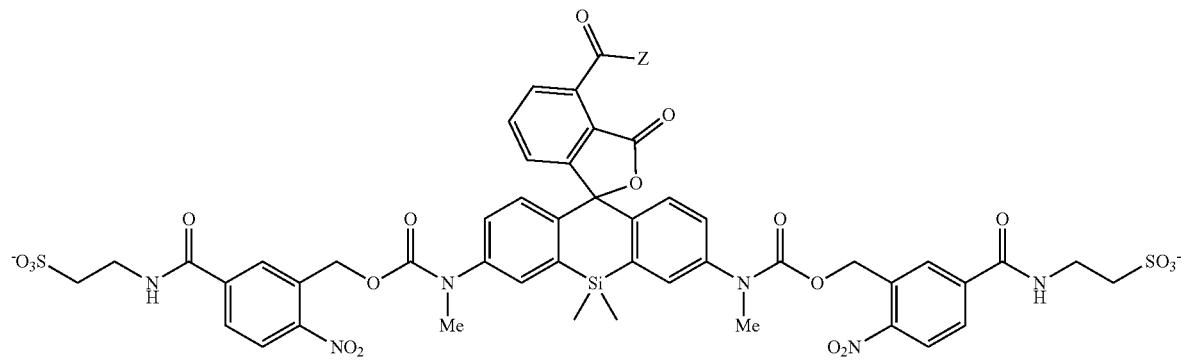
5'-IIIg
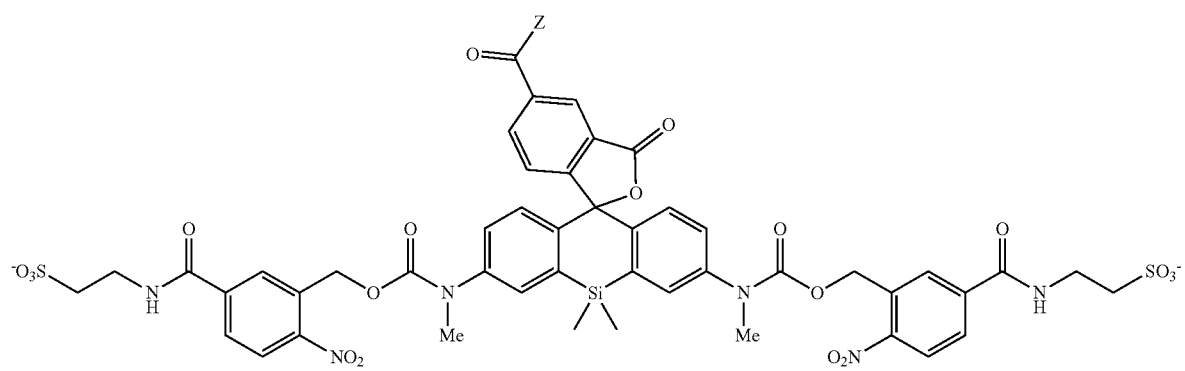
6'-IIIg
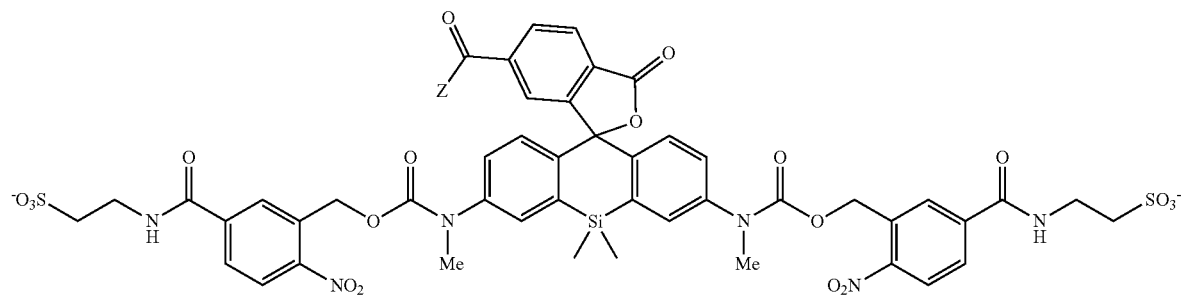
4'-IIIh
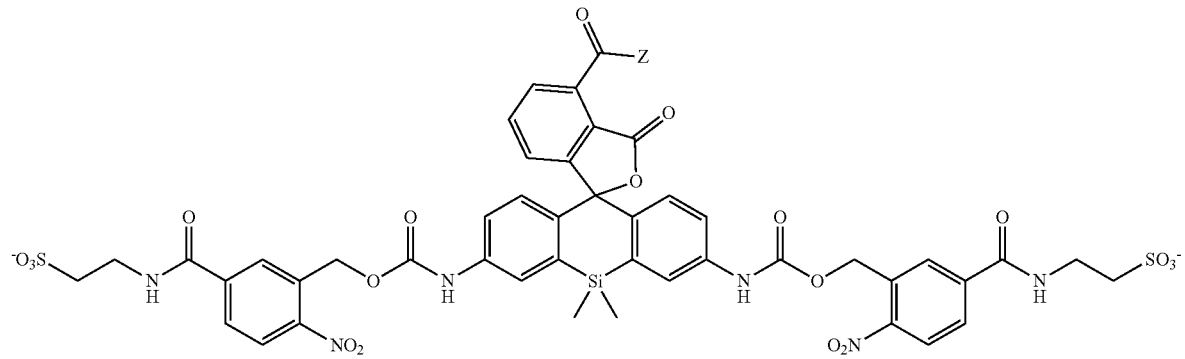

-continued
5'-IIIh
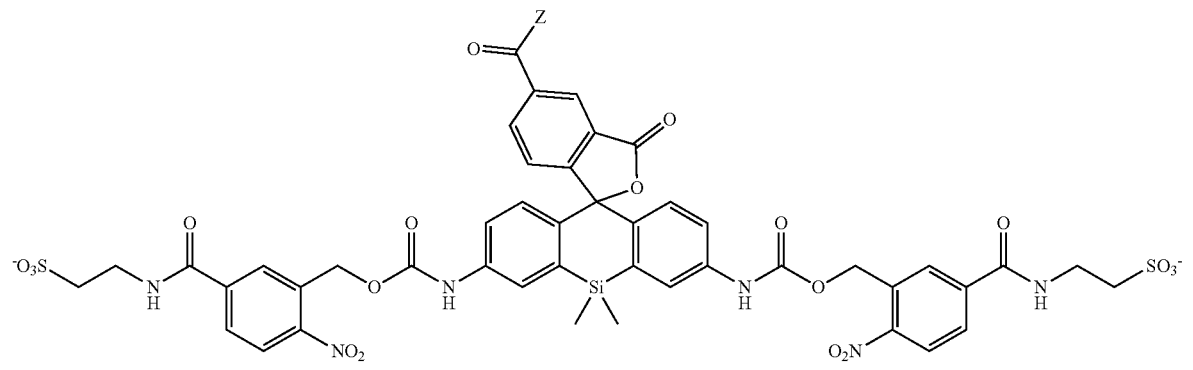
6'-IIIh
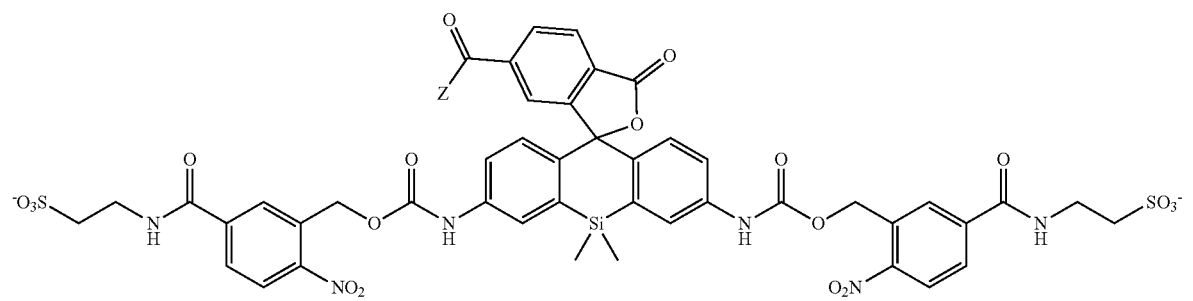
4'-IIIi
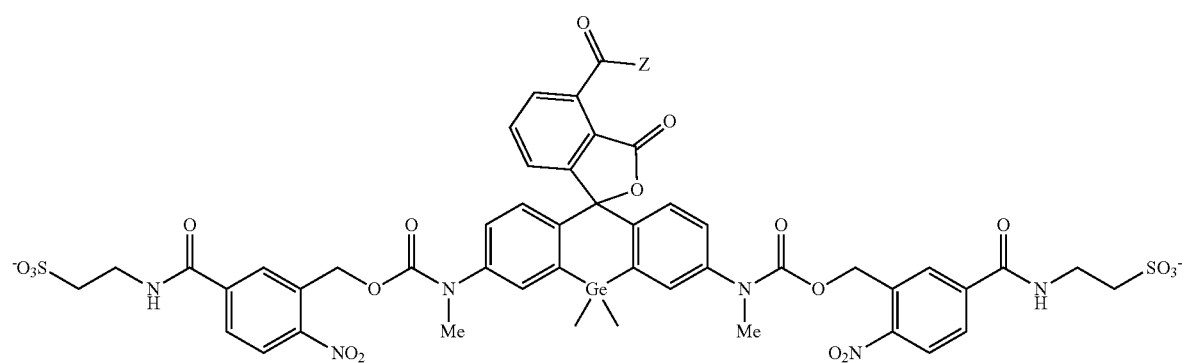
5'-IIIi
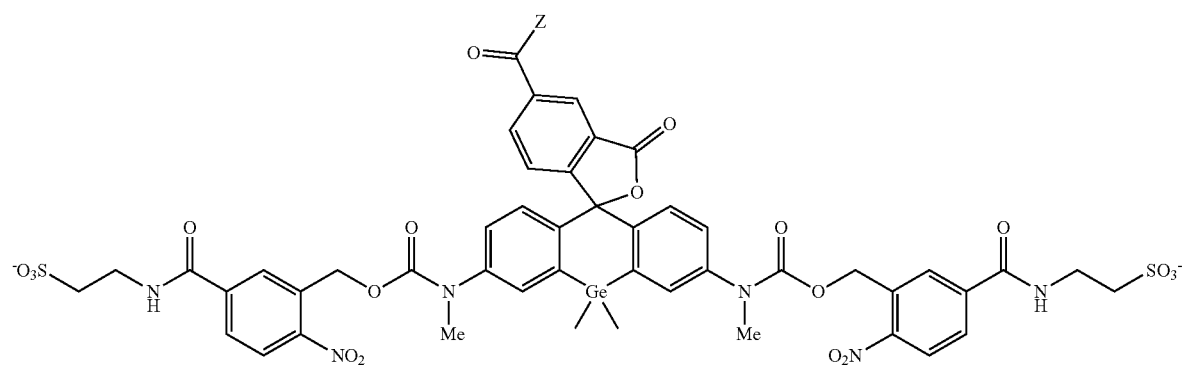

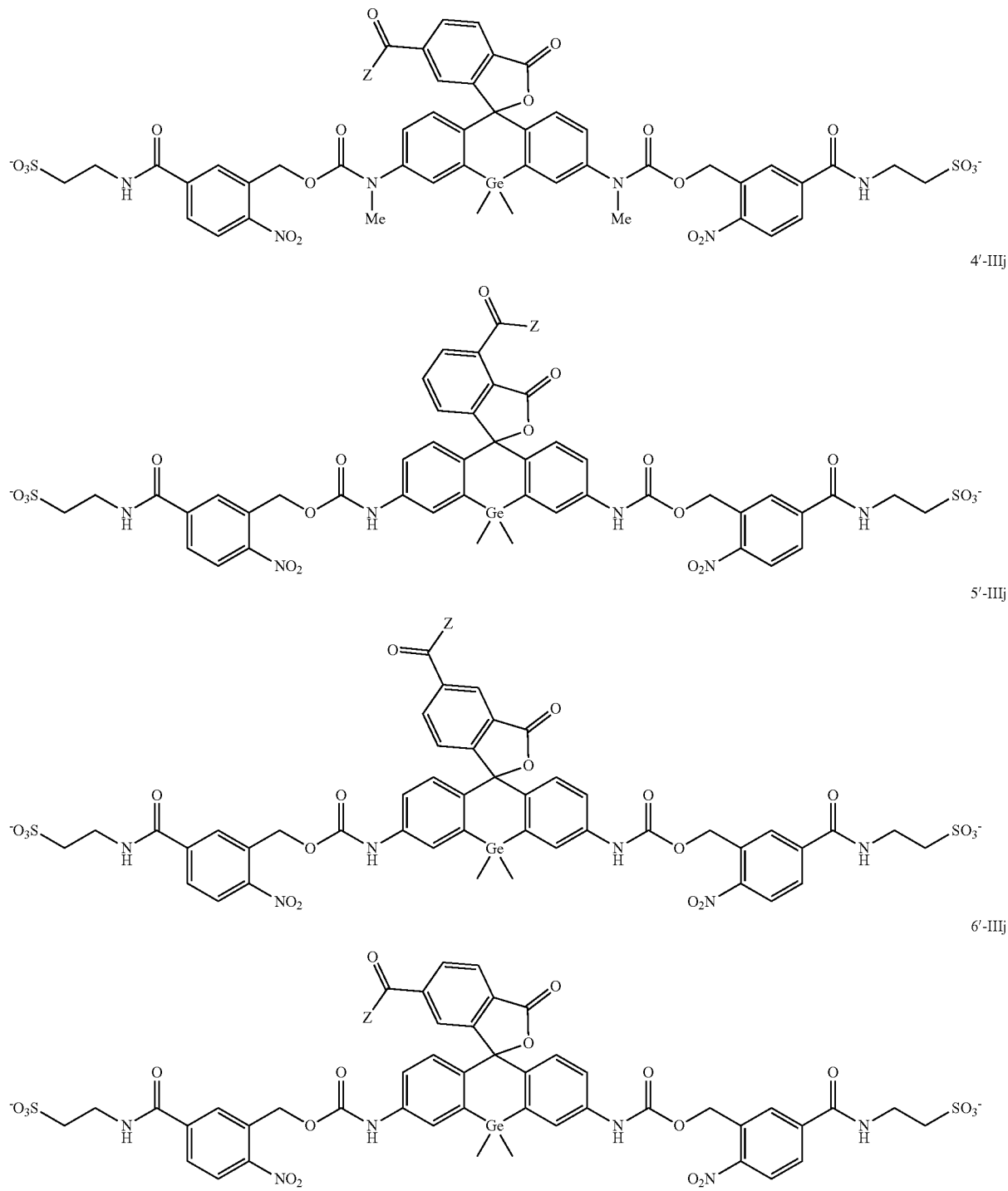

wherein the substituent Z may represent OH, NH-linker-CO₂H, O-ligand, NH-ligand or NH-linker-ligand.

For all compounds with the general structures IIa-IIj and more specific examples IIIa-IIIj, it is understood that free sulfonic acid forms (representable by replacement of $SO_3^-$ groups with $SO_3H$) as well as salts with inorganic cations (such as $H^+$, $Li^+$, $Na^+$, $K^+$, $NH_4^+$) and small organic cations, in particular cations of ammonium compounds, e.g. $Me_3NH^+$, $Et_3NH^+$, $Et(i-Pr)_2NH^+$, imidazole-$H^+$, pyridine-$H^+$ and similar cations, also represent embodiments of the present invention.

In some specific embodiments of the example compounds IIIa-IIIj, the substituent Z may represent a leaving group (such as azide, fluoride or a leaving group of an amino-reactive ester), in particular azide, fluoride, N-succinimidyloxy, 3-sulfo-N-succinimidyloxy, N-phthalimidyloxy, N-tetrachlorophthalimidyloxy, pentachlorophenoxy, pentafluorophenoxy, 2,3,5,6-tetrafluorophenoxy, 4-(hydroxysulfonyl)-2,3,5,6-tetrafluorophenoxy, 1-benzotriazolyloxy, or cyanomethoxy as depicted in the structural formulae below:

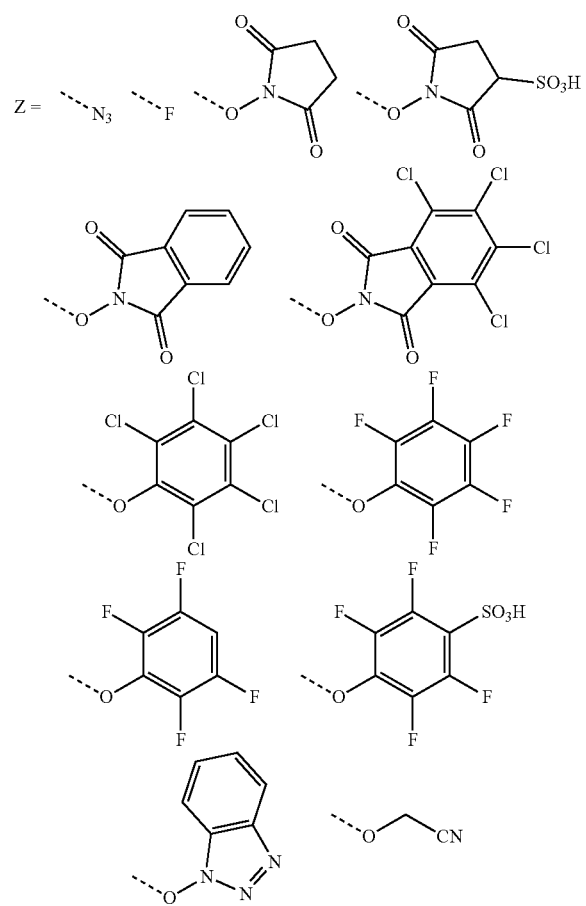

In other specific embodiments of the example compounds IIIa-IIIj, the substituent Z may represent NH-linker-CO$_2$H or NH-linker-CO—Z', where the substituent Z' represents one of the leaving groups defined as above for Z. Some nonlimiting examples of linkers include an alkyl (polymethylene) chain —(CH$_2$)$_n$—, where n=an integer from 1-20, or a PEG chain of the type —(CH$_2$CH$_2$O)$_n$— or —(CH$_2$CH$_2$O)$_{n-1}$—CH$_2$CH$_2$—, where n=an integer from 1-100. In some specific embodiments of the example compounds IIIa-IIIj, the substituent Z may represent O-ligand, NH-ligand or NH-linker-ligand, wherein the ligand moiety represents a reactive group or tag (in particular a biomolecular tag, i.e. a small molecule with a specific affinity or reactivity towards a particular biomolecule or a set of biomolecules), capable to form a covalent or non-covalent bond or molecular complex with a target chemical entity or substance.

More specifically, the ligand moiety may comprise or represent a reactive group which is selected from an activated ester, in particular a N-hydroxysuccinimidyl or pentafluorophenyl ester, an activated carbonate, in particular N-hydroxysuccinimidyl carbonate, an amine, a thiol, an azide, an alkene or alkyne, including a bicyclic and/or strained alkene or alkyne, a maleimide, a tetrazine group, or a ligand which is selected from the group comprising a HaloTag ligand, a SNAP-Tag ligand, a CLIP-Tag ligand, a TMPTag ligand, or a ligand for a protein which is a functional analog of these protein tags, biotin, a taxoid moiety, in particular paclitaxel, docetaxel, cabazitaxel, larotaxel or a structurally related compound, phalloidin, jasplakinolide and other high-affinity ligands.

The above listed compounds of the present invention provide the material (a caged fluorescent label) for imaging of one or more intra- or intercellular structure(s) within one or more cells or within biological tissue(s). The imaging method includes labeling living or fixed cells within the biological object of interest with one of the compounds of the present invention to provide the sample labeled with caged fluorescent dyes. The structure of the sample is then analyzed by: 1) activating a set of individual labels with an activation light of the selected wavelength or spectral range in the form of at least one diffuse, focused, shaped or patterned beam; followed by: 2) irradiating the sample with an excitation light of the selected wavelength or spectral range in the form of at least one diffuse, focused, shaped or patterned beam and 3) detecting the fluorescence signal, emitted from the sample, with a camera, photomultiplier tube, avalanche photodiode or any other suitable light detector, and recording the detected signal. The above sequence may be repeated multiple times as necessary, and the localization of individual fluorescent emitters is performed according to the selected technique of super-resolution fluorescence microscopy.

Definitions

The general chemical nomenclature terms, such as methyl (Me), alkane, aryl, cycloalkyl etc. used herein are to be understood in the most general sense according to the knowledge of those skilled in the art. For a detailed reference of the common definitions and terms in organic chemistry, the reader is addressed to the most recent editions of *Nomenclature of Organic Chemistry* (*Blue Book*) and *Compendium of Chemical Terminology* (*Gold Book*) published by the International Union of Pure and Applied Chemistry (IUPAC).

The term "cage" or "caging group" as used herein refers to a photoreactive or photolytically sensitive substituent (protecting group) that is designed to interfere with the (photo)physical properties and/or the chemical reactivity of the free probe. The caging group is eliminated by photolysis thus restoring the unprotected compound, allowing its release into the system of interest with a high degree of spatial and temporal control. In the context of the present invention, this unprotected compound represents a fluorescent dye molecule, which may be present in the system of interest as a freely diffusing molecule or attached to the object of interest via covalent or non-covalent interactions.

The term "linker" as used herein refers to a chemical group that connects two parts of a molecule through covalent bonds. Some representative examples of the linkers include an alkyl (polymethylene) chain —(CH$_2$)$_n$—, where n=1-20, a disubstituted cycloalkyl such as trans-1,4-cyclohexanediyl, a polyglycine chain of type —(NHCH$_2$C(=O))$_n$—, where n=1-10, a glycine-serine peptide linker of type (GS)$_n$, (GGS)$_n$, (GGGS)$_n$ or (GGGGS)$_n$, where n=1-10, or a PEG chain of type —(CH$_2$CH$_2$O)$_n$— or —(CH$_2$CH$_2$O)$_{n-1}$—CH$_2$CH$_2$—, where n=1-100.

The term "ligand" as used herein refers to a reactive group or tag, in particular biomolecular tag, capable to form a covalent bond(s) or non-covalent interactions or molecular complex with an (intra- or extracellular) target chemical entity or substance.

Said target chemical entity may comprise or represent, e.g., an amino acid (naturally occurring or artificially introduced), a peptide, protein, in particular an enzyme or antibody, a receptor, an ion channel, a nucleotide, nucleic acid sequence, including DNA and RNA, a lipid, a carbohydrate, a small-molecule cofactor, a pharmaceutical drug, a toxin, a metabolite.

In more specific embodiments, the target chemical entity may be for example a HaloTag, SNAP-tag, TMP-Tag, CLIP-Tag or a protein which is a functional analog of these original protein tags, i.e. which retains the capability to bind the same ligands/substrates; or any other protein applicable in bionanotechnology or molecular biology techniques, such as tubulin or actin, avidin, streptavidin.

In some specific embodiments, the reactive group may be for example an azide, tetrazine, a maleimide, an amine, a thiol, an activated ester (such as N-hydroxysuccinimidyl or pentafluorophenyl ester), an activated carbonate (such as N-hydroxysuccinimidyl carbonate), an alkene or alkyne, including a bicyclic and/or strained alkene or alkyne suitable for metal-free bioorthogonal click chemistry, such as TCO (trans-cyclooctene) or DBCO (dibenzocyclooctyne).

In other specific embodiments, the ligand may be a peptide, protein or nucleic acid sequence.

Some nonlimiting examples of preferred ligands include a HaloTag ligand (haloalkane), a SNAP-Tag ligand ($O^6$-benzylguanine or a pteridine or chloropyrimidine analog), a CLIP-Tag ligand ($O^2$-benzoylcytosine), a TMPTag ligand (trimethoprim and derivatives thereof), biotin, a taxoid moiety (covalently attached paclitaxel, docetaxel, cabazitaxel, larotaxel or similar derivative capable of binding to tubulin), phalloidin, jasplakinolide (or its functional analogs capable of binding to actin, such as the compounds 9a-c in [Borowiak et al., J. Am. Chem. Soc. 2020, 142(20), 9240-9249] in their deprotected form) and other high-affinity ligands.

The caged dye molecules of the present invention may also be conjugated to a biomolecule, such as a peptide, a protein or a DNA strand, responsible for selective targeting or binding of the caged dye, and the resulting conjugates may be employed for studying the system of interest. In these cases, the biomolecule responsible for selective targeting or binding is also considered to be a ligand or part thereof.

The term "activated ester" as used herein, refers to any ester-containing compound capable of reacting with functional groups, such as an amine or sulfhydryl groups, in particular with amine and sulfhydryl groups in a biomolecule. Some non-limiting examples of active esters are N-hydroxysuccinimidyl ester, N-hydroxysulfosuccinimidyl ester, N-hydroxyphthalimidyl ester, tetrafluorophenyl ester, and pentafluorophenyl ester. In the context of the present specification, the term "activated ester" is also extended to include acyl fluorides and acyl azides.

The term "activated carbonate" as used herein, refers to any organic carbonate ester-containing compound capable of reacting with functional groups, such as an amine or sulfhydryl groups, in particular with amine and sulfhydryl groups in a biomolecule. Some non-limiting examples of activated carbonates are N-hydroxysuccinimidyl carbonate and 1H-imidazole-1-carboxylate ester.

The term "leaving group" as used herein, refers to a molecular fragment that departs with a pair of electrons in heterolytic bond cleavage in a nucleophilic substitution reaction. Some non-limiting examples of leaving groups are chloride, fluoride, azide, N-succinimidyloxy, and pentafluorophenyloxy.

The term "substituted" as used herein is generally understood to include all permissible substituents of organic compounds, provided a) that such substitution is in accordance with permitted valence of the substituted atom and the substituent and b) that the substitution results in a compound sufficiently stable to perform under the conditions practical for the disclosed method, i.e. that a compound does not spontaneously undergo transformation such as by rearrangement, fragmentation, elimination, hydrolysis etc. long enough to practically perform as disclosed herein. In a broad aspect, the permissible substituents include acyclic and cyclic, branched and unbranched, carbocyclic and heterocyclic, aromatic and nonaromatic, neutral, positively and negatively charged substituents of organic compounds and combinations thereof. Unless stated otherwise, all chemical groups described herein include both unsubstituted and substituted varieties.

More specifically, the term "substituted" as used herein, may refer to the presence of one or more substituents selected from the group comprising straight or branched alkyl, in particular $C_1$-$C_4$ alkyl, e.g. methyl, ethyl, propyl, butyl, including isoalkyl, e.g. isopropyl, isobutyl, a secondary alkyl group, e.g. but-2-yl, a tert-alkyl group, e.g. 2-methylpropyl, alkenyl, alkynyl, aryl, hetaryl and functional groups such as halogen (fluoro, chloro, bromo, iodo), hydroxy, alkoxy, mercapto, alkylthio, amino, cyano, carboxylic acid, ester, ether, amide, sulfonamide, phosphonate etc.

The terms "alkyl" or "cycloalkyl", as used herein, generally comprise any unsubstituted or substituted (cyclo)alkyl groups, typically with 1-30 or more C atoms, in particular also a lower (cyclo)alkyl group. If not defined more specifically, the term "lower alkyl group" refers to $C_1$-$C_{10}$ alkyl groups, more preferred $C_1$-$C_6$ or $C_1$-$C_4$ alkyl groups. Some non-limiting examples thereof are methyl, ethyl, propyl, isopropyl, n-butyl, isobutyl, sec-butyl, pentyl, isopentyl, 2-methylbutyl, 2,2-dimethylpropyl, hexyl, isohexyl, 2-methyl-pentyl, 3-methylpentyl, 2,2-dimethylbutyl etc.

The term "alkenyl", as used herein, generally refers to a hydrocarbon group of from 2 to 20 carbon atoms with a structural formula containing at least one carbon-carbon double bond. The term is inclusive of linear and cycle-containing (i.e., cycloalkenyl) groups. Asymmetric structures, such as $(A^1A^2)C=C(A^3A^4)$, where at least one of the substituents $A^1, A^2$ is not H and at least one of the substituents $A^3, A^4$ is not H, are intended to include both the E and Z isomers. This can be presumed in structural formulae herein wherein an asymmetric alkene is present, or it can be explicitly indicated by the bond symbol C=C. The alkenyl group can be unsubstituted or substituted with one or more groups including, but not limited to, optionally substituted alkyl, cycloalkyl, alkoxy, alkenyl, cycloalkenyl, alkynyl, cycloalkynyl, ester, ether, halide, cyano, hydroxy, ketone, azide, silyl, sulfonyl, sulfide or thiol.

The term "alkynyl", as used herein, generally refers to a hydrocarbon group of from 2 to 20 carbon atoms with a structural formula containing at least one carbon-carbon triple bond. The term is inclusive of linear and cycle-containing (i.e., cycloalkynyl) groups. The alkynyl group can be unsubstituted or substituted with one or more groups including, but not limited to, (optionally substituted) alkyl, cycloalkyl, alkoxy, alkenyl, cycloalkenyl, alkynyl, cycloalkynyl, ester, ether, halide, cyano, hydroxy, ketone, azide, silyl, sulfonyl, sulfide or thiol.

The term "aryl", as used herein, refers to an unsubstituted or substituted mono-, bi- or tricyclic carbocyclic ring system having one, two or three aromatic rings including but not limited to phenyl, naphthyl, anthryl, azulyl, tetrahydronaphthyl, indanyl and indenyl.

In particular, the position numbers placed next to an aromatic ring indicate possible patterns of substitution in the molecules of the present invention, as exemplified here:

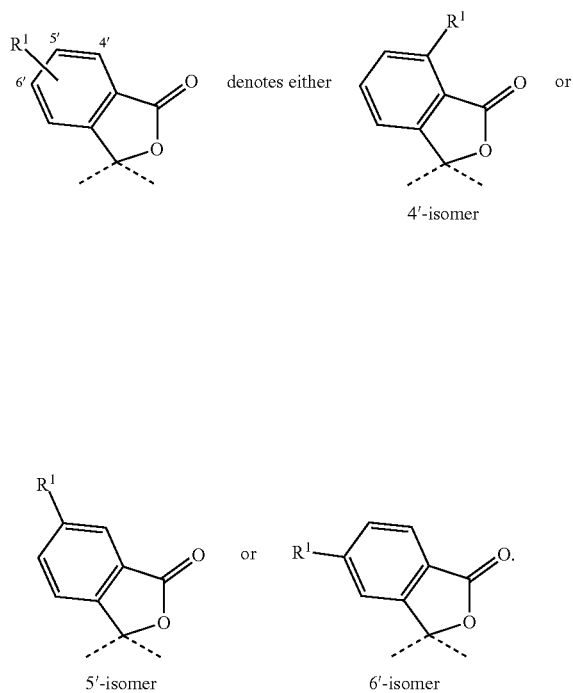

The terms "hetaryl" or "heteroaryl", as used herein, generally refer to an unsubstituted or substituted cyclic aromatic radical (residue) having from 3 to 10 ring atoms of which at least one ring atom is selected from S, O and N; the radical being joined to the rest of the molecule via any of the ring atoms. Representative, but not limiting examples are furyl, thienyl, pyridinyl, pyrazinyl, pyrimidinyl, pyrrolyl, imidazolyl, thiazolyl, oxazolyl, isooxazolyl, thiadiazolyl, oxadiazolyl, quinolinyl and isoquinolinyl.

The term "heterocycle", as used herein, comprises both cyclic aromatic (defined as "hetaryl" above) and cyclic non-aromatic radicals (residues) having from 3 to 10 ring atoms of which at least one ring atom is selected from S, O and N; the radical being joined to the rest of the molecule via any of the ring atoms. Representative, but not limiting examples of non-aromatic heterocycles are tetrahydrofuryl, tetrahydrothienyl, piperidinyl, piperazinyl, pyrrolidinyl, imidazolinyl, thiazolinyl, oxazolinyl, isoxazolinyl, dihydroquinolinyl and tetrahydroquinolinyl.

The term "halogen", as used herein, generally refers to fluorine, chlorine, bromine or iodine.

"HaloTag" refers to the modified *Rhodococcus rhodochrous* dehalogenase designed to covalently bind to synthetic haloalkane ligand by means of a nucleophilic substitution reaction, as described in [Los et al., ACS Chem. Biol. 2008, 3, 373-382], or any protein engineered or otherwise derived from it that retains the haloalkane dehalogenase functional activity and forms a covalent bond with its substrate.

"SNAP-Tag" refers to the modified $O^6$-alkylguanine-DNA alkyltransferase designed to react with substituted $O^6$-benzylguanine [Juillerat et al., Chemistry and Biology 2003, 10(4), 313-317], 2-amino-4-(benzyloxy)pteridine [Nelson et al., J. Med. Chem. 2004, 47(15), 3887-3891] or 2-amino-4-(benzyloxy)-6-chloropyrimidine [Kindermann and Schwab, Patent WO 2006114409 A1; Srikun et al., J. Am. Chem. Soc. 2010, 132, 4455-4465] derivatives, forming a covalent bond with the substrate (ligand), as described in [Juillerat et al., Chemistry and Biology 2003, 10(4), 313-317], or any protein engineered or otherwise derived from it that retains the ability to react with substituted $O^6$-benzylguanine derivatives (or pteridine or chloropyrimidine analogs) forming a covalent bond with the substrate (ligand).

"CLIP-Tag" refers to the modified $O^6$-alkylguanine-DNA alkyltransferase engineered to react with substituted $O^2$-benzoylcytosine derivatives forming a covalent bond with the substrate (ligand), as described in [Gautier et al., Chemistry and Biology 2008, 15(2), 128-136], or any protein engineered or otherwise derived from it that retains the ability to react with substituted $O^2$-benzoylcytosine derivatives forming a covalent bond with the substrate (ligand).

"TMPTag" refers to *E. coli* dihydrofolate reductase (eDHFR), non-covalently binding a trimethoprim ligand [Miller et al., Nat. Methods 2005, 2, 255-257], or its cysteine mutant (eDHFR:L28C), covalently binding a trimethoprim ligand modified with an electrophilic reactive group (e.g., acrylamide) [Wang et al., Biophysical Journal 2014, 106, 272-278; Chen et al., J. Am. Chem. Soc. 2012, 134(33), 13692-13699], or any protein engineered or otherwise derived from eDHFR that retains the ability to bind a trimethoprim ligand.

Unless defined otherwise, all technical and scientific terms used herein have the same meaning as commonly understood by a person skilled in the art to which the subject matter disclosed herein belongs. The procedures and methods disclosed herein are purely representative, and any methods, devices or materials similar or alternative to those described in preparation, testing or application of the presently-disclosed subject matter may be employed in practice.

General Approach for Synthesizing the Novel Compounds, in Particular Fluorescent Dyes, of the Invention For the preparation of the novel compounds, the present inventors have identified the following synthetic sequence starting from the advanced intermediates of type A1-A4, described previously in the literature (A1: Grimm and Lavis, Org. Lett. 2011, 13(24), 6354-6357, Grimm et al. Nat. Methods 2015, 12, 244-250; A2: Grimm et al., ACS Chem. Biol. 2013, 8, 1303-1310; A3: Grimm et al. Nat. Methods 2015, 12, 244-250, Grimm et al. ACS Cent. Sci. 2017, 3(9), 975-985, Butkevich et al. Chem. Eur. J. 2017, 23, 12114-12119; A4: Butkevich et al. Chem. Eur. J. 2017, 23, 12114-12119):

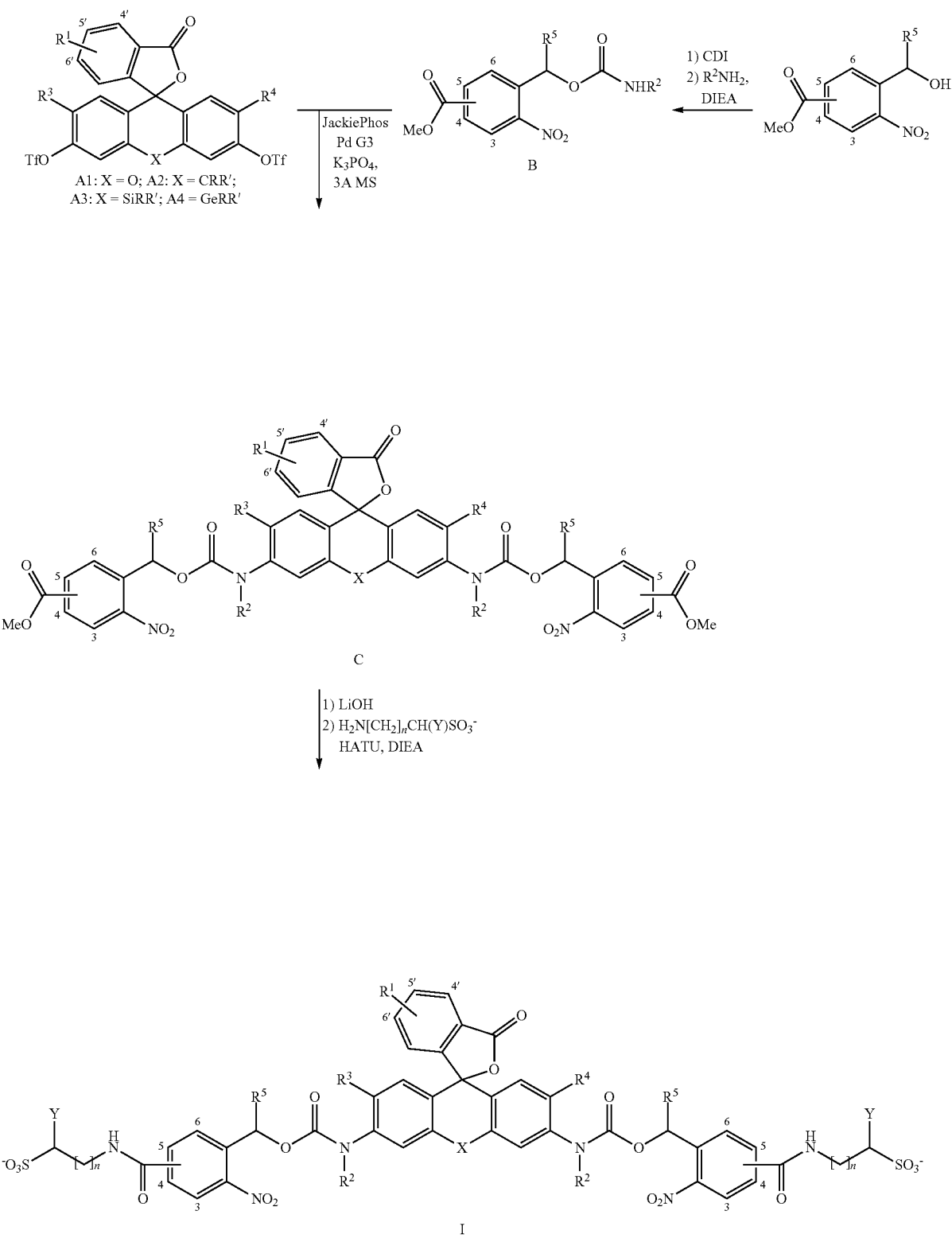

However, any suitable synthetic method can be used to synthesize compounds according to the present invention, with variations including the choice of catalysts, reaction conditions and the order of synthetic steps.

In some embodiments, the desired regioisomer of the photoactivatable dye ester (e.g. I, where $R^1$=4'-$CO_2$t-Bu, 5'-$CO_2$t-Bu or 6'-$CO_2$t-Bu) is then converted to a free carboxylic acid form or an active ester suitable for bioconjugation:

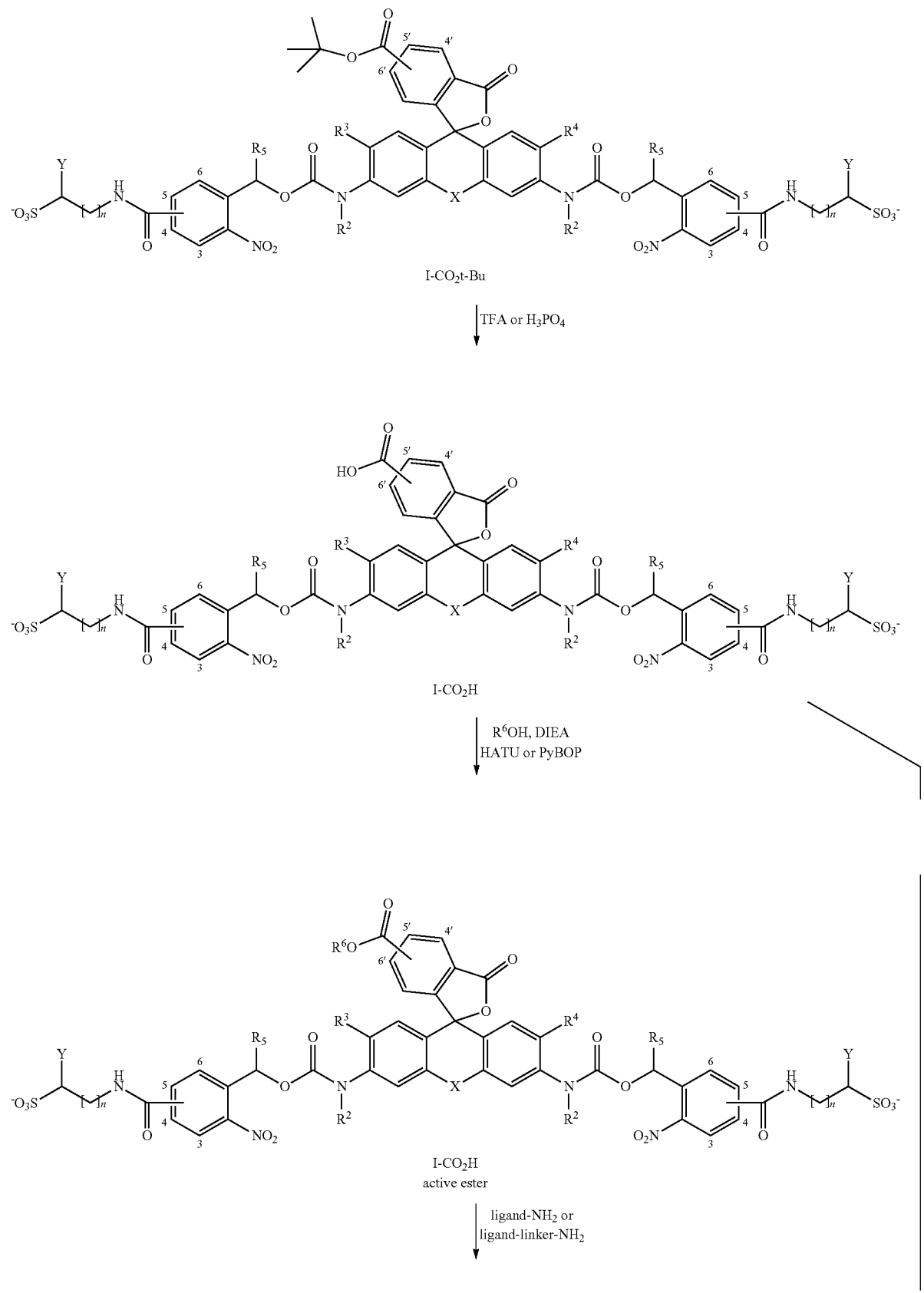

-continued
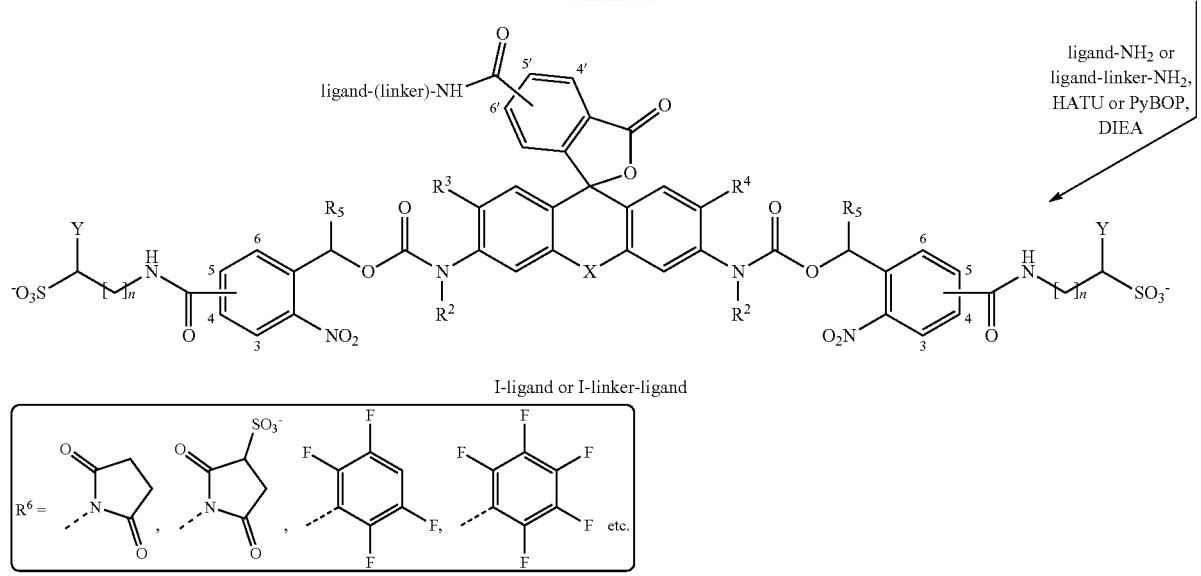
In other embodiments, a reactive group, such as maleimide (for thiol reactive labeling, e.g., of single-domain antibodies), azide, alkyne (for Cu-catalyzed click chemistry), tetrazine, strained alkene or strained alkyne (for metal-free click chemistry), is introduced for bioconjugation:
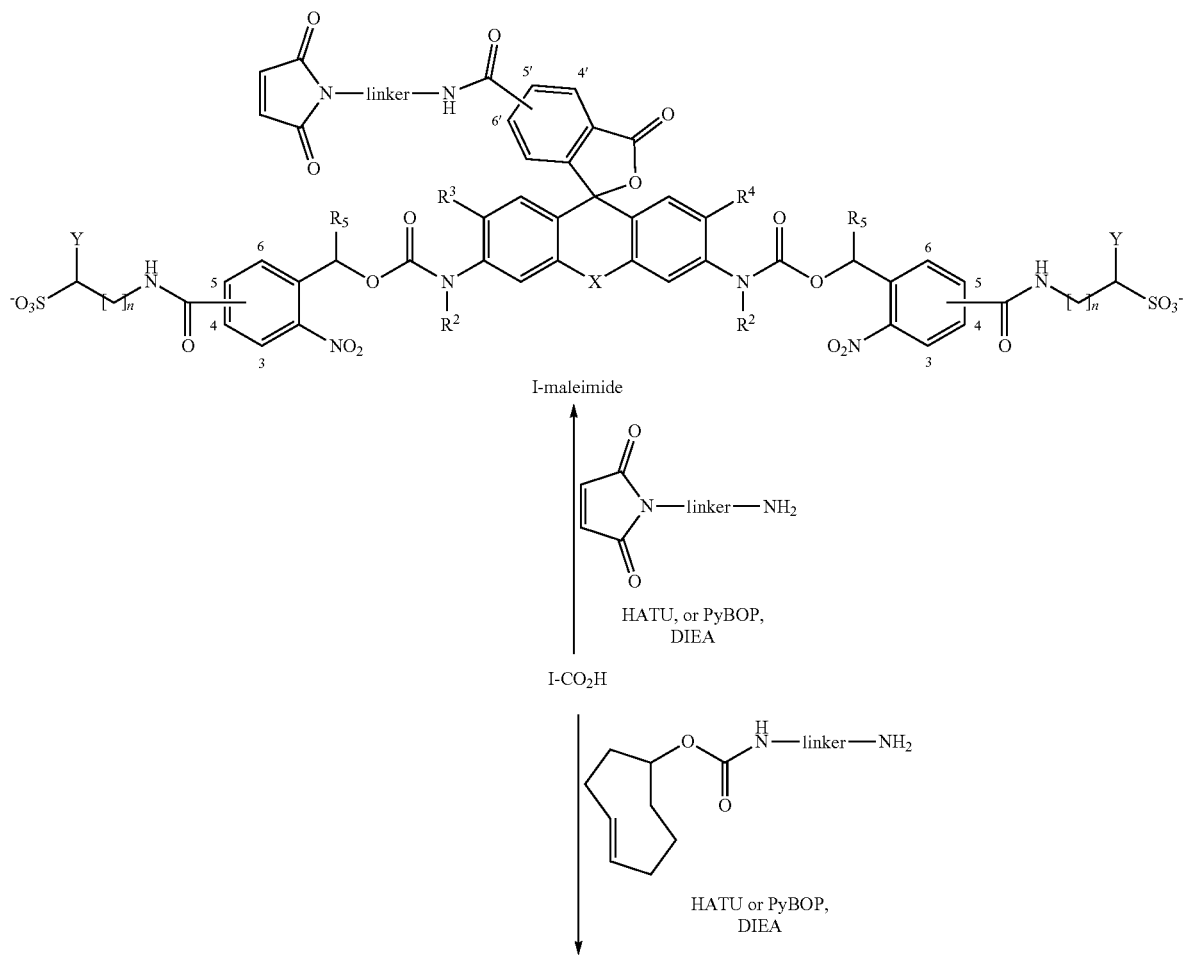

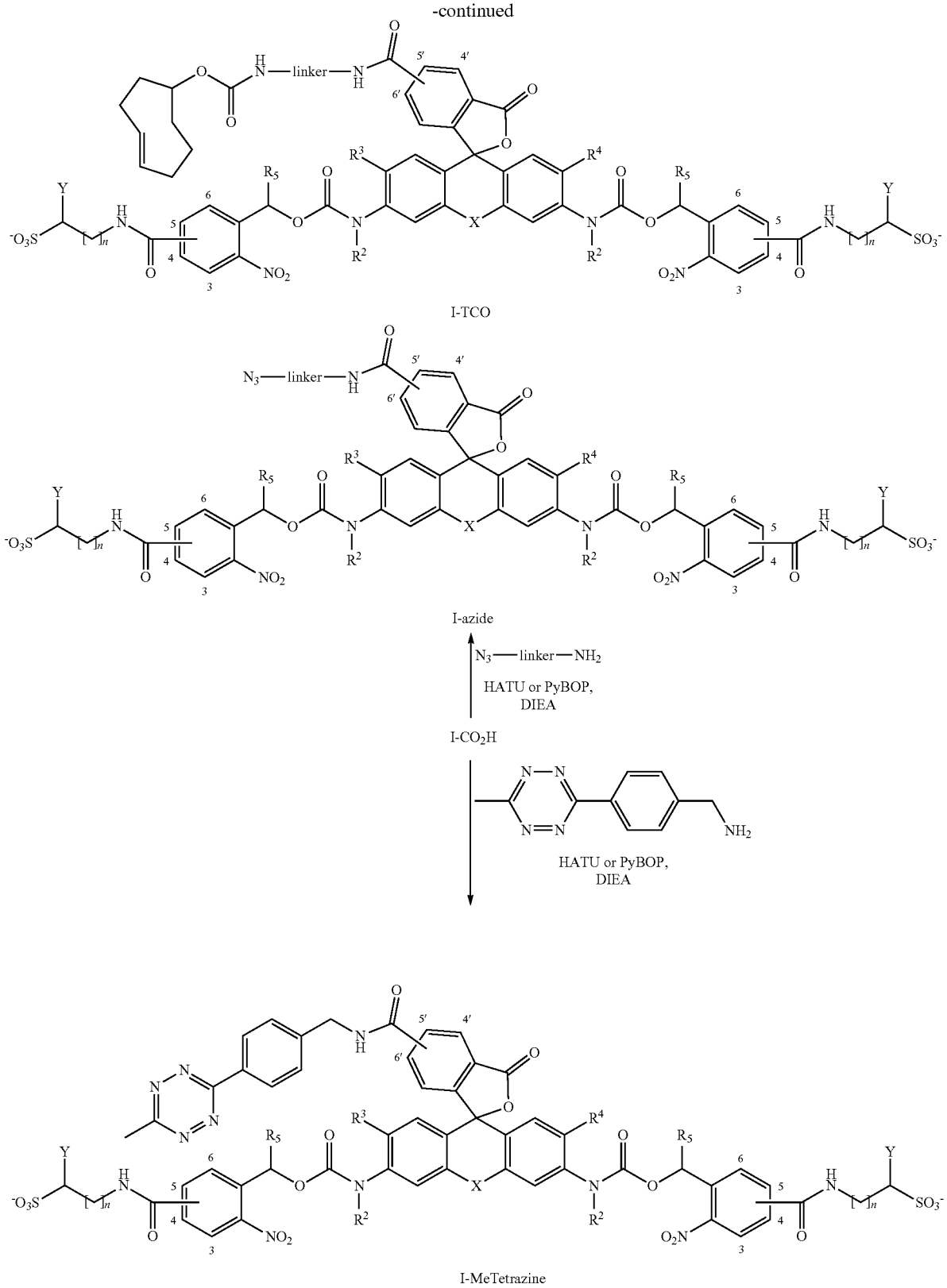
In other embodiments, a synthetic or semi-synthetic small-molecule ligand (6-chlorohexyl, $O^6$-benzylguanine, trimethoprim, biotin, phalloidin etc.) with a suitable linker for covalent or non-covalent conjugation to a biomolecular tag (HaloTag, SNAP-tag, TMP-Tag, CLIP-Tag, streptavidin, actin etc. respectively) is introduced for bioconjugation:

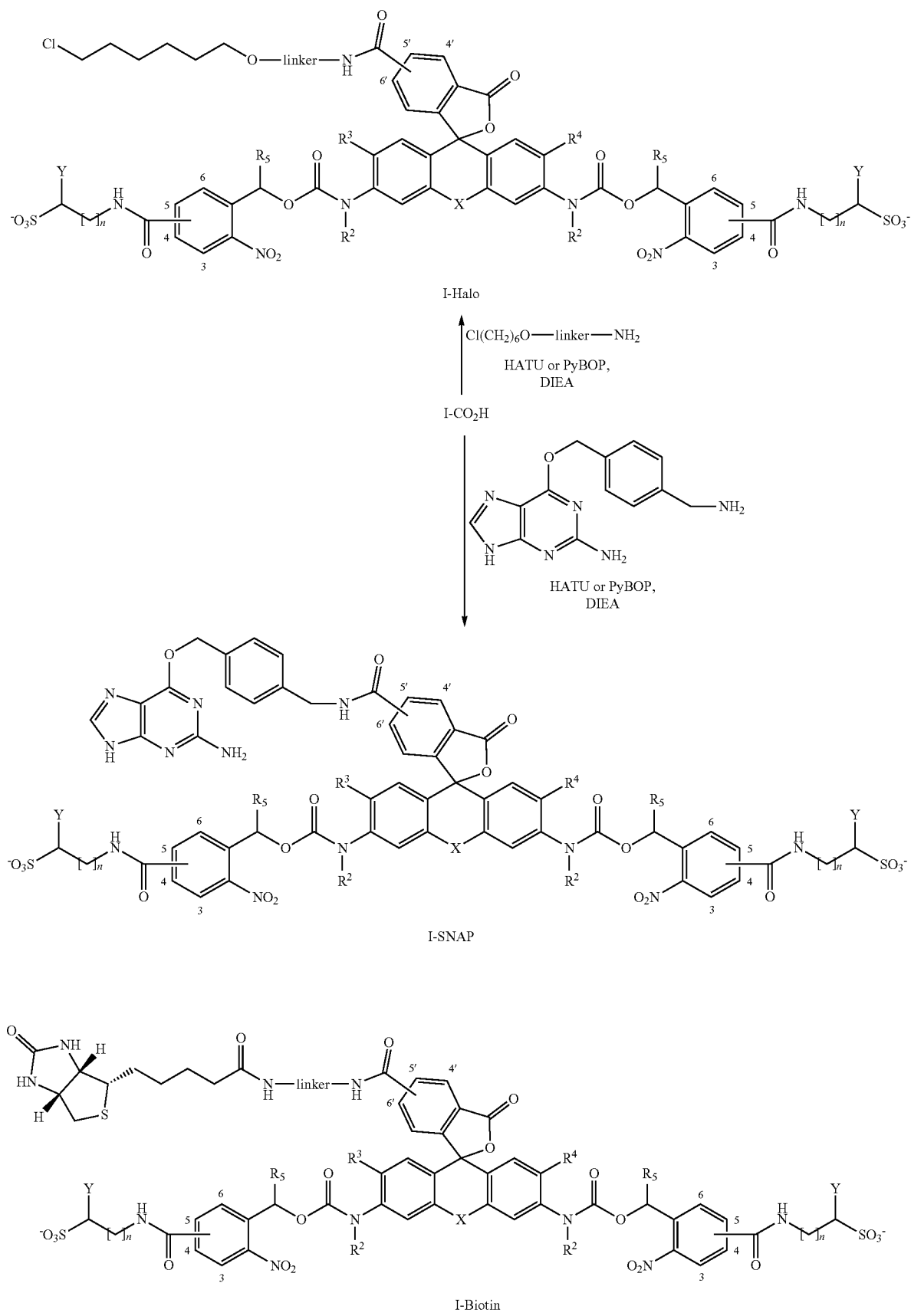

-continued

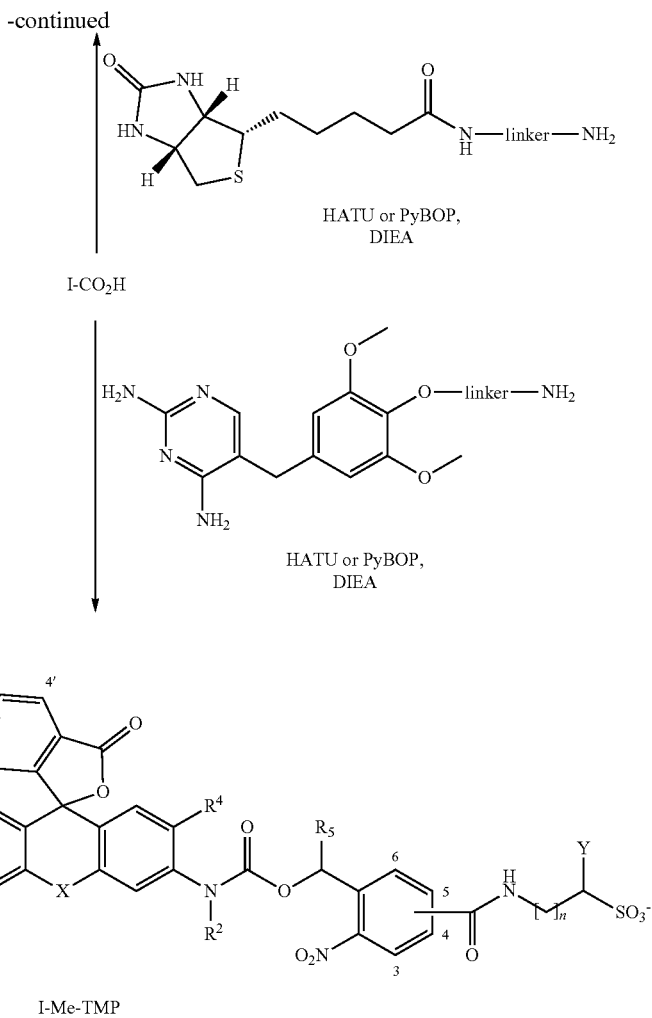

The photoactivatable (caged) fluorescent dyes of the present invention can be used as such, i.e. having the free ligands exemplified above, or in their conjugated form, i.e. covalently or non-covalently attached to a biomolecule such as expressed or isolated protein, polypeptide, glycan, lipid, DNA, RNA (including tRNA, mRNA, rRNA, long non-coding RNAs and all types of small RNAs), synthetic nucleic acid such as PNA or any other biomolecules used in molecular biology applications or diagnostic assays.

General Characteristics of the Novel Compounds (Caged Fluorescent Dyes) of the Invention The caged fluorescent dyes of the present invention are intended to be used in particular as photoactivatable fluorescent labels in super-resolution fluorescence microscopy methods in the context of fixed or living cells and extracellular matrix. General descriptions of various super-resolution imaging methods are presented in [Godin et al. Biophys J. 2014, 107, 1777-1784] and [Sahl, S. J.; Hell, S. W. High-Resolution 3D Light Microscopy with STED and RESOLFT. In: *High Resolution Imaging in Microscopy and Ophthalmology: New Frontiers in Biomedical Optics*; Bille, J. F., Ed.; Springer International Publishing, 2019; pp 3-32; DOI: 10.1007/978-3-030-16638-0_1], and representative applications of super-resolution microscopy in cell biology are presented in [Sahl et al. Nat. Rev. Mol. Cell Biol. 2017, 18, 685-701].

The requirements imposed by these methods and met by the caged fluorescent dyes of the present invention are as follows:

1) Photostability against visible and infrared (IR) light irradiation to prevent accidental uncaging and protect the caged fluorophore molecules from photobleaching. This allows to achieve a) subdiffractional resolution in a sample with another compatible label or b) activated subpopulations of the caged fluorophores in the presence of caged fluorophores of the present invention and c) spatiotemporal control of the activation unaffected by the superresolution imaging. In particular, the novel compounds are resistant against two-photon activation (uncaging) with a high-power 775 nm STED laser, producing very low fluorescence background levels, resulting in high contrast images upon uncaging;

2) The caged fluorescent dyes of the present invention are highly water-soluble and are suitable for labeling proteins or other biomolecules, viral particles, cells and tissues directly in aqueous media without or with minimal organic co-solvent addition (i.e., maximally similar to native conditions), or directly in imaging buffers;

3) Upon photoactivation, the caged fluorescent dyes of the present invention uncage to already validated and live-cell compatible fluorescent triarylmethane STED and SMLM labels such as 520R, 580CP or 620SiR [Butkevich et al. Angew. Chem. Int. Ed. 2016, 55, 3290-3294; Butkevich et al. Chem. Eur. J. 2017, 23, 12114-12119; Butkevich et al. ACS Chem. Biol. 2018, 13(2), 475-480], which have demonstrated good photostability and excellent functional compatibility with the labelled biomolecular targets;
4) Unlike in the case of using 2-nitrobenzyl or 4,5-dimethoxy-2-nitrobenzyl carbamate (NVOC) caging groups, the caging groups of the present invention upon photorelease of the fluorescent label are converted to highly water-soluble nitrosoaldehyde byproducts, which are intact cell-membrane impermeant. In case of intracellular target labelling, due to their anionic nature, these nitrosobenzaldehyde sulfonates are also expected to be less persistent within the cells and rapidly eliminated via natural efflux pathways;
5) The same caged fluorescent labels of the present invention can be employed across the different modalities of fluorescence nanoscopy: STED, PALM and MINFLUX;
6) The caged fluorescent labels of the present invention can be utilized to add additional features to existing fluorescence nanoscopy techniques by spatiotemporally controlled activation of subpopulations of the caged fluorophores and imaging and/or molecular tracking of the activated subpopulations.

Applications

As follows from the above-mentioned characteristics, the compounds (caged fluorescent dyes) of the present invention are suitable for various applications, in particular in the field of optic microscopy and bioimaging techniques.

The most basic aspect of the present invention relates to the use of a novel compound as defined above or of a conjugate comprising the same as a fluorescent label, probe, tracer or marker, as well as an energy donor or acceptor (reporter) in fluorescence energy transfer (FRET) experiments or as an energy acceptor (reporter) in bioluminescence resonance energy transfer (BRET) experiments, in imaging and optical microscopy.

In a more specific embodiment, these compounds, derivatives or conjugates may be used for tracking and monitoring dynamic processes in a sample or in an object.

In a more specific embodiment, these compounds, derivatives or conjugates may be used for tracking, monitoring and localizing nanoscale objects, in particular when the tracked objects are single molecules within a sample or an object.

In another specific embodiment, these compounds, derivatives or conjugates may be used as fluorescent tags, analytical reagents and labels in optical microscopy, imaging techniques, protein tracking, nucleic acid labeling, glycan analysis, flow cytometry or as a component of biosensors.

In another more specific embodiment, the hydrophilic cell-membrane impermeant caged dyes of the present invention can be used for studying receptor trafficking or ligand-driven cellular uptake of receptor-ligand complexes (e.g., using the methods outlined in [Poc et al., Chem. Sci. 2020, 11, 7871-7883]). As the caged dyes of the present invention uncage to the fluorophores that have demonstrated compatibility with live-cell imaging, they may be further employed for studying the intracellular distribution of the uptaken ligands with subdiffraction resolution using any of the optical microscopy methods listed below.

In still more specific embodiments, the optical microscopy and imaging methods may comprise stimulated emission depletion microscopy [STED] or any of its improved versions with reduced phototoxicity (e.g, FastRESCue STED), when additional color multiplexing is achieved by combining the caged dyes of the present invention together with any other STED-compatible fluorescent dyes in a single sample under study.

In another specific embodiment, the activation of spatiotemporal subpopulations of caged dyes of the present invention allows imaging with the uncaged fluorophore molecules while protecting the remaining caged fluorophores from photobleaching.

In another more specific embodiment, the selective activation of the presented caged dyes conjugated to biomolecules or other targets enables the imaging and/or tracking of individual molecules of the activated fluorophore subpopulation, which is used to study target localization or its involvement in biological processes by means of fluorescence nanoscopy or other optical microscopy methods.

In other specific embodiments, the optical microscopy and imaging methods may comprise single molecule switching techniques (SMS: diffraction unlimited optical resolution achieved by recording the fluorescence signals of single molecules, provided that they are reversibly or irreversibly switched between "dark" and "bright" states), such as single molecule localization microscopy [SMLM], photoactivation localization microscopy [PALM, PALMIRA, fPALM], stochastic optical reconstruction microscopy [STORM], minimal photon fluxes [MINFLUX] or their parallelized implementations), fluorescence correlation spectroscopy [FCS], fluorescence recovery after photobleaching [FRAP], fluorescence lifetime imaging [FLIM], ground state depletion with individual molecular return [GSD or GSDIM], and fluorescence resonant energy transfer [FRET].

The presently-disclosed subject matter further includes a method of using the compounds described herein. In some embodiments, the method comprises utilizing the uncaged fluorescent labels of the present invention as a reporter for enzyme activity, as a fluorescent tag, as a photosensitizer, as a pH indicator, as a redox indicator, as an intracellular environment polarity indicator, as an optical sensor of transmembrane potential, as a sensor for a target substance (an analyte), as an agent for imaging experiments, and/or as an imaging agent for super-resolution microscopy.

The presently-disclosed method for detecting a target substance can further comprise a detecting step that includes detecting an emission light from the compound, the emission light indicating the presence of the target substance, or a ratiometric detection step which comprises detecting an emission light before and after uncaging the dyes of the present invention within the sample.

In some embodiments the method for using the compounds comprises uncaging a compound of the present invention by exposing the sample to a UV or blue light. As described herein, the uncaging light source can produce an excitation wavelength from ultraviolet light to blue light in the visible range. In specific embodiments the excitation wavelength can be in a range of 200 nm to about 500 nm, or preferably in a range of about 350 nm to about 450 nm.

In some embodiments the method for using the compounds comprises uncaging a compound of the present invention by exposing the sample to an orange, red or infrared (IR) light making use of multiphoton excitation conditions. As described herein, the uncaging light source can be an orange, red or IR laser of sufficiently high power. In specific embodiments the excitation wavelength can be in a range of 500 nm to about 1500 nm, or preferably in a range of about 700 nm to about 1100 nm.

In some embodiments the method for using the compounds further comprises exciting the uncaged compound by exposing the sample to an excitation light that includes an absorption wavelength. As described herein, the excitation light can include an absorption wavelength from ultraviolet light to near infrared light. In specific embodiments the absorption wavelength can be in a range of 200 nm to about 1000 nm, or preferably in a range of about 400 nm to about 800 nm.

In some embodiments the detecting step is performed by use of fluorescence spectroscopy or by the naked eye. In some embodiments the detecting step is performed with a microscope. In some embodiments the detecting step is performed with a fluorimeter or a microplate reader, or within a flow cell. In some embodiments the presence of a target substance can indicate the occurrence or absence of a particular biological function, as will be appreciated by those skilled in the art. In some embodiments the method is performed in a live cell, a tissue and/or a subject. Some embodiments of detection methods comprise contacting the sample with two or more embodiments of compounds that are selective for different target substances. Methods for detecting two or more target substances with two or more of the presently-disclosed compounds are referred to herein as "multiplex" detection methods.

In some of the present multiplex methods, two or more distinct target substances and/or two or more regions of one target substance are detected using two or more probes, wherein each of the probes is labeled with a different embodiment of the present compounds. The presently-disclosed compounds can be used in multiplex detection methods for a variety of target substances, whereby the first compound can be selective for a first target substance, is excited with a first absorption wavelength and can be emitting a first emission light, and the second compound can be selective for a second target substance, is excited with a second absorption wavelength and can be emitting a second emission light, while both compounds are sharing the same uncaging conditions (multiplexing by excitation or emission wavelengths). In other embodiments of the multiplex methods, the caged compounds of the present studies are employed together with the common fluorophores that do not require an uncaging step to be used in fluorescence detection methods (multiplexing by uncaging). In some embodiments the emission wavelengths of the first and second compounds are different from one another, and in other embodiments the excitation (absorption) wavelengths of the first and second compounds are different from one another (multiplexing by Stokes shift), providing an efficient means for detecting a plurality of different target substances in one setting.

As a non-limiting illustrative example, imaging in samples can be performed with one or more than one pair of primary and mutually orthogonal secondary antibodies, labelled with commonly used STED-compatible fluorescent dyes (such as ATTO 594 or Abberior STAR 635P) and caged dyes of the present invention (e.g., 13, 17 or 21) emitting in the same spectral detection channel. The commonly used always-on dyes can then be imaged with STED using their respective excitation lasers (e.g., 561 nm or 640 nm laser) and detection channels (e.g., 605-625 nm and 655-715 nm). These fluorescent dyes can then be photobleached using low power of 595 nm STED light without activating the caged dyes of the present invention. The caged dyes can then be activated by illumination with e.g. a 405 nm broadband LED for several seconds (or with a corresponding suitable activation laser) and imaged with the same excitation lasers and detection channels as before for the normal always-on fluorophores. This imaging routine allows to duplex every available color channel on a commercial 775 nm STED system (STED 595/775 quad scanning microscope, Abberior Instruments, Göttingen, Germany), but can be adapted to suit another STED instrument from a different supplier or a custom-built STED nanoscopy setup.

Figure 1:
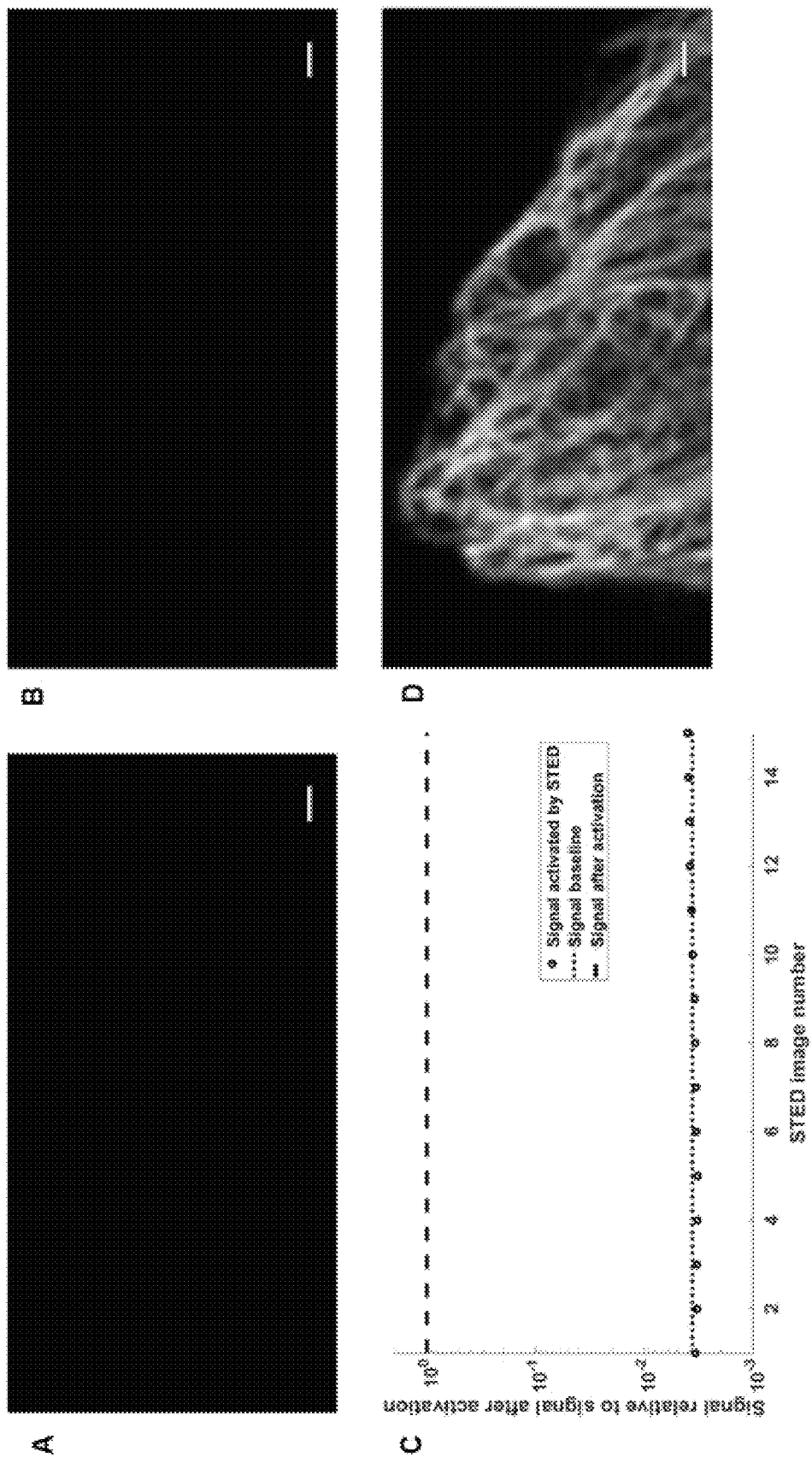
FIG. 1 shows confocal images of ice-cold methanol fixed U2OS cells stained with primary antibody (Abcam: ab18251) against alpha-tubulin and secondary antibody (Dianova: 111-005-003) conjugated to 21-NHS: A—sample before UV activation (broadband 405 nm LED); B—sample before UV activation after one STED frame recorded (775 nm STED laser); C—average fluorescence signal before UV activation during multiple STED frames relative to fluorescence signal after UV activation; D—sample after UV activation. Scale bar 1 μm.
Figure 2:
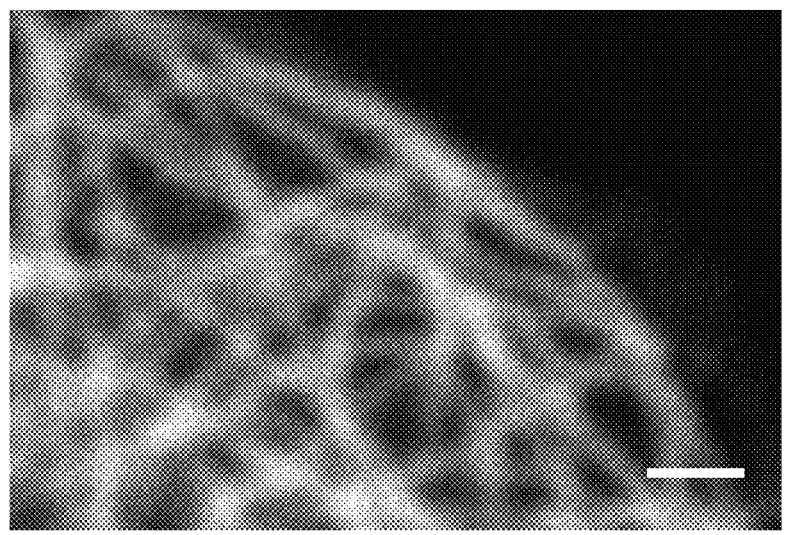
FIG. 2 shows images of ice-cold methanol fixed U2OS cells stained with primary antibody (Abcam: ab18251) against alpha-tubulin and secondary antibody (Dianova: 111-005-003) conjugated to 21-NHS after UV activation (broadband 405 nm LED): A—confocal; B—STED (775 nm). Scale bar 1 μm.
Figure 2:
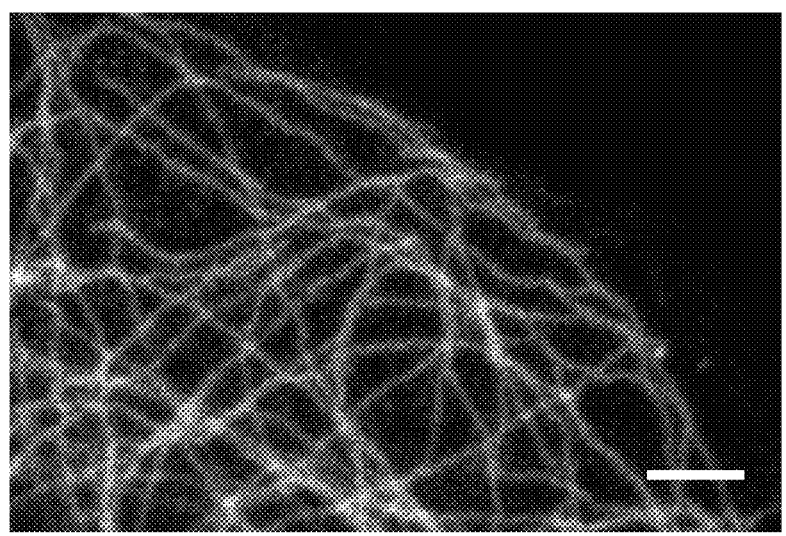
Figure 3:
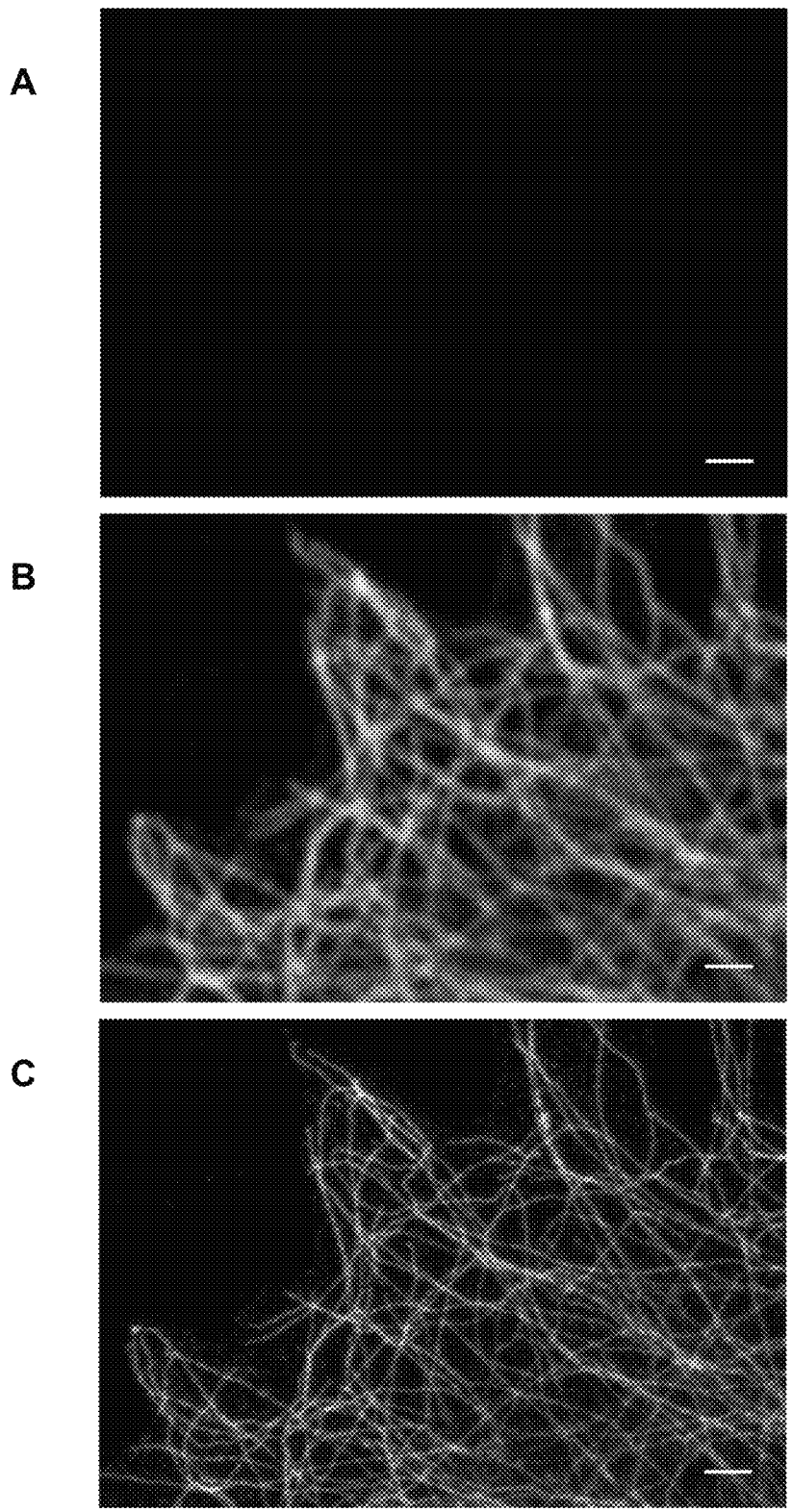
FIG. 3 shows images of ice-cold methanol fixed U2OS cells stained with a primary antibody (Abcam: ab18251) against alpha-tubulin and secondary (Dianova: 111-005-003) antibody conjugated to 13-NHS: A,B—confocal before (a, background) and after UV activation with a broadband 405 nm LED (B); C—STED (775 nm) after UV activation with a broadband 405 nm LED.

The present invention is further illustrated by the following specific but non-limiting examples.

EXAMPLE 1

Synthesis of Starting Materials and Photoactivatable Dyes 5-(Methoxycarbonyl)-2-nitrobenzyl 1H-imidazole-1-carboxylate (1)

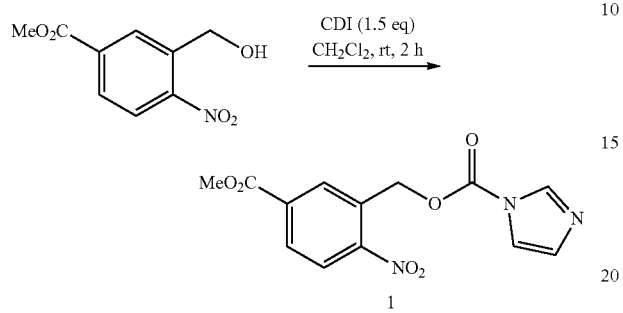

Compound 1. 1,1'-Carbonyldiimidazole (CDI; 972 mg, 6 mmol, 1.5 eq) was added portionwise to a stirred solution of methyl 3-(hydroxymethyl)-4-nitrobenzoate (844 mg, 4 mmol) in dry $CH_2Cl_2$ (20 mL). After stirring for 2 h at rt, sat. aq. $NH_4Cl$ (20 mL) was added and the reaction mixture was extracted with $CH_2Cl_2$ (3×20 mL). The combined extracts were dried over $Na_2SO_4$, filtered, evaporated, the residue was dissolved in EtOAc and the solution was passed through a plug of silica gel, washing with EtOAc. The filtrate was evaporated to viscous light yellow oil, which was freeze-dried from 1,4-dioxane to provide 1 as yellowish solid (832 mg, 68%).

$^1$H NMR (400 MHZ, $CDCl_3$): δ 8.31 (dd, J=1.7, 0.8 Hz, 1H), 8.23 (dd, J=8.5, 1.7 Hz, 1H), 8.20 (d, J=8.4 Hz, 1H), 7.46 (t, J=1.5 Hz, 1H), 7.11 (d, J=1.5 Hz, 1H), 5.84 (s, 2H), 3.99 (s, 3H).

$^{13}$C NMR (101 MHZ, $CDCl_3$): δ 164.7, 150.3, 148.3, 137.3, 135.1, 131.2, 131.1, 131.0, 130.3, 125.7, 117.3, 65.9, 53.2.

HRMS ($C_{13}H_{11}N_3O_6$): m/z (positive mode)=306.0718 (found [M+H]$^+$), 306.0721 (calc.).

Methyl 3-(methylcarbamoyloxy)methyl-4-nitrobenzoate (2)

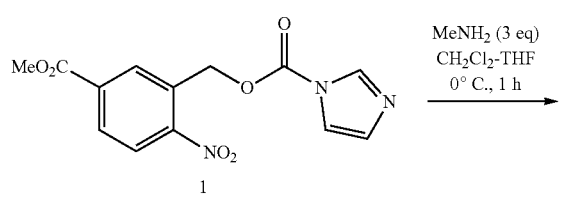

Compound 2. To a solution of 1 (610 mg, 2 mmol) in dry $CH_2Cl_2$ (7 mL), cooled in ice-water bath, methylamine (2 M in THF; 3 mL, 6 mmol, 3 eq) was added dropwise. The reaction mixture was stirred at 0-5° C. for 1 h and evaporated on Celite. The product was isolated by flash chromatography on Biotage Isolera system (40 g Teledyne ISCO RediSep Rf cartridge, gradient 20% to 100% EtOAc/hexane) to yield 512 mg (96%) of 2 as white solid.

$^1$H NMR (400 MHZ, $CDCl_3$): δ 8.26 (s, 1H), 8.10 (s, 2H), 5.51 (s, 2H), 4.91 (br.s, 1H), 3.97 (s, 3H), 2.84 (d, J=4.9 Hz, 3H).

$^{13}$C NMR (101 MHZ, $CDCl_3$): δ 165.2, 156.3, 150.0, 134.6, 133.6, 130.3, 129.8, 125.1, 62.9, 53.0, 27.8.

HRMS ($C_{11}H_{12}N_2O_6$): m/z (positive mode)=269.0767 (found [M+H]$^+$), 269.0768 (calc.).

Methyl 3-(carbamoyloxy)methyl-4-nitrobenzoate (3)

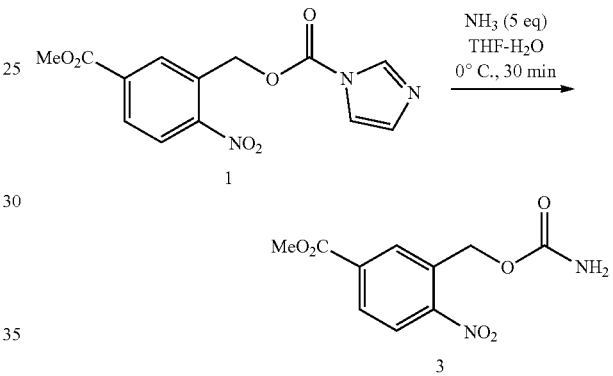

Compound 3. To a solution of 1 (196 mg, 0.64 mmol) in THF (2.5 mL), cooled in ice-water bath, aq. ammonia (25%, ~13 M in water; 0.25 ml, 3.21 mmol, 5 eq) was added dropwise. The reaction mixture was stirred at 0-5° C. for 30 min, diluted with methanol and evaporated to dryness on Celite. The product was isolated by flash chromatography on Biotage Isolera system (12 g Interchim SiHP 30 μm cartridge, gradient 20% to 100% EtOAc/hexane) to yield 103 mg (63%) of 3 as white solid.

$^1$H NMR (400 MHz, DMSO-$d_6$): δ 8.21 (d, J=8.5 Hz, 1H), 8.18 (d, J=2.0 Hz, 1H), 8.10 (dd, J=8.5, 2.0 Hz, 1H), 6.98 (br.s, 1H), 6.69 (br.s, 1H), 5.35 (s, 2H), 3.92 (s, 3H).

$^{13}$C NMR (101 MHz, DMSO-$d_6$): δ 164.7, 156.0, 149.7, 133.8, 133.7, 129.5, 129.3, 125.4, 61.3, 52.9.

HRMS ($C_{10}H_{10}N_2O_6$): m/z (positive mode)=255.0611 (found [M+H]$^+$), 255.0612 (calc.).

tert-Butyl (3-((6-(azidomethyl)pyridin-3-yl)amino)-3-oxopropyl)carbamate (4)

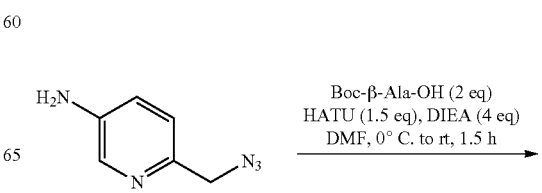

51

-continued

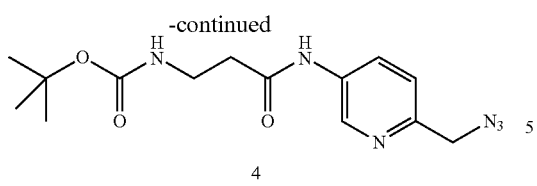

4

Compound 4. To a solution of 6-(azidomethyl)pyridin-3-amine [Jiang et al. Bioconjugate Chem. 2014, 25, 698-706] (132 mg, 0.88 mmol), N,N-ethyldiisopropylamine (DIEA; 0.62 mL, 3.52 mmol, 4 eq) and Boc-β-Ala-OH (333 mg, 1.76 mmol, 2 eq) in dry DMF (1.5 mL), cooled in ice-water bath, solid HATU (502 mg, 1.32 mmol, 1.5 eq) was added in portions over 5 min. The resulting yellow-green solution was warmed up to rt and stirred for 1.5 h. The reaction mixture was poured into sat. aq. $NaHCO_3$ (50 mL) and extracted with EtOAc (3×25 mL). The combined extracts were washed with water, brine, dried over $Na_2SO_4$, filtered and evaporated on Celite. The product 4 was isolated by flash chromatography on Biotage Isolera system (12 g Interchim SiHP 30 μm cartridge, gradient 50% to 100% EtOAc/hexane) and freeze-dried from dioxane to give 264 mg (94%) of pinkish solid.

$^1$H NMR (400 MHZ, $CDCl_3$): δ 8.72 (br.s, 1H), 8.62 (d, J=2.5 Hz, 1H), 8.20 (dd, J=8.5, 2.5 Hz, 1H), 7.29 (d, J=8.5 Hz, 1H), 5.22 (br.t, J=7.7 Hz, 1H), 4.43 (s, 2H), 3.50 (q, J=6.3 Hz, 2H), 2.64 (t, J=5.9 Hz, 2H), 1.42 (s, 9H).

$^{13}$C NMR (101 MHz, $CDCl_3$): δ 170.4, 156.8, 150.9, 141.1, 134.6, 127.9, 122.4, 80.2, 55.4, 38.0, 36.5, 28.5.

HRMS ($C_{14}H_{20}N_6O_3$): m/z (positive mode)=321.1663 (found [M+H]$^+$), 321.1670 (calc.).

52

3-Amino-N-(6-(azidomethyl)pyridin-3-yl)propanamide, bis(trifluoroacetate) salt (5)

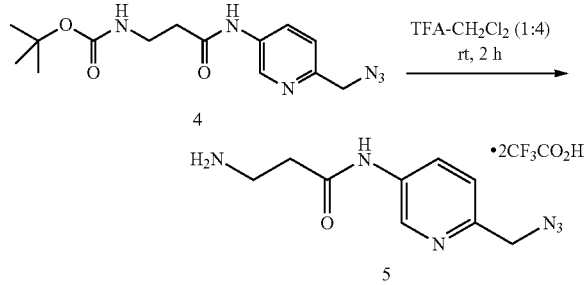

Compound 5. Trifluoroacetic acid (0.5 mL) was added to a solution of 4 (64 mg, 0.2 mmol) in $CH_2Cl_2$ (2 mL), and the resulting mixture was stirred at rt for 2 h. It was then diluted with toluene (5 mL), evaporated, chased with toluene-$CH_2Cl_2$ (5 mL) and dioxane (2×5 mL) and dried in vacuo to give the product 5 as viscous light brown oil (90 mg, ~100%).

$^1$H NMR (400 MHZ, DMSO-$d_6$): δ 10.49 (s, 1H), 8.77 (d, J=2.6 Hz, 1H), 8.07 (dd, J=8.4, 2.6 Hz, 1H), 7.81 (br.s, 4H, $NH_3^+$+NH$^+$), 7.43 (d, J=8.4 Hz, 1H), 4.46 (s, 2H), 3.11 (q, J=6.1 Hz, 2H), 2.74 (t, J=6.8 Hz, 2H).

$^{13}$C NMR (101 MHZ, DMSO-$d_6$): δ 169.0, 158.4 (q, $^2J_{C-F}$=36.1 Hz, $CF_3CO_2^-$), 150.0, 140.3, 135.1, 127.2, 122.8, 115.77 (q, $^1J_{C-F}$=291.9 Hz, $CF_3CO_2^-$), 54.0, 34.8, 33.2.

HRMS ($C_9H_{12}N_6O$): m/z (positive mode)=221.1140 (found [M+H]$^+$), 221.1145 (calc.).

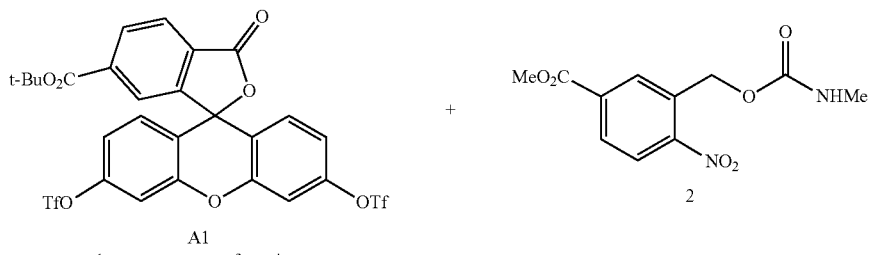

A1
($R^1$ = 6'–$CO_2$t-Bu, $R^3$ = $R^4$ = H)

JackiePhos Pd G3 (15 mol %)
JackiePhos (15 mol %)
$K_3PO_4$ (4 eq)
3A MS (400 mg/mmol)
toluene, 110° C., 6 h

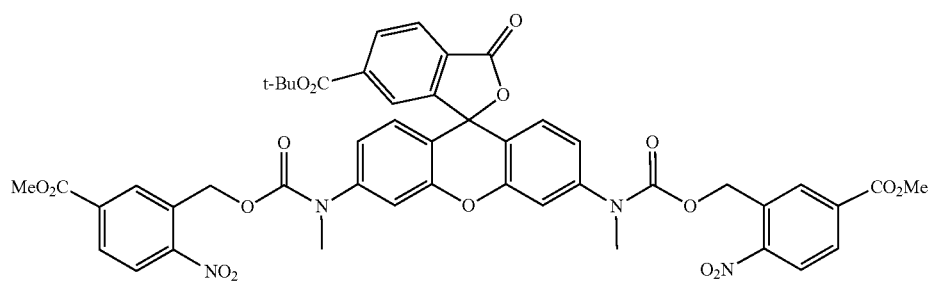

6

Compound 6. In a flame-dried 10 ml tube, loaded with anhydrous $K_3PO_4$ (119 mg, 0.56 mmol, 4 eq) and 3 Å molecular sieves (56 mg), compound A1 [Grimm et al. Nat. Methods 2015, 12, 244-250] (98 mg, 0.14 mmol), compound 2 (90 mg, 0.34 mmol, 2.4 eq), JackiePhos Pd G3 precatalyst (24.5 mg, 0.021 mmol, 15 mol %) and Jackie-Phos ligand (16.7 mg, 0.021 mmol, 15 mol %) were loaded. The tube was sealed, anhydrous toluene (1.4 mL) was injected, the mixture was degassed on a Schlenk line and stirred at 110° C. for 6 h. It was then diluted with $CH_2Cl_2$, filtered through a plug of Celite (washing with $CH_2Cl_2$ and EtOAc-$CH_2Cl_2$), the filtrate was evaporated on Celite and the product was isolated by flash chromatography on Biotage Isolera system (25 g Interchim SiHP 30 μm cartridge, gradient 20% to 80% EtOAc/hexane) and freeze-dried from dioxane to yield 92 mg (70%) of 6 as white solid.

$^1$H NMR (400 MHZ, $CDCl_3$): δ 8.25 (dd, J=8.0, 1.3 Hz, 1H), 8.17 (br.s, 2H), 8.12-8.05 (m, 5H), 7.84 (s, 1H), 7.27 (d, J=2.2 Hz, 2H), 7.05 (dd, J=8.5, 2.2 Hz, 2H), 6.82 (d, J=8.5 Hz, 2H), 5.68-5.52 (m, 4H), 3.90 (s, 6H), 3.39 (s, 6H), 1.54 (s, 9H).

$^{13}$C NMR (101 MHZ, $CDCl_3$): δ 168.5, 165.0, 164.1, 154.4, 153.0, 151.5, 150.0, 145.1, 138.7, 134.6, 132.8, 131.3, 130.5, 130.0, 129.4, 128.8, 125.4, 125.23, 125.19, 121.5, 116.3, 114.1, 82.8, 82.2, 64.2, 53.0, 37.8, 28.1.

HRMS ($C_{47}H_{40}N_4O_{17}$): m/z (positive mode)=933.2462 (found [M+H]$^+$), 933.2461 (calc.).

Compound 7. To a solution of compound 6 (40 mg, 42.9 μmol) in THF (400 μL) and methanol (200 μL), a solution of LiOH·$H_2O$ (5.4 mg, 129 μmol, 3 eq) in water (85 μL) was added, and the resulting mixture was stirred vigorously at rt for 1 h. Acetic acid (200 μL) was then added, the reaction mixture was evaporated to dryness and dried in vacuo. The product was isolated by preparative HPLC (column: Thermo Scientific 250×21.2 mm 5 μm Hypersil Gold C18; gradient 40/60→90/10 A:B, A=0.1% v/v $HCO_2H$ in acetonitrile, B=0.1% v/v $HCO_2H$ in water; detection at 220 nm), fractions containing the product were evaporated (bath temperature 30° C.), and the residue was freeze-dried from aq. dioxane to give 7 as yellowish solid (33 mg, 85%).

$^1$H NMR (400 MHZ, acetone-$d_6$): δ 8.31 (dd, J=8.0, 1.3 Hz, 1H), 8.27 (br.s, 2H), 8.20 (d, J=8.3 Hz, 2H), 8.16 (dd, J=8.3, 1.6 Hz, 2H), 8.13 (dd, J=8.0, 0.8 Hz, 1H), 7.96 (dd, J=1.3, 0.8 Hz, 1H), 7.48 (d, J=2.2 Hz, 2H), 7.23 (dd, J=8.6, 2.2 Hz, 2H), 6.95 (d, J=8.6 Hz, 2H), 5.67-5.53 (m, 4H), 3.42 (s, 6H), 1.51 (s, 9H).

$^{13}$C NMR (101 MHz, acetone-$d_6$): δ 168.5, 165.8, 164.8, 154.9, 153.7, 152.2, 151.0, 146.4, 139.4, 135.8, 133.7, 132.0, 131.1, 130.8, 130.5, 129.4, 126.00, 125.98, 125.8, 122.2, 117.0, 114.6, 83.0, 82.7, 64.6, 37.7, 28.1.

HRMS ($C_{45}H_{36}N_4O_{17}$): m/z (positive mode)=905.2150 (found [M+H]$^+$), 905.2148 (calc.).

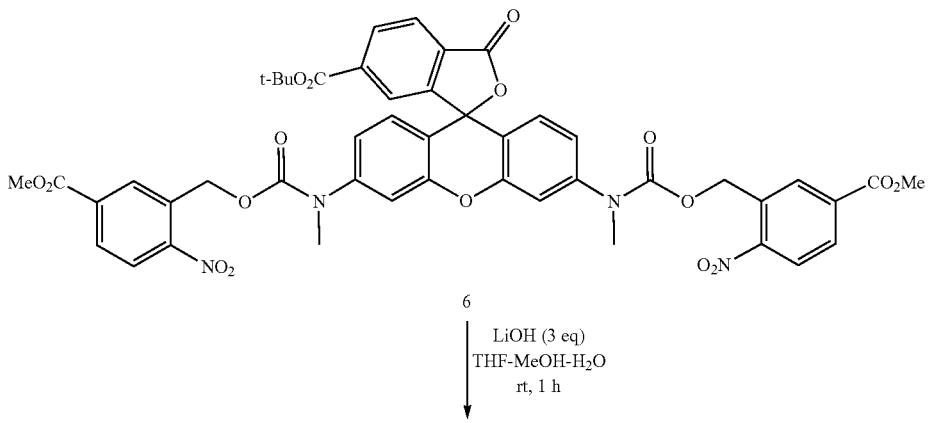

6

LiOH (3 eq)
THF-MeOH-$H_2O$
rt, 1 h

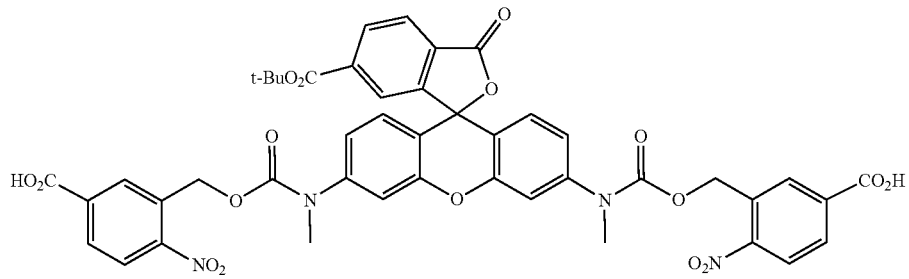

7

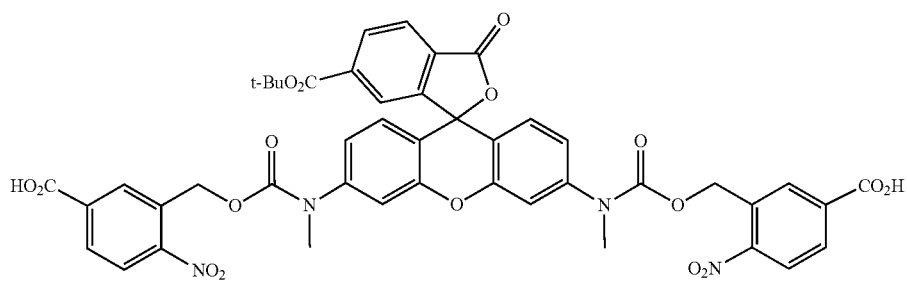

7

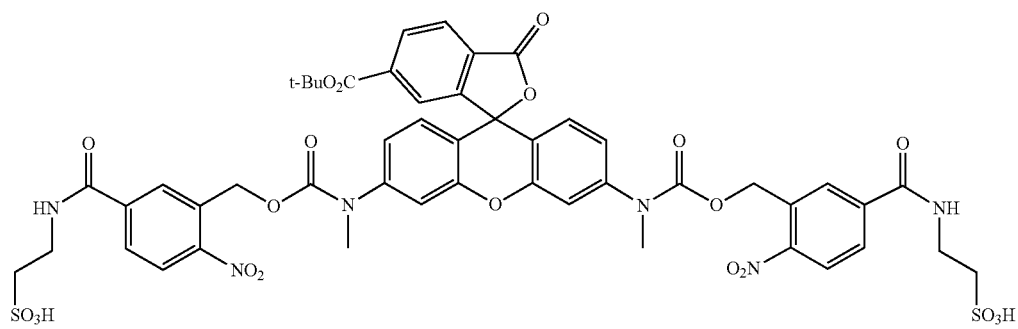

8

Compound 8. To a solution of compound 7 (28 mg, 30.9 µmol) in DMF (500 µL) and water (100 µL), taurine (27 mg, 216 µmol, 7 eq) and N,N-ethyldiisopropylamine (DIEA; 300 µL) were added followed by HATU (59 mg, 155 µmol, 5 eq; dissolved in 200 µL DMF). The resulting mixture was stirred vigorously at rt overnight (16 h). It was then evaporated to dryness and dried in vacuo. The product was isolated by preparative HPLC (column: Interchim 250×21.2 mm 5 µm Uptisphere Strategy PhC4; gradient 20/80→70/30 A:B, A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 8 as light orange solid (29 mg), which was used directly in the next step.

HRMS (C$_{49}$H$_{46}$N$_6$O$_{21}$S$_2$): m/z (positive mode)= 1119.2229 (found [M+H]$^+$), 1119.2230

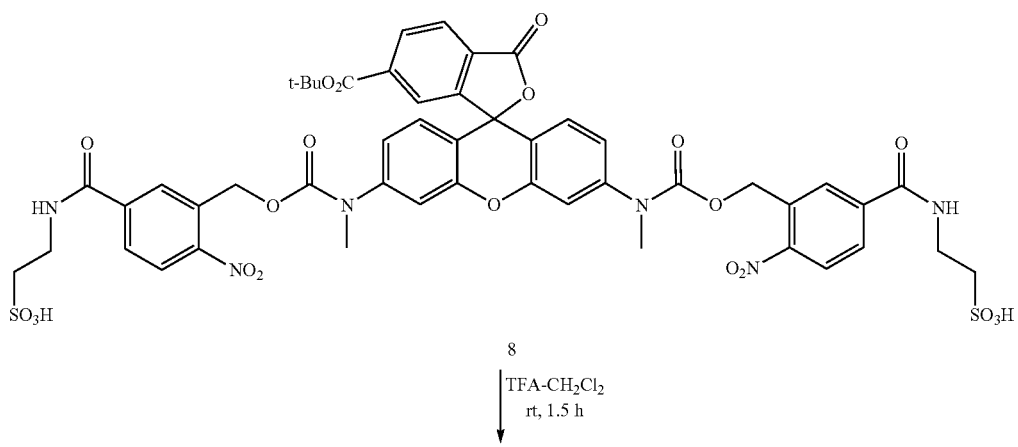

8

TFA-CH$_2$Cl$_2$
rt, 1.5 h

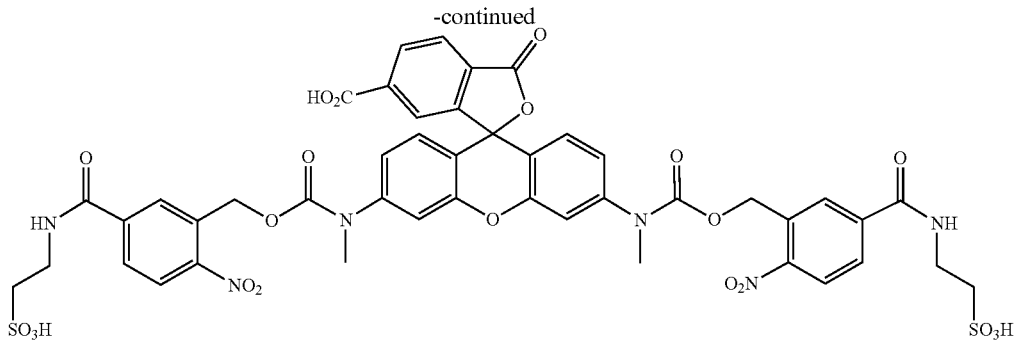

9

Compound 9. A solution of compound 8 (28 mg, 25.0 µmol) in CH$_2$Cl$_2$ (600 µL) and TFA (300 µL) was stirred at rt for 1.5 h. The resulting mixture was diluted with CH$_2$Cl$_2$ and toluene, evaporated to dryness and dried in vacuo. The product was isolated by preparative HPLC (column: Interchim 250×21.2 mm 5 µm Uptisphere Strategy PhC4; gradient 20/80→60/40 A:B, A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 9 as light orange solid (15 mg, 46% over 2 steps).

$^1$H NMR (400 MHZ, DMSO-d$_6$): δ 8.81 (t, J=5.3 Hz, 2H), 8.27 (dd, J=7.9, 1.3 Hz, 1H), 8.21-8.14 (m, 3H), 8.03 (br.s, 2H), 7.92 (dd, J=8.5, 1.9 Hz, 2H), 7.87 (t, J=1.0 Hz, 1H), 7.48 (d, J=2.2 Hz, 2H), 7.19 (dd, J=8.6, 2.2 Hz, 2H), 6.88 (d, J=8.6 Hz, 2H), 5.54-5.44 (m, 4H), 3.51 (q, J=6.8 Hz, 4H), 3.34 (s, 6H), 2.78-2.67 (t, J=6.8 Hz, 4H).

$^{13}$C NMR (101 MHZ, DMSO-d$_6$): δ 167.7, 166.0, 163.8, 153.9, 152.4, 150.7, 148.6, 145.0, 138.9, 137.6, 132.1, 131.3, 129.0, 128.4, 128.2, 127.4, 125.6, 125.2, 124.8, 121.5, 115.4, 113.3, 81.7, 63.8, 50.0, 37.1, 36.3.

HRMS (C$_{45}$H$_{38}$N$_6$O$_{21}$S$_2$): m/z (positive mode)= 1063.1604 (found [M+H]$^+$), 1063.1604 (calc.).

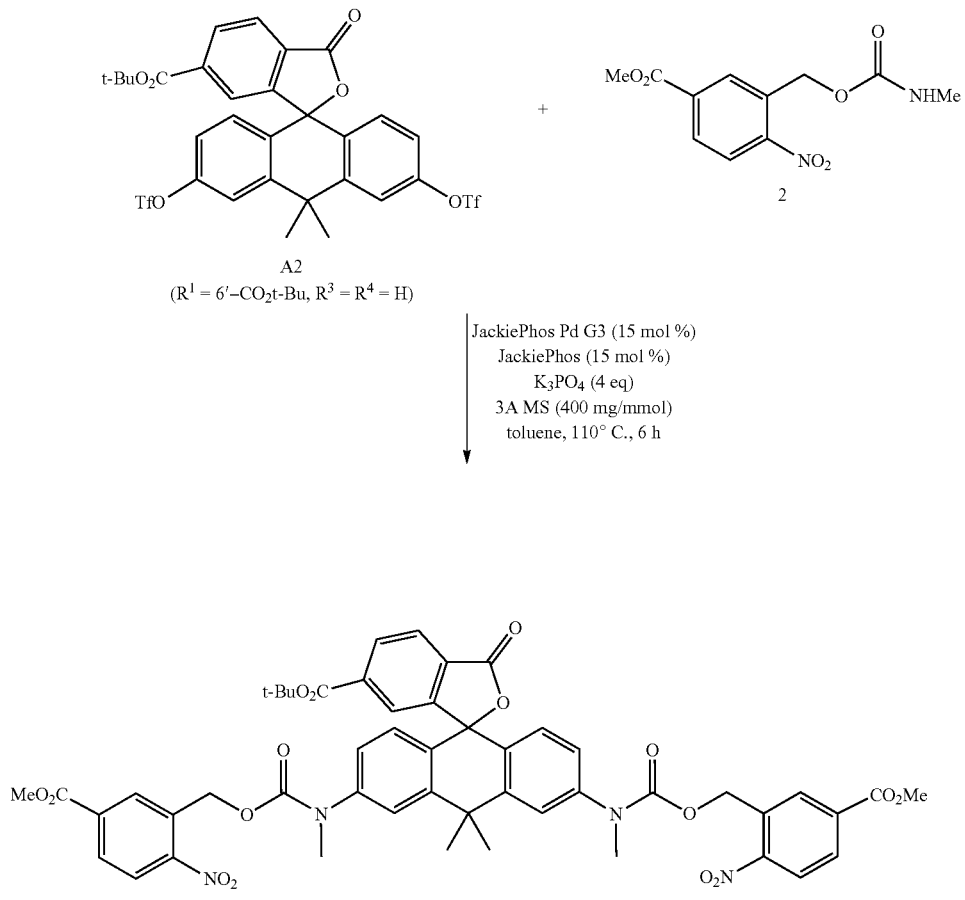

10

Compound 10. In a flame-dried 10 ml tube, loaded with anhydrous $K_3PO_4$ (119 mg, 0.56 mmol, 4 eq) and 3 Å molecular sieves (56 mg), compound A2 [Butkevich et al. Angew. Chem. Int. Ed. 2016, 55, 3290-3294] (108 mg, 0.14 mmol), compound 2 (90 mg, 0.34 mmol, 2.4 eq), JackiePhos Pd G3 precatalyst (24.5 mg, 0.021 mmol, 15 mol %) and JackiePhos ligand (16.7 mg, 0.021 mmol, 15 mol %) were loaded. The tube was sealed, anhydrous toluene (1.4 mL) was injected, the mixture was degassed on a Schlenk line and stirred at 110° C. for 6 h. It was then diluted with $CH_2Cl_2$, filtered through a plug of Celite (washing with $CH_2Cl_2$ and EtOAc-$CH_2Cl_2$), the filtrate was evaporated on Celite and the product was isolated by flash chromatography on Biotage Isolera system (25 g Interchim SiHP 30 μm cartridge, gradient 20% to 80% EtOAc/hexane) and freeze-dried from dioxane to yield 89 mg (66%) of 10 as white solid.

$^1$H NMR (400 MHZ, $CDCl_3$): δ 8.20 (dd, J=8.0, 1.3 Hz, 1H), 8.17 (br.s, 2H), 8.10-8.05 (m, 5H), 7.68 (br.s, 1H), 7.60 (br.s, 2H), 7.09 (dd, J=8.5, 2.2 Hz, 2H), 6.78 (d, J=8.5 Hz, 2H), 5.62-5.50 (m, 4H), 3.92 (s, 6H), 3.38 (s, 6H), 1.83 (s, 3H), 1.73 (s, 3H), 1.53 (s, 9H). $^{13}$C NMR (101 MHz, $CDCl_3$): δ 169.6, 165.0, 164.3, 154.9, 154.7, 150.1, 146.0, 143.9, 138.3, 134.6, 133.0, 130.7, 130.5, 129.9, 129.2, 128.8, 125.3, 125.2, 125.1, 124.2, 85.7, 82.7, 64.1, 53.0, 38.5, 38.0, 34.8, 33.3, 28.1.

HRMS ($C_{50}H_{46}N_4O_{16}$): m/z (positive mode)=959.2976 (found [M+H]$^+$), 959.2982 (calc.).

Compound 11. To a solution of compound 10 (40 mg, 41.7 μmol) in THF (400 μL) and methanol (200 μL), a solution of LiOH·$H_2O$ (5.3 mg, 125 μmol, 3 eq) in water (85 μL) was added, and the resulting mixture was stirred vigorously at rt for 1 h. Acetic acid (200 μL) was then added, the reaction mixture was evaporated to dryness and dried in vacuo. The product was isolated by preparative HPLC (column: Thermo Scientific 250×21.2 mm 5 μm Hypersil Gold C18; gradient 40/60→90/10 A:B, A=0.1% v/v $HCO_2H$ in acetonitrile, B=0.1% v/v $HCO_2H$ in water; detection at 220 nm), fractions containing the product were evaporated (bath temperature 30° C.), and the residue was freeze-dried from aq. dioxane to give 11 as light pink solid (33 mg, 85%).

$^1$H NMR (400 MHZ, acetone-$d_6$): δ 8.25 (dd, J=8.0, 1.3 Hz, 1H), 8.25 (br.s, 2H), 8.21-8.15 (m, 4H), 8.12 (dd, J=8.0, 0.8 Hz, 1H), 7.87 (d, J=2.2 Hz, 2H), 7.67 (dd, J=1.3, 0.8 Hz, 1H), 7.26 (dd, J=8.6, 2.2 Hz, 2H), 6.87 (d, J=8.6 Hz, 2H), 5.56 (s, 4H), 3.39 (s, 6H), 1.87 (s, 3H), 1.76 (s, 3H), 1.50 (s, 9H). $^{13}$C NMR (101 MHZ, acetone-$d_6$): δ 169.6, 165.9, 164.7, 156.1, 155.1, 151.2, 146.6, 145.1, 139.1, 135.8, 133.8, 131.4, 131.2, 130.8, 130.0, 129.3, 129.1, 126.2, 126.0, 125.3, 125.2, 125.1, 85.9, 83.0, 64.4, 39.1, 37.9, 34.6, 33.8, 28.1.

HRMS ($C_{48}H_{42}N_4O_{16}$): m/z (positive mode)=931.2661 (found [M+H]$^+$), 931.2669 (calc.).

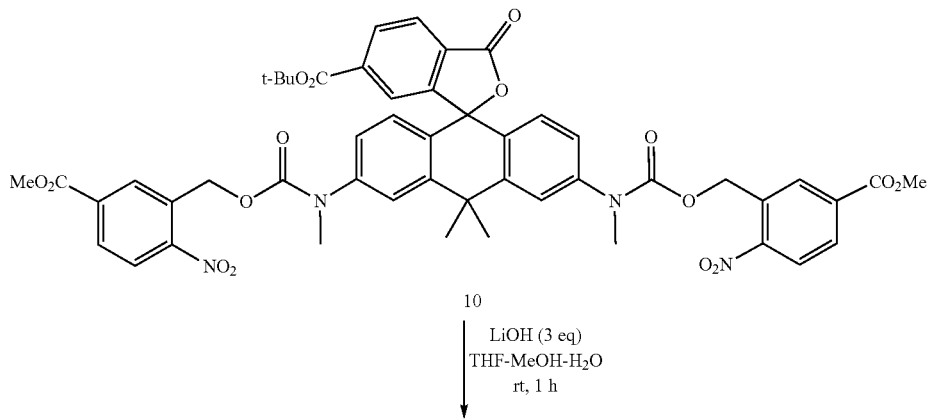

10

LiOH (3 eq)
THF-MeOH-$H_2O$
rt, 1 h

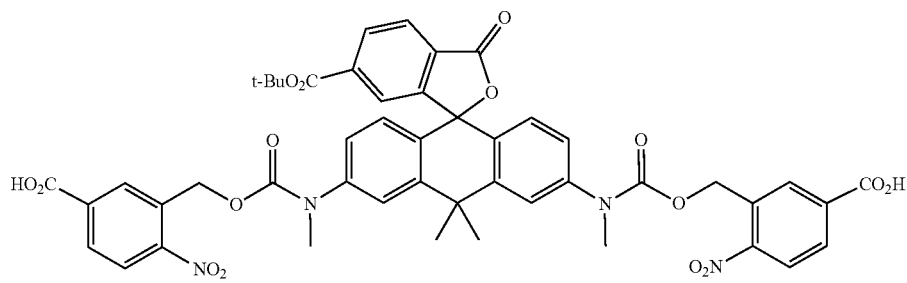

11

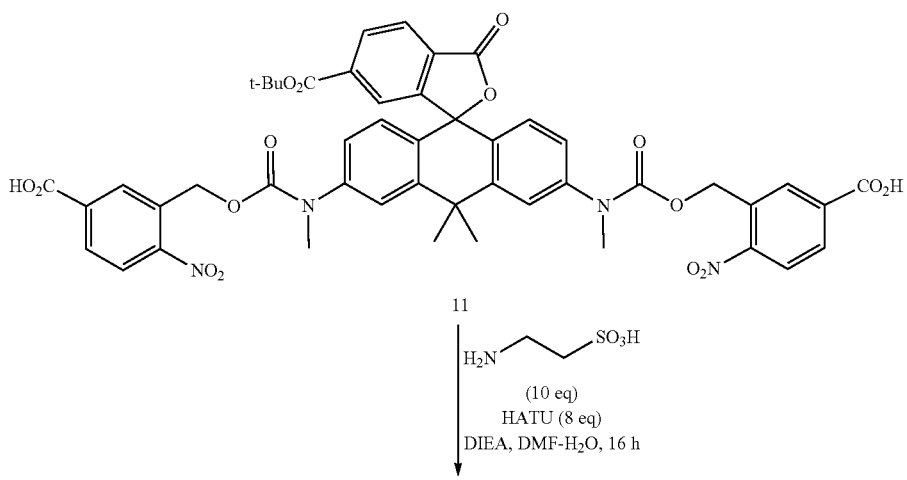

11

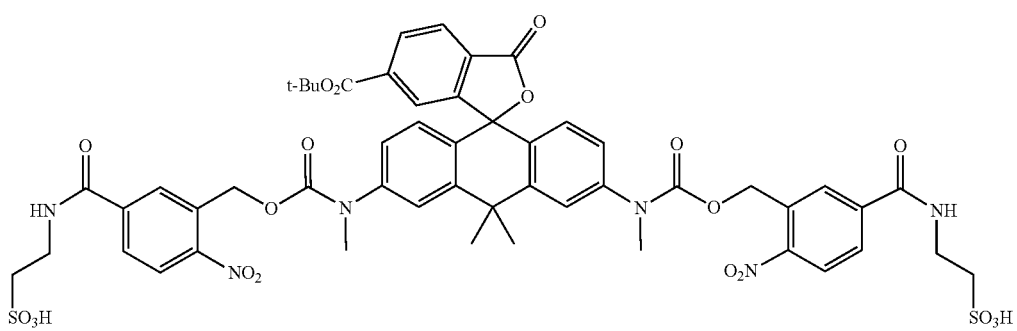

12

Compound 12. To a solution of compound 11 (30 mg, 32.2 μmol) in DMF (500 μL) and water (100 μL), taurine (40 mg, 322 μmol, 10 eq) and N,N-ethyldiisopropylamine (DIEA; 350 μL) were added followed by HATU (98 mg, 258 μmol, 8 eq; dissolved in 300 μL DMF). The resulting mixture was stirred vigorously at rt overnight (16 h). It was then evaporated to dryness and dried in vacuo. The product was isolated by preparative HPLC (column: Interchim 250× 21.2 mm 5 μm Uptisphere Strategy PhC4; gradient 20/80→70/30 A:B, A=0.1% v/v $HCO_2H$ in acetonitrile, B=0.1% v/v $HCO_2H$ in water; detection at 220 nm), fractions containing the product were evaporated (bath temperature 30° C.), and the residue was freeze-dried from aq. dioxane to give 8 as light pink solid (24 mg, 65%). 1H NMR (400 MHZ, $CD_3OD$): δ 8.23 (dd, J=8.0, 1.3 Hz, 1H), 8.14-8.07 (m, 3H), 8.04 (br.s, 2H), 7.92 (br.d, J=8.5 Hz, 2H), 7.76 (br.s, 2H), 7.60 (s, 1H), 7.18 (dd, J=8.6, 2.1 Hz, 2H), 6.81 (d, J=8.6 Hz, 2H), 5.52 (s, 4H), 3.79 (t, J=6.7 Hz, 4H), 3.70 (hept, J=6.6 Hz, DIEA-$H^+$), 3.37 (s, 6H), 3.20 (q, J=7.4 Hz, DIEA-$H^+$), 3.11 (t, J=6.7 Hz, 4H), 1.80 (s, 3H), 1.70 (s, 3H), 1.49 (s, 9H), 1.37-1.32 (m, DIEA-$H^+$).

$^{13}C$ NMR (101 MHZ, $CD_3OD$): δ 171.1, 167.4, 165.3, 156.6, 156.4, 150.6, 147.2, 145.3, 140.2, 139.6, 133.9, 131.8, 130.1, 129.9, 129.7, 129.4, 128.7, 126.4, 126.2, 125.8, 125.5, 86.9, 83.6, 65.4, 55.8, 51.1, 43.8, 39.5, 38.2, 37.4, 34.8, 33.8, 28.2, 18.7, 17.3, 13.2 (including the signals of DIEA-$H^+$ counterion).

HRMS ($C_{52}H_{52}N_6O_{20}S_2$): m/z (positive mode)= 1145.2753 (found [M+H]$^+$), 1145.2751

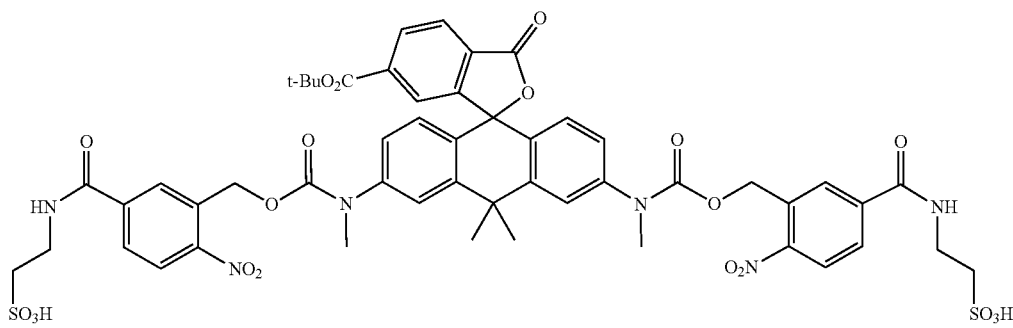

12

TFA-CH₂Cl₂
rt, 1.5 h

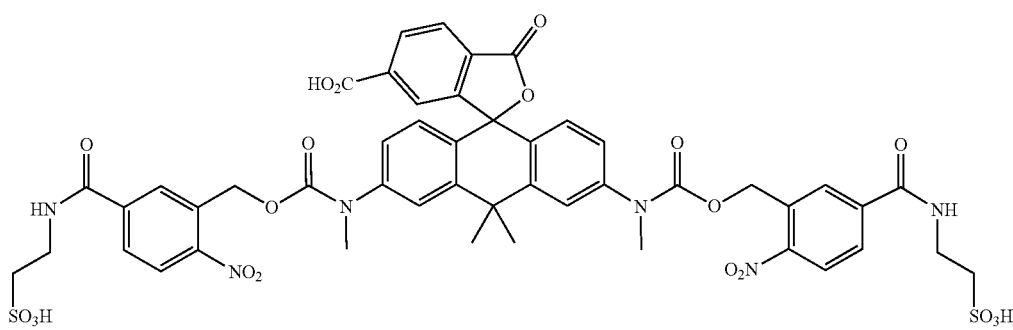

13

Compound 13. A solution of compound 12 (24 mg, 21.0 µmol) in $CH_2Cl_2$ (600 µL) and TFA (300 µL) was stirred at rt for 1.5 h. The resulting mixture was diluted with $CH_2Cl_2$ and toluene, evaporated to dryness, the residue was redissolved in aq. dioxane and freeze-dried to give 13 as light pink solid (20 mg, 88%).

¹H NMR (400 MHZ, DMSO-$d_6$): δ 8.84 (t, J=5.4 Hz, 2H), 8.24-8.13 (m, 4H), 8.06 (s, 2H), 7.94 (d, J=8.5 Hz, 2H), 7.81 (d, J=2.2 Hz, 2H), 7.54 (s, 1H), 7.22 (dd, J=8.6, 2.1 Hz, 2H), 6.74 (d, J=8.6 Hz, 2H), 5.47 (s, 4H), 3.66-3.57 (m, DIEA-H⁺), 3.54 (t, J=7.1 Hz, 4H), 3.33 (s, 6H), 3.18-3.09 (m, DIEA-H⁺), 2.76 (t, J=7.1 Hz, 4H), 1.74 (s, 3H), 1.65 (s, 3H), 1.28-1.22 (m, DIEA-H⁺).

¹³C NMR (101 MHZ, DMSO-$d_6$): δ 168.7, 166.0, 163.8, 154.7, 154.0, 148.8, 145.4, 143.7, 138.9, 137.5, 132.1, 130.8, 128.5, 128.4, 127.9, 127.5, 127.4, 125.8, 125.1, 124.4, 123.9, 84.9, 63.7, 53.6, 50.0, 41.9, 37.9, 37.4, 36.4, 33.7, 33.2, 18.1, 16.7, 12.5 (including the signals of DIEA-H⁺ counterion).

HRMS ($C_{48}H_4N_6O_{20}S_2$): m/z (positive mode)= 1089.2129 (found [M+H]⁺), 1089.2125

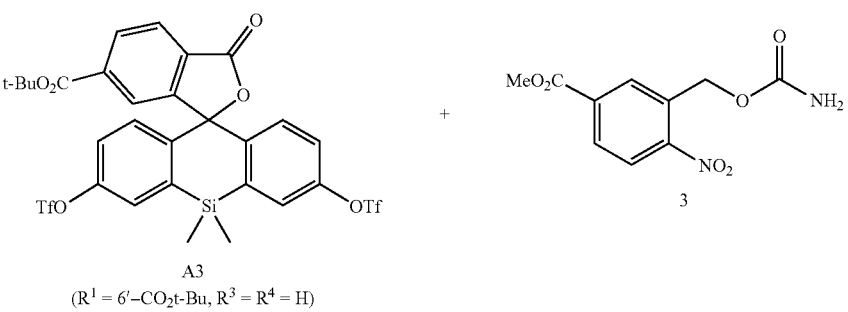

A3
($R^1$ = 6′-$CO_2$t-Bu, $R^3$ = $R^4$ = H)

JackiePhos Pd G3 (15 mol %)
JackiePhos (15 mol %)
$K_3PO_4$ (4 eq)
3A MS (400 mg/mmol)
toluene, 110° C., 6 h

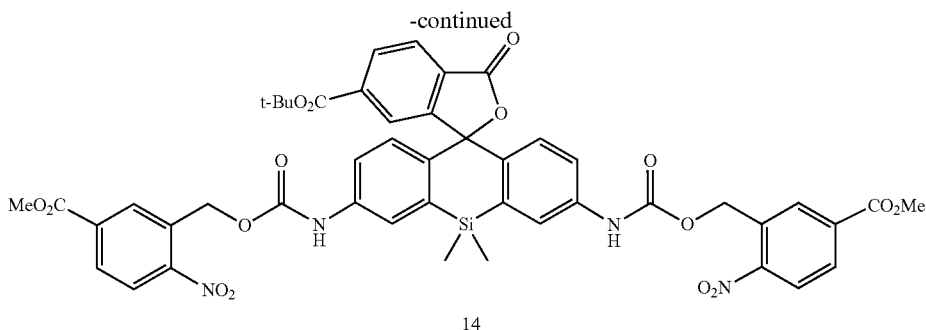

14

Compound 14. In a flame-dried 10 ml tube, loaded with anhydrous K₃PO₄ (115 mg, 0.54 mmol, 4 eq) and 3 Å molecular sieves (55 mg), compound A3 [Butkevich et al. Chem. Eur. J. 2017, 23, 12114-12119] (100 mg, 0.135 mmol), compound 3 (83 mg, 0.325 mmol, 2.4 eq), JackiePhos Pd G3 precatalyst (24 mg, 0.02 mmol, 15 mol %) and JackiePhos ligand (16 mg, 0.02 mmol, 15 mol %) were loaded. The tube was sealed, anhydrous toluene (1.4 mL) was injected, the mixture was degassed on a Schlenk line and stirred at 110° C. for 6 h. It was then diluted with CH₂Cl₂, filtered through a plug of Celite (washing with CH₂Cl₂ and EtOAc-CH₂Cl₂), the filtrate was evaporated on Celite and the product was isolated by flash chromatography on Biotage Isolera system (25 g Interchim SiHP 30 μm cartridge, gradient 10% to 80% EtOAc/hexane) and freeze-dried from dioxane to yield 85 mg (66%) of 14 as white solid.

$^1$H NMR (400 MHZ, CDCl₃): δ 8.30 (t, J=1.1 Hz, 2H), 8.15-8.09 (m, 5H), 7.99 (dd, J=8.0, 0.7 Hz, 1H), 7.80 (br.s, 2H), 7.76 (dd, J=1.3, 0.7 Hz, 1H), 7.30 (dd, J=8.8, 2.5 Hz, 2H), 7.14 (br.s, 2H), 7.07 (d, J=8.8 Hz, 2H), 5.60 (s, 4H), 3.95 (s, 6H), 1.53 (s, 9H), 0.70 (s, 3H), 0.58 (s, 3H).

$^{13}$C NMR (101 MHz, CDCl₃): δ 170.2, 165.1, 164.0, 155.2, 152.6, 150.0, 139.1, 137.8, 137.4, 135.9, 134.7, 132.7, 130.4, 130.1, 127.7, 127.4, 126.1, 125.3, 124.5, 123.7, 120.5, 89.8, 82.7, 63.4, 53.1, 28.2, −0.26, −0.34.

HRMS (C₄₇H₄₂N₄O₁₆Si): m/z (positive mode)=947.2438 (found [M+H]⁺), 947.2438 (calc.).

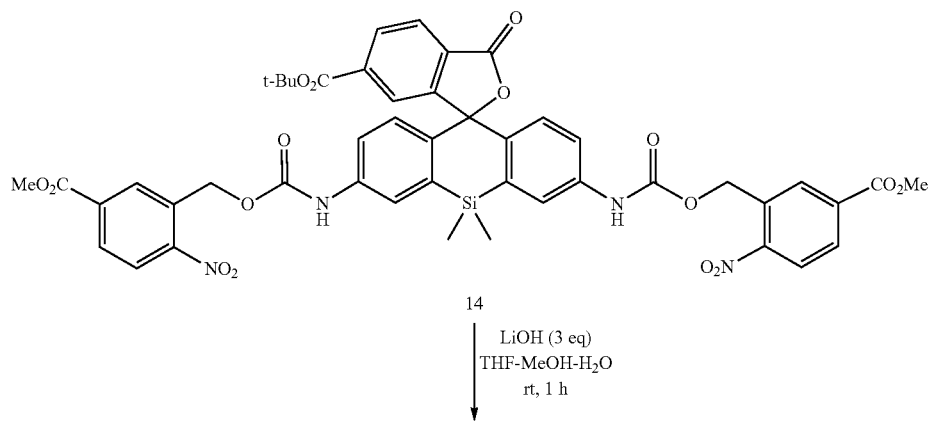

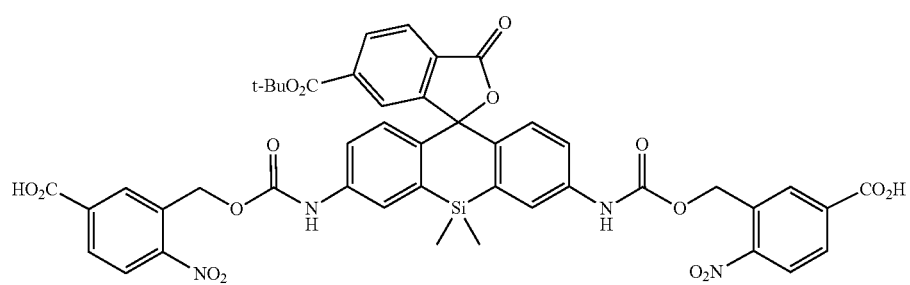

15

Compound 15. To a solution of compound 14 (40 mg, 42.2 µmol) in THF (400 µL) and methanol (200 µL), a solution of LiOH·H$_2$O (5.3 mg, 127 µmol, 3 eq) in water (85 µL) was added, and the resulting mixture was stirred vigorously at rt for 1 h. Acetic acid (200 µL) was then added, the reaction mixture was evaporated to dryness and dried in vacuo. The product was isolated by preparative HPLC (column: Thermo Scientific 250×21.2 mm 5 µm Hypersil Gold C18; gradient 40/60→90/10 A:B, A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 15 as white solid (30 mg, 77%).

$^1$H NMR (400 MHZ, acetone-d$_6$): δ 9.29 (br.s, 2H), 8.39 (dd, J=1.8, 0.8 Hz, 2H), 8.25 (d, J=8.3 Hz, 2H), 8.21 (dd, J=8.3, 2.0 Hz, 2H), 8.17 (dd, J=8.0, 1.3 Hz, 1H), 8.09-8.02 (m, 3H), 7.81 (d, J=0.6 Hz, 1H), 7.57 (dd, J=8.8, 2.5 Hz, 2H), 7.12 (d, J=8.8 Hz, 2H), 5.63 (s, 4H), 1.53 (s, 9H), 0.75 (s, 3H), 0.61 (s, 3H).

$^{13}$C NMR (101 MHZ, acetone-d$_6$): δ 170.1, 165.9, 164.5, 156.4, 153.8, 151.0, 139.7, 139.3, 138.5, 136.01, 135.95, 133.8, 131.03, 131.01, 130.9, 128.5, 128.0, 126.8, 126.1, 124.9, 124.2, 121.1, 90.1, 82.9, 63.5, 28.1, −0.2, −0.3.

HRMS (C$_{45}$H$_{38}$N$_4$O$_{16}$Si): m/z (positive mode)=919.2124 (found [M+H]$^+$), 919.2125 (calc.).

Compound 16. To a solution of compound 15 (28 mg, 30.5 µmol) in DMF (500 µL) and water (150 µL), taurine (38 mg, 306 µmol, 10 eq) and N,N-ethyldiisopropylamine (DIEA; 350 µL) were added followed by HATU (92 mg, 244 µmol, 8 eq; dissolved in 300 µL DMF). The resulting mixture was stirred vigorously at rt overnight (16 h). It was then evaporated to dryness and dried in vacuo. The product was isolated by preparative HPLC (column: Interchim 250× 21.2 mm 5 µm Uptisphere Strategy PhC4; gradient 20/80→70/30 A:B, A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 16 as pale violet solid (15.5 mg, 45%). 1H NMR (400 MHZ, CD$_3$OD): δ 8.26 (br.s, 2H), 8.19 (d, J=8.5 Hz, 2H), 8.15 (dd, J=8.1, 1.3 Hz, 1H), 8.02 (dd, J=8.1, 0.7 Hz, 1H), 7.95 (dd, J=8.4, 1.8 Hz, 2H), 7.92 (d, J=2.3 Hz, 2H), 7.74 (app.t, J=1.0 Hz, 1H), 7.49 (dd, J=8.8, 2.4 Hz, 2H), 7.00 (d, J=8.8 Hz, 2H), 5.58 (s, 4H), 3.82 (br.t, J=6.4 Hz, 4H), 3.70 (hept, J=6.6 Hz, DIEA-H$^+$), 3.18 (q, J=7.4 Hz, DIEA-H$^+$), 3.13 (br.t, J=6.4 Hz, 4H), 1.53 (s, 9H), 1.36-1.30 (m, DIEA-H$^+$), 0.73 (s, 3H), 0.62 (s, 3H).

$^{13}$C NMR (101 MHZ, CD$_3$OD): δ 171.61, 167.58, 165.2, 157.0, 154.9, 150.2, 140.5, 140.0, 139.4, 139.0, 136.7, 134.4, 131.3, 129.1, 128.9, 128.6, 128.0, 127.0, 126.3, 125.3, 124.7, 121.4, 91.3, 83.7, 64.1, 55.8, 51.1, 43.8, 37.4, 28.3, 18.7, 17.3, 13.2, −0.25, −0.27 (including the signals of DIEA-H$^+$ counterion).

HRMS (C$_{49}$H$_{48}$N$_6$O$_{20}$S$_2$Si): m/z (positive mode)= 1133.2208 (found [M+H]$^+$), 1133.2207 (calc.).

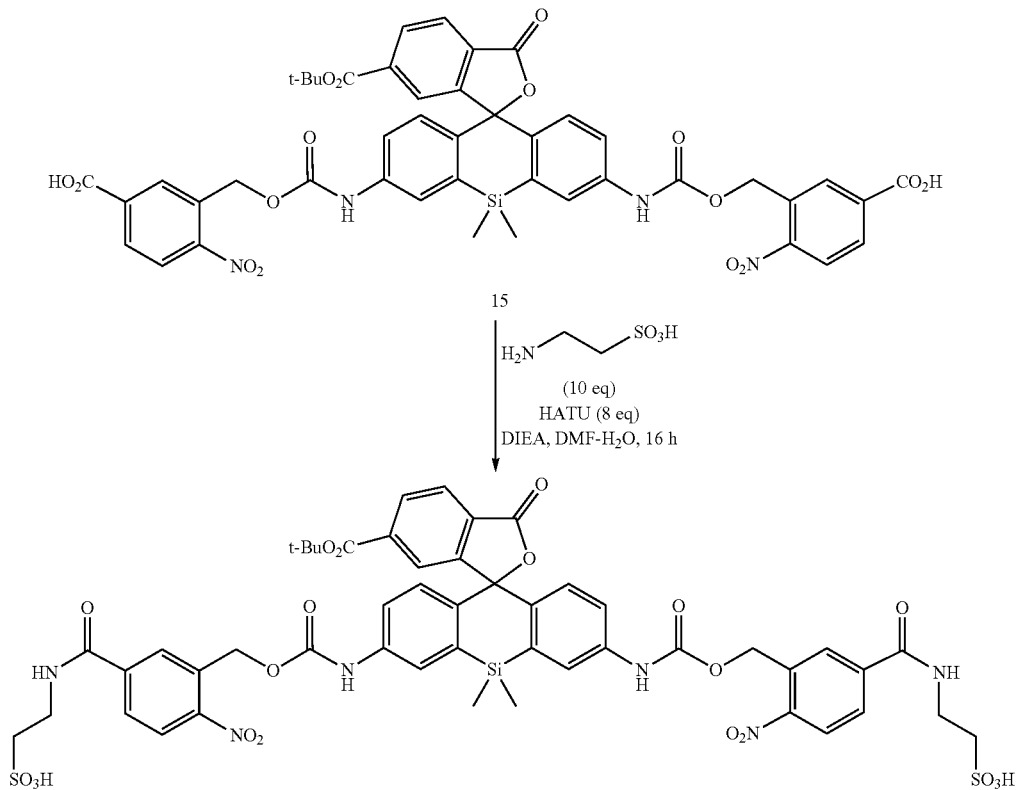

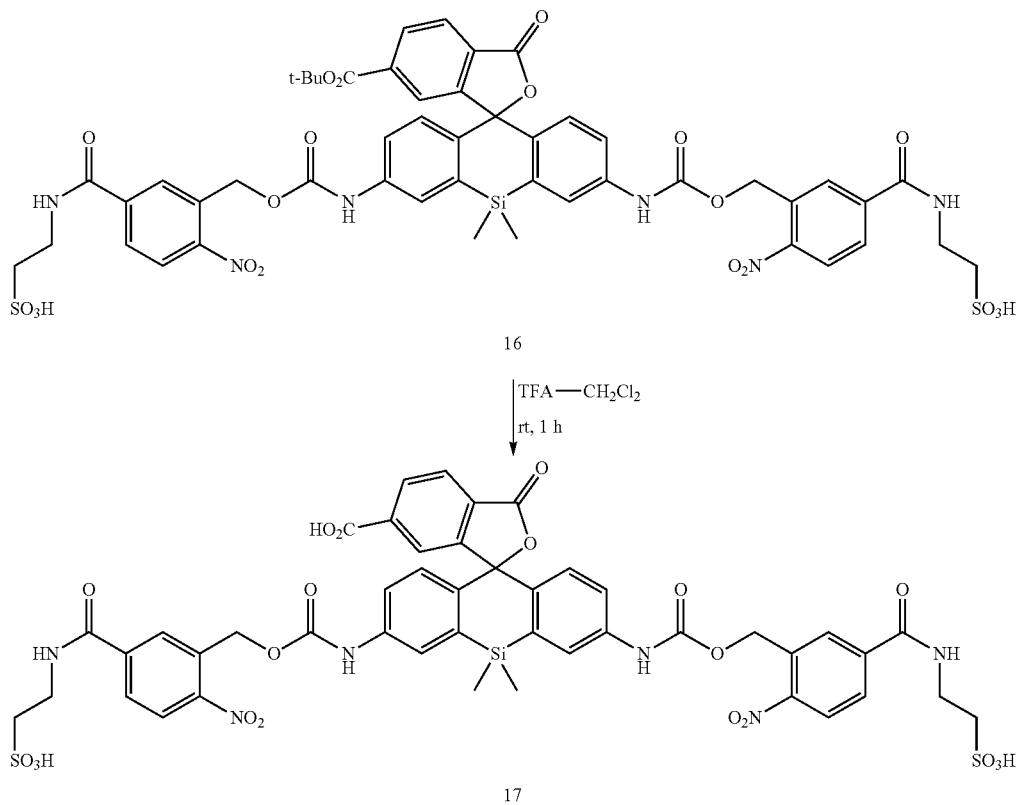

Compound 17. A solution of compound 16 (15 mg, 13.3 μmol) in CH$_2$Cl$_2$ (600 μL) and TFA (300 μL) was stirred at rt for 1 h. The resulting mixture was diluted with CH$_2$Cl$_2$ and toluene, evaporated to dryness and dried in vacuo. The product was isolated by preparative HPLC (column: Interchim 250×21.2 mm 5 μm Uptisphere Strategy PhC4; gradient 20/80→60/40 A:B, A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 17 as light violet solid (9.3 mg, 65%).

$^1$H NMR (400 MHZ, DMSO-d$_6$): δ 10.08 (s, 2H), 8.84 (t, J=5.3 Hz, 2H), 8.28-8.20 (m, 4H), 8.14 (dd, J=8.0, 1.3 Hz, 1H), 8.09 (d, J=7.7 Hz, 1H), 8.01-7.92 (m, 4H), 7.72 (s, 1H), 7.52 (dd, J=8.8, 2.4 Hz, 2H), 6.99 (d, J=8.8 Hz, 2H), 5.53 (s, 4H), 3.57 (q, J=6.9 Hz, 4H), 2.76 (t, J=6.9 Hz, 4H), 0.66 (s, 3H), 0.56 (s, 3H).

$^{13}$C NMR (101 MHZ, DMSO-d$_6$): δ 169.1, 165.9, 164.0, 154.7, 152.8, 148.4, 139.2, 138.7, 137.4, 136.8, 134.9, 132.5, 130.4, 128.3, 127.4, 127.2, 126.9, 126.4, 125.3, 124.0, 123.3, 120.1, 89.2, 62.6, 50.0, 36.4, −0.5, −0.9.

HRMS (C$_{45}$H$_{40}$N$_6$O$_{20}$S$_2$Si): m/z (positive mode)= 1077.1583 (found [M+H]$^+$), 1077.1581 (calc.).

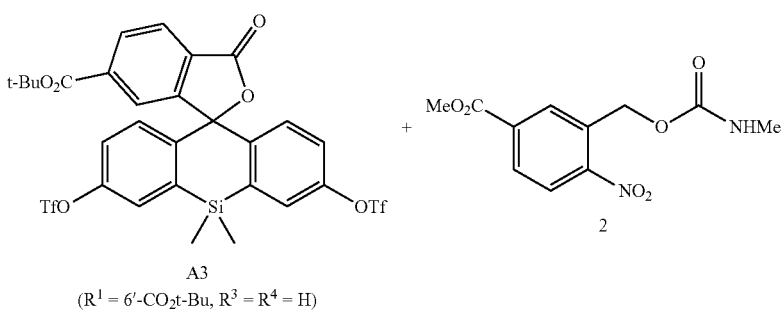

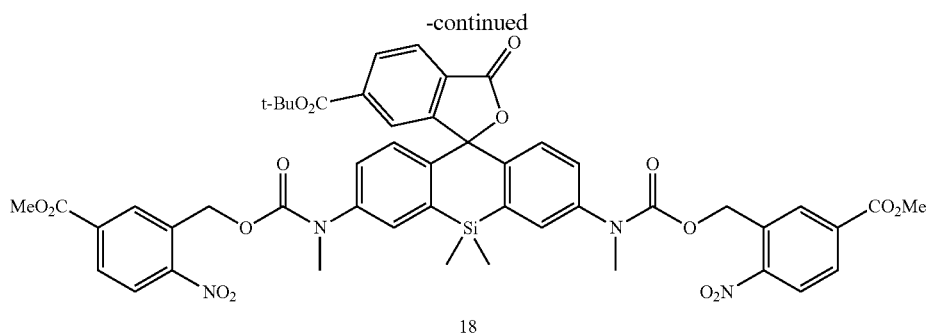

18

Compound 18. In a flame-dried 10 ml tube, loaded with anhydrous $K_3PO_4$ (115 mg, 0.54 mmol, 4 eq) and 3 Å molecular sieves (55 mg), compound A3 [Butkevich et al. Chem. Eur. J. 2017, 23, 12114-12119] (100 mg, 0.135 mmol), compound 2 (87 mg, 0.325 mmol, 2.4 eq), Jackie-Phos Pd G3 precatalyst (24 mg, 0.02 mmol, 15 mol %) and JackiePhos ligand (16 mg, 0.02 mmol, 15 mol %) were loaded. The tube was sealed, anhydrous toluene (1.4 mL) was injected, the mixture was degassed on a Schlenk line and stirred at 110° C. for 6 h. It was then diluted with $CH_2Cl_2$, filtered through a plug of Celite (washing with $CH_2Cl_2$ and EtOAc-$CH_2Cl_2$), the filtrate was evaporated on Celite and the product was isolated by flash chromatography on Biotage Isolera system (25 g Interchim SiHP 30 μm cartridge, gradient 20% to 80% EtOAc/hexane) and freeze-dried from dioxane to yield 68 mg (52%) of 18 as white solid.

$^1$H NMR (400 MHz, CDCl$_3$): δ 8.20-8.05 (m, 7H), 8.01 (dd, J=8.1, 0.7 Hz, 1H), 7.91 (br.s, 1H), 7.62 (d, J=2.4 Hz, 2H), 7.23 (dd, J=8.6, 2.4 Hz, 2H), 7.16 (d, J=8.6 Hz, 2H), 5.54 (s, 4H), 3.91 (s, 6H), 3.36 (s, 6H), 1.55 (s, 9H), 0.72 (s, 3H), 0.59 (s, 3H).

$^{13}$C NMR (101 MHz, CDCl$_3$): δ 169.8, 165.0, 164.1, 154.6, 154.2, 150.1, 142.7, 141.8, 137.7, 136.2, 134.6, 132.9, 131.0, 130.6, 129.9, 128.1, 127.4, 127.2, 126.2, 125.2, 125.1, 89.7, 82.7, 64.1, 53.0, 37.9, 28.2, −0.1, −0.6.

HRMS (C$_{49}$H$_{46}$N$_4$O$_{16}$Si): m/z (positive mode)=975.2741 (found [M+H]$^+$), 975.2751 (calc.).

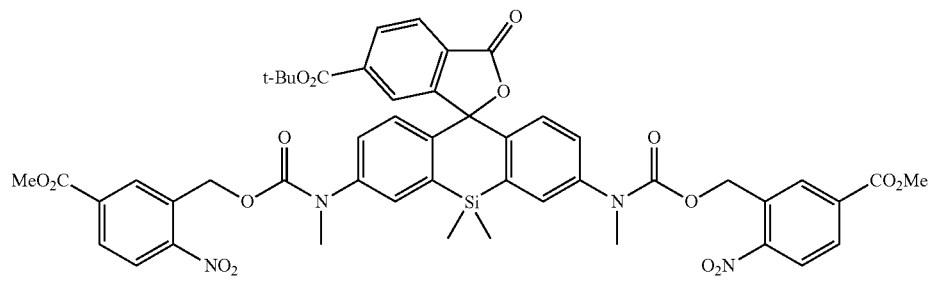

18

LiOH (3 eq)
THF—MeOH—H$_2$O
rt, 1 h

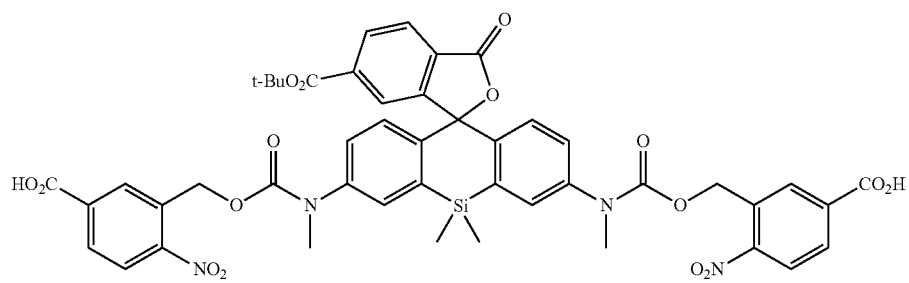

19

Compound 19. To a solution of compound 18 (20 mg, 20.5 µmol) in THF (200 µL) and methanol (100 µL), a solution of LiOH·H$_2$O (2.6 mg, 61.5 µmol, 3 eq) in water (40 µL) was added, and the resulting mixture was stirred vigorously at rt for 1 h. Acetic acid (100 µL) was then added, the reaction mixture was evaporated to dryness and dried in vacuo. The product was isolated by preparative HPLC (column: Thermo Scientific 250×21.2 mm 5 µm Hypersil Gold C18; gradient 40/60→90/10 A:B, A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 19 as white solid (14.5 mg, 75%).

$^1$H NMR (400 MHZ, acetone-d$_6$): δ 8.25 (br.s, 2H), 8.21-8.15 (m, 5H), 8.07 (dd, J=8.0, 0.7 Hz, 1H), 7.90 (dd, J=1.3, 0.7 Hz, 2H), 7.88 (d, J=2.4 Hz, 2H), 7.41 (dd, J=8.7, 2.4 Hz, 2H), 7.21 (d, J=8.7 Hz, 2H), 5.54 (s, 4H), 3.36 (s, 6H), 1.52 (s, 9H), 0.74 (s, 3H), 0.60 (s, 3H).

$^{13}$C NMR (101 MHZ, acetone-d$_6$): δ 169.9, 165.8, 164.6, 155.7, 155.1, 151.2, 143.9, 142.3, 138.6, 136.4, 135.8, 133.7, 131.8, 131.4, 131.3, 130.9, 128.5, 128.2, 127.8, 127.0, 126.0, 125.2, 89.9, 83.1, 64.4, 37.9, 28.1, −0.3, −0.4.

HRMS (C$_{47}$H$_{42}$N$_4$O$_{16}$Si): m/z (positive mode)=947.2429 (found [M+H]$^+$), 947.2438 (calc.).

Compound 20. To a solution of compound 19 (18.5 mg, 19.5 µmol) in DMF (300 µL) and water (100 µL), taurine (25 mg, 200 µmol, 10 eq) and N,N-ethyldiisopropylamine (DIEA; 100 µL) were added followed by HATU (45 mg, 117 µmol, 6 eq; dissolved in 150 µL DMF). The resulting mixture was stirred vigorously at rt overnight (16 h). It was then evaporated to dryness and dried in vacuo. The product was isolated by preparative HPLC (column: Interchim 250× 21.2 mm 5 µm Uptisphere Strategy PhC4; gradient 20/80→70/30 A:B, A=acetonitrile, B=50 mM ammonium formate in water, pH=3.5-4.0; detection at 220 nm), fractions containing the product were evaporated (bath temperature 30° C.), and the residue was freeze-dried from aq. dioxane to give 20 as pale violet solid (23.5 mg, remainder ammonium formate).

1H NMR (400 MHZ, CD$_3$OD): δ 8.43 (s, 1H), 8.14 (dd, J=8.0, 1.3 Hz, 1H), 8.12-7.99 (m, 5H), 7.92 (dd, J=8.4, 1.9 Hz, 2H), 7.77 (s, 3H), 7.32 (dd, J=8.7, 2.4 Hz, 2H), 7.17 (d, J=8.7 Hz, 2H), 5.49 (s, 4H), 3.79 (t, J=6.7 Hz, 4H), 3.34 (s, 6H), 3.10 (t, J=6.7 Hz, 4H), 1.50 (s, 9H), 0.70 (s, 3H), 0.56 (s, 3H).

$^{13}$C NMR (101 MHZ, CD$_3$OD): δ 171.4, 167.3, 165.2, 156.7, 156.4, 150.6, 144.1, 142.9, 140.2, 139.1, 136.7, 133.8, 132.5, 131.5, 129.8, 128.8, 128.4, 128.1, 127.2, 126.2, 125.3, 90.6, 83.7, 65.4, 51.1, 38.2, 37.4, 28.3, −0.1, −0.4.

HRMS (C$_{51}$H$_{52}$N$_6$O$_{20}$S$_2$Si): m/z (positive mode)= 1161.2518 (found [M+H]$^+$), 1161.2520 (calc.).

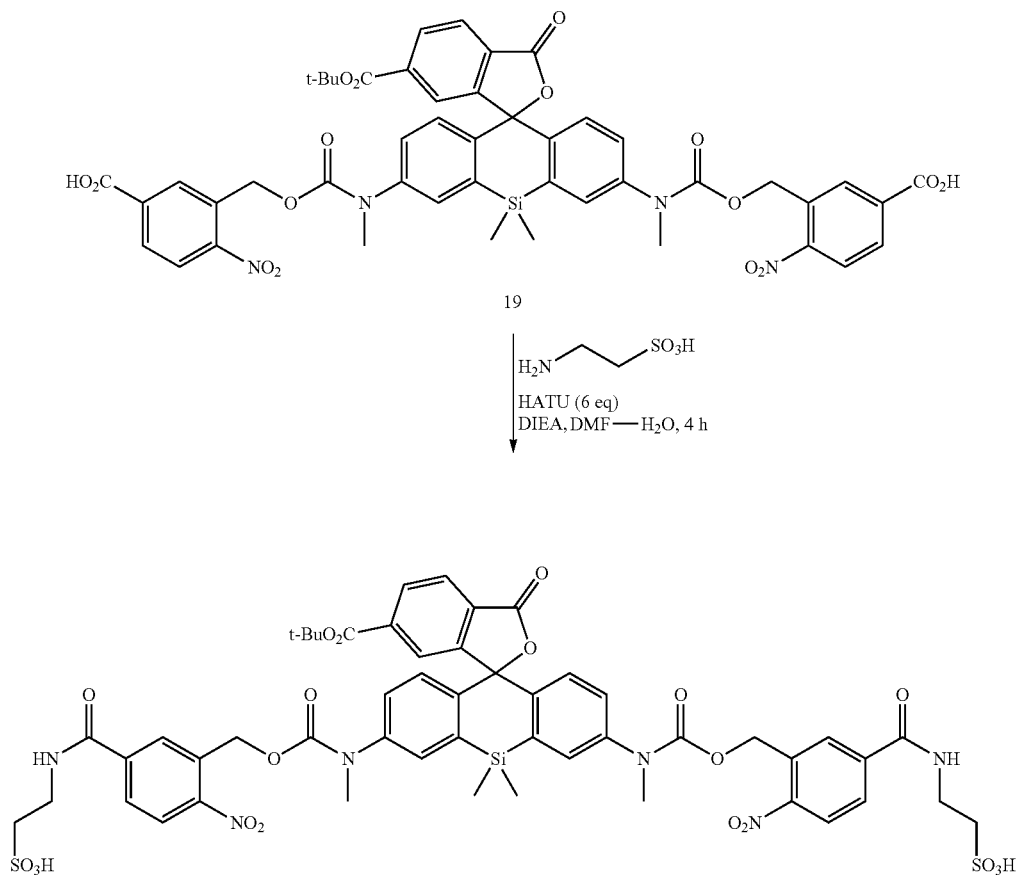

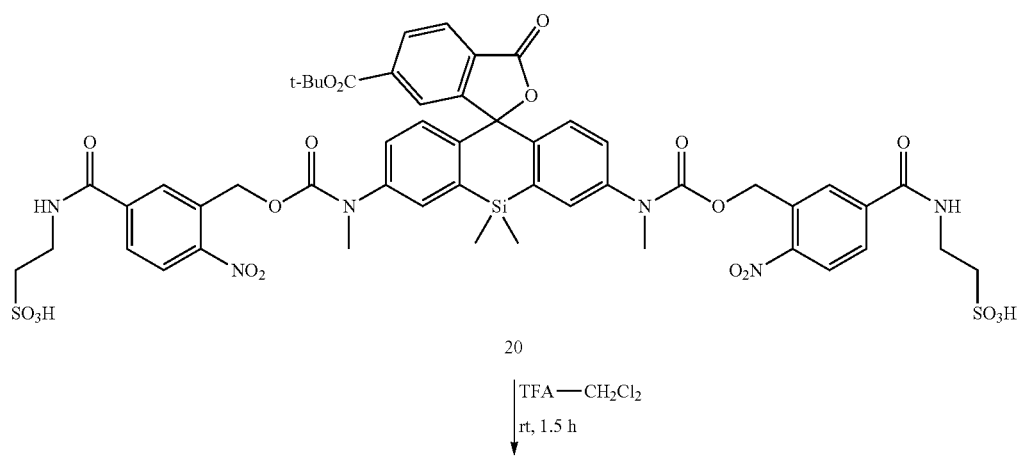

20

TFA—CH$_2$Cl$_2$
rt, 1.5 h

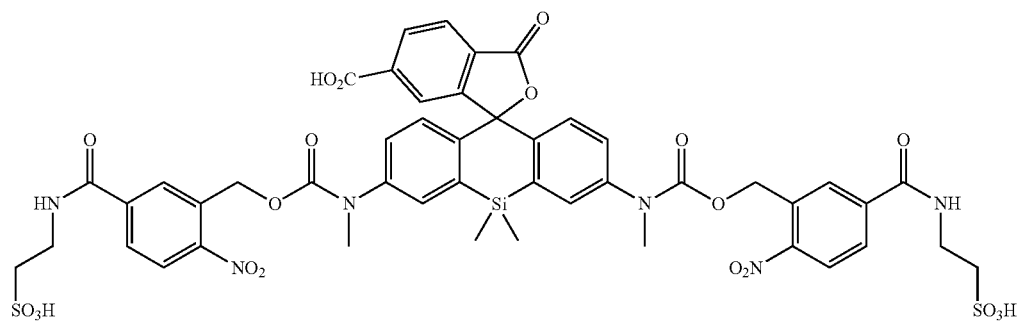

21

Compound 21. A solution of compound 20 (23.5 mg, 19.5 µmol) in CH$_2$Cl$_2$ (500 µL) and TFA (250 µL) was stirred at rt for 1.5 h. The resulting mixture was diluted with CH$_2$Cl$_2$ and toluene, evaporated to dryness; dissolved the residue in CH$_2$Cl$_2$ (3 mL) and N,N-ethyldiisopropylamine (DIEA; 200 µL), evaporated to dryness and dried in vacuo. The product was isolated by preparative HPLC (column: Interchim 250× 21.2 mm 5 µm Uptisphere Strategy PhC4; gradient 20/80→100/0 A:B, A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 21 as bluish solid (17.5 mg, 81% over 2 steps).

$^1$H NMR (400 MHZ, DMSO-d$_6$): δ 8.84 (t, J=5.3 Hz, 2H), 8.20-8.11 (m, 4H), 8.05 (br.s, 2H), 7.95 (dd, J=8.4, 1.9 Hz, 2H), 7.86-7.79 (m, 3H), 7.37 (dd, J=8.6, 2.5 Hz, 2H), 7.06 (d, J=8.6 Hz, 2H), 5.46 (s, 4H), 3.62-3.52 (m, 6H), 2.82-2.71 (m, 4H), 0.64 (s, 3H), 0.52 (s, 3H).

$^{13}$C NMR (101 MHZ, DMSO-d$_6$): δ 168.8, 165.9, 163.8, 154.0, 153.9, 148.7, 142.6, 140.6, 138.9, 136.9, 135.4, 132.0, 130.8, 130.7, 128.5, 127.5, 127.3, 127.2, 126.8, 126.6, 125.2, 124.3, 89.0, 63.7, 50.0, 37.3, 36.4, −0.6, −1.3.

HRMS (C$_{47}$H$_{44}$N$_6$O$_{20}$S$_2$Si): m/z (positive mode)= 1105.1897 (found [M+H]$^+$), 1105.1894 (calc.).

EXAMPLE 2

Synthesis of Photoactivatable Labels

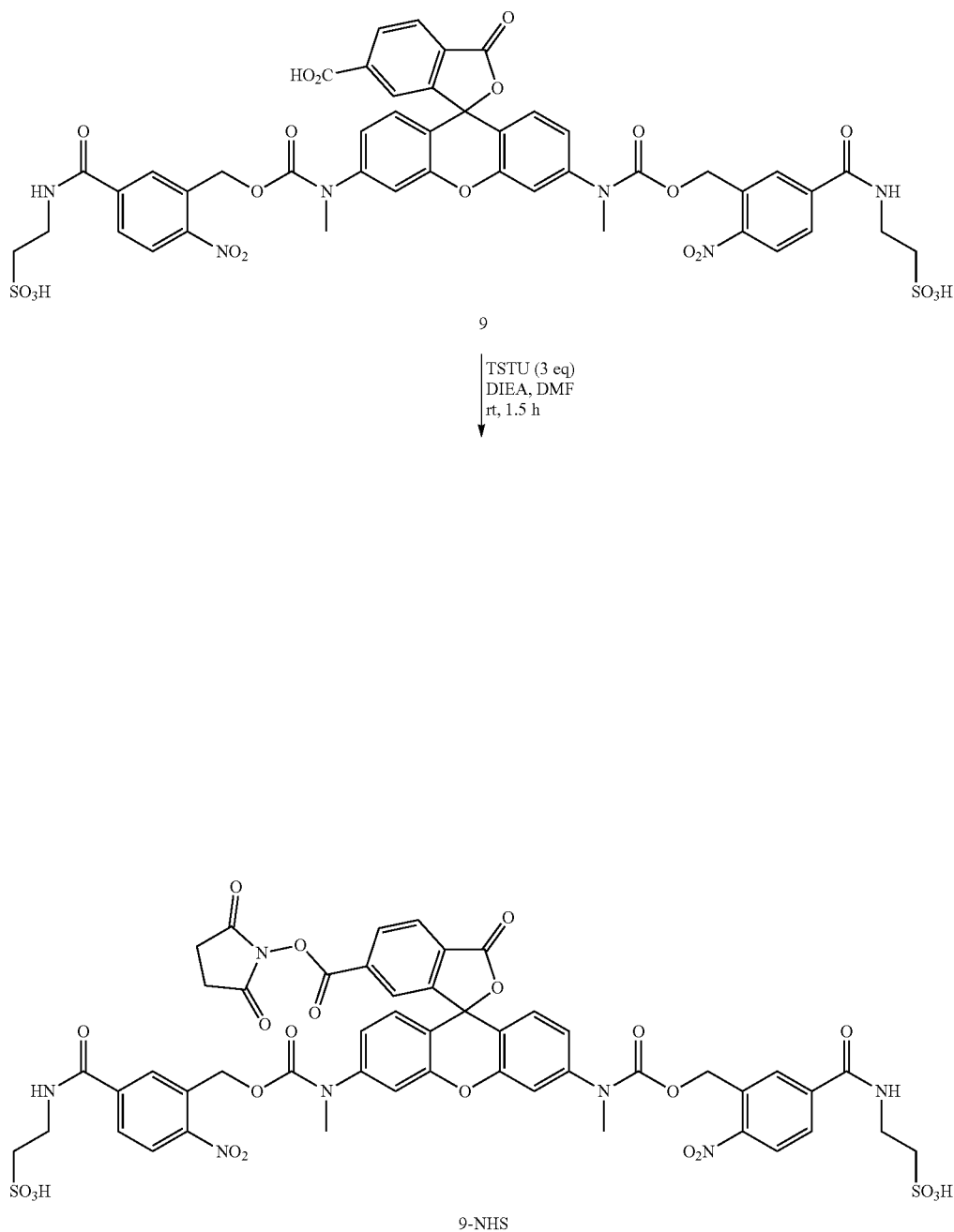

Compound 9-NHS. A solution of compound 9 (8 mg, 7.5 µmol) and N,N-ethyldiisopropylamine (DIEA; 60 µL) in DMF (150 µL) was treated with N,N,N',N'-tetramethyl-O—(N-succinimidyl)uronium tetrafluoroborate (TSTU; 6.8 mg, 22.6 µmol in 50 µL DMF). The reaction mixture was stirred at rt for 1.5 h, the solvents were evaporated to dryness and the residue was dried in vacuo. The product was isolated by preparative HPLC (column: Interchim 250×21.2 mm 5 µm Uptisphere Strategy PhC4; gradient 20/80→60/40 A:B, A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 9-NHS as light orange solid (7 mg, 81%).

HRMS (C$_{49}$H$_{41}$N$_7$O$_{23}$S$_2$): m/z (positive mode)= 1160.1767 (found [M+H]$^+$), 1160.1768 (calc.).

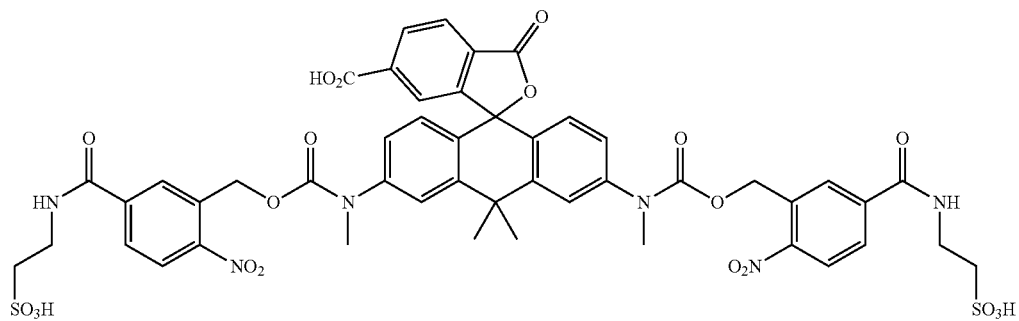

13

TSTU (3 eq)
DIEA, DMF
rt, 1 h

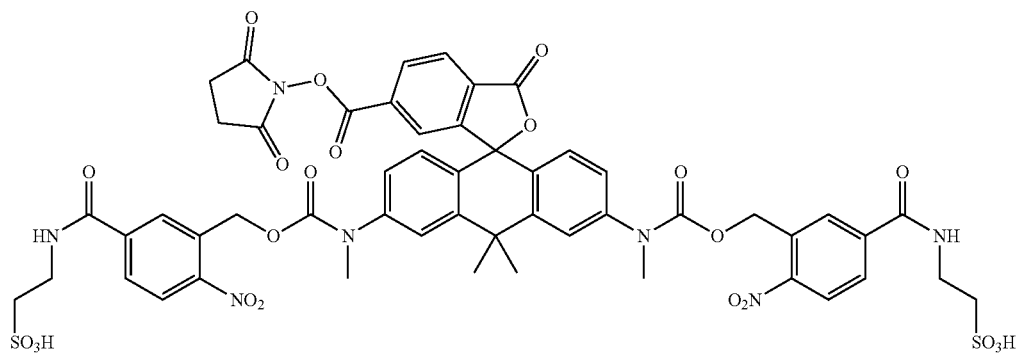

13-NHS

Compound 13-NHS. A solution of compound 13 (7 mg, 6.43 µmol) and N,N-ethyldiisopropylamine (DIEA; 50 µL) in DMF (150 µL) was treated with N,N,N',N'-tetramethyl-O—(N-succinimidyl)uronium tetrafluoroborate (TSTU; 5.8 mg, 19.4 µmol in 50 µL DMF). The reaction mixture was stirred at rt for 1 h, the solvents were evaporated to dryness and the residue was dried in vacuo. The product was isolated by preparative HPLC (column: Interchim 250×21.2 mm 5 µm Uptisphere Strategy PhC4; gradient 20/80→60/40 A:B, A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 13-NHS as light pink solid (9.3 mg, ~100%, bis-DIEA salt).

HRMS ($C_{52}H_{47}N_7O_{22}S_2$): m/z (positive mode)= 1186.2287 (found [M+H]$^+$), 1186.2288 (calc.).

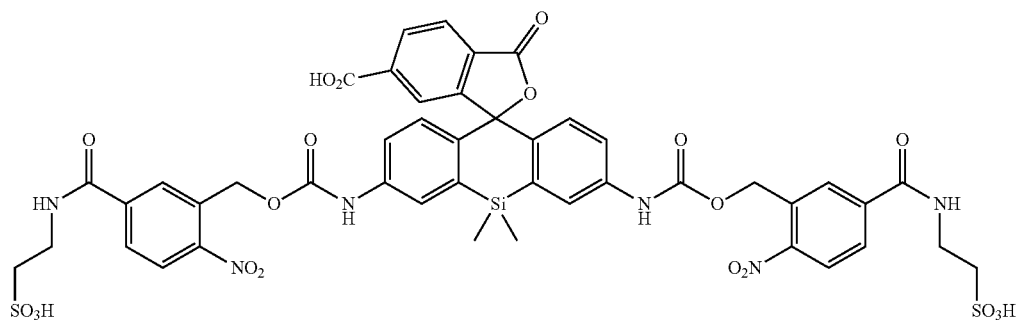

17

TSTU (6 eq)
DIEA, DMF
rt, 2 h

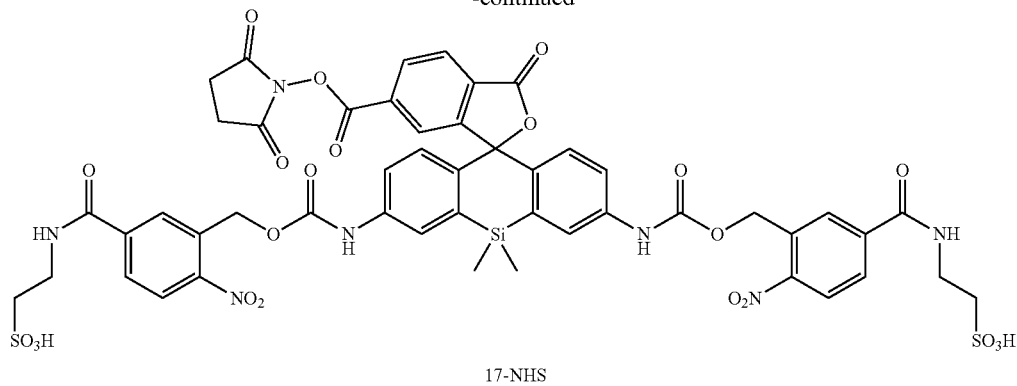

17-NHS

Compound 17-NHS. A solution of compound 17 (6.5 mg, 4.6 μmol) and N,N-ethyldiisopropylamine (DIEA; 50 μL) in DMF (150 μL) was treated with N,N,N',N'-tetramethyl-O—(N-succinimidyl)uronium tetrafluoroborate (TSTU; 4.2 mg, 14 μmol in 40 μL DMF). The reaction mixture was stirred at rt for 1 h, at which time the LC/MS analysis showed incomplete conversion, so another portion of TSTU (4.2 mg, 14 μmol in 40 μL DMF) was added and the mixture was stirred for another 1 h period. The solvents were evaporated to dryness and the residue was dried in vacuo. The product was isolated by preparative HPLC (column: Interchim 250× 21.2 mm 5 μm Uptisphere Strategy PhC4; gradient 20/80→60/40 A:B, A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 17-NHS as light violet solid (7.2 mg, ~100%, bis-DIEA salt).

HRMS (C$_{49}$H$_{43}$N$_7$O$_{22}$S$_2$Si): m/z (positive mode)= 1174.1745 (found [M+H]$^+$), 1174.1745

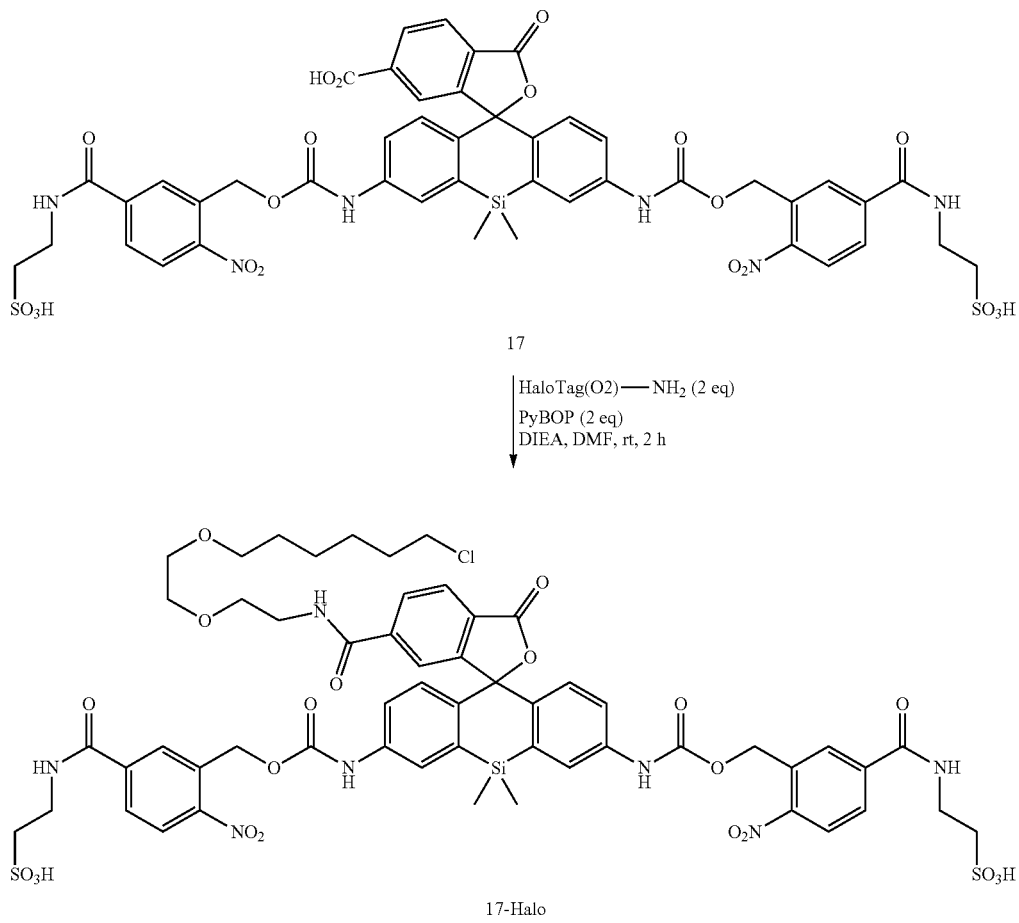

17

HaloTag(O2)—NH$_2$ (2 eq)
PyBOP (2 eq)
DIEA, DMF, rt, 2 h

17-Halo

Compound 17-Halo. A solution of compound 17 (4 mg, 3.71 µmol) and N,N-ethyldiisopropylamine (DIEA; 30 µL) in DMF (100 µL) was treated with HaloTag(O2)-NH$_2$ ligand (1.7 mg, 7.43 µmol in 25 µL DMF) and (benzotriazol-1-yloxy)tripyrrolidinophosphonium hexafluorophosphate (PyBOP; 3.9 mg, 7.43 µmol in 30 µL DMF). The resulting light yellow clear solution was stirred at rt for 2 h, the solvents were then evaporated to dryness and the residue was dried in vacuo. The product was isolated by preparative HPLC (column: Interchim 250×21.2 mm 5 µm Uptisphere Strategy PhC4; gradient 20/80→70/30 A:B, A=acetonitrile, B=50 mM ammonium formate in water, pH=3.5-4.0; detection at 220 nm), fractions containing the product were evaporated (bath temperature 30° C.), and the residue was freeze-dried from aq. dioxane to give 17-Halo as white solid (4 mg, 84%).

HRMS (C$_{55}$H$_{60}$ClN$_7$O$_{21}$S$_2$Si): m/z (positive mode) =1282.2810 (found [M+H]$^+$), 1282.2814

Compound 21-NHS. A solution of compound 21 (4.4 mg, 4 µmol) and N,N-ethyldiisopropylamine (DIEA; 40 µL) in DMF (150 µL) was treated with N,N,N',N'-tetramethyl-O—(N-succinimidyl)uronium tetrafluoroborate (TSTU; 3.7 mg, 12 µmol in 40 µL DMF). The reaction mixture was stirred at rt for 1 h, the solvents were evaporated to dryness and the residue was dried in vacuo. The product was isolated by preparative HPLC (column: Interchim 250×21.2 mm 5 µm Uptisphere Strategy PhC4; gradient 20/80→60/40 A:B, A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 21-NHS as white solid (3.5 mg, 73%).

HRMS (C$_{51}$H$_{45}$N$_7$O$_{22}$S$_2$Si): m/z (positive mode)= 1202.2062 (found [M+H]$^+$), 1202.2058

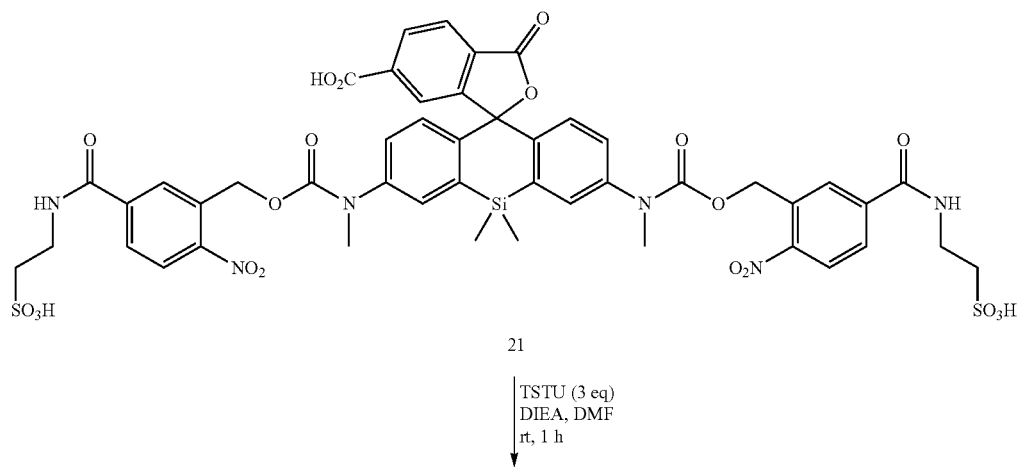

21

TSTU (3 eq)
DIEA, DMF
rt, 1 h

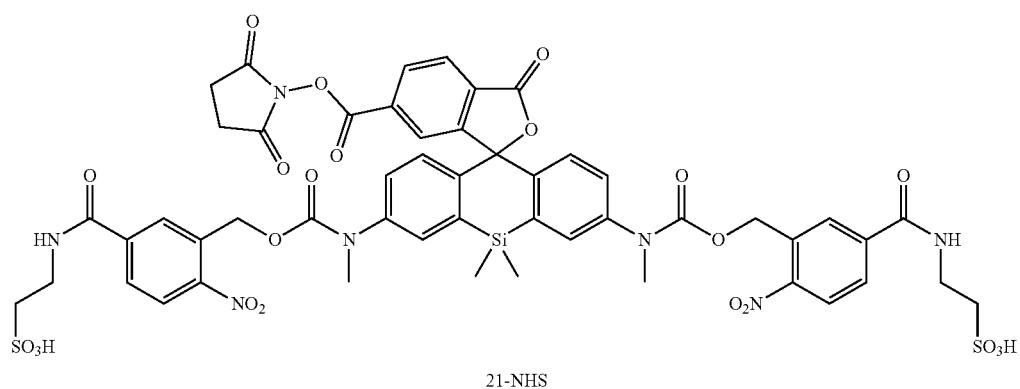

21-NHS

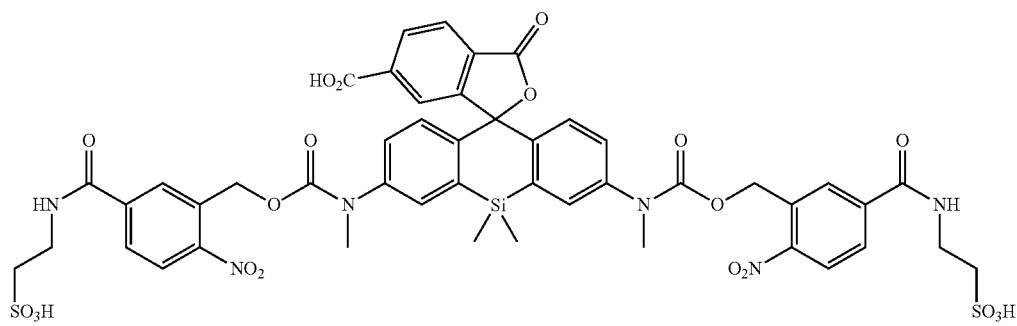

21

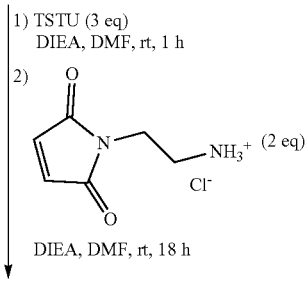

DIEA, DMF, rt, 18 h

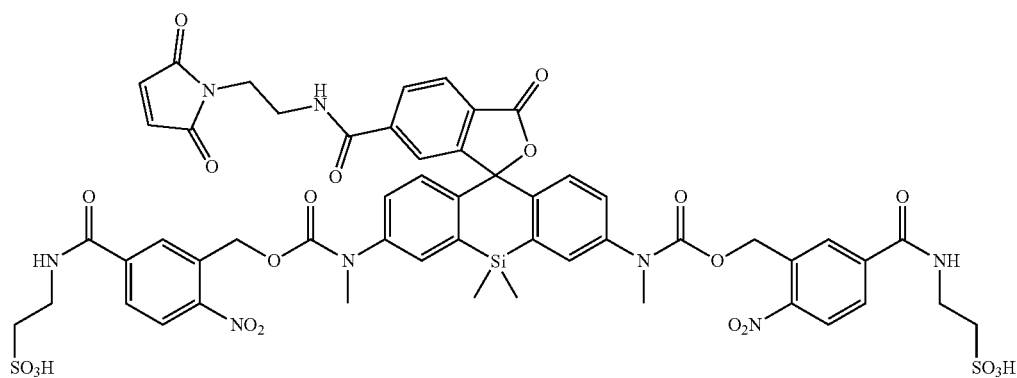

21-Maleimide

Compound 21-Maleimide. A solution of compound 21 (5 mg, 4.53 μmol) and N,N-ethyldiisopropylamine (DIEA; 45 μL) in DMF (100 μL) was treated with N,N,N',N'-tetramethyl-O—(N-succinimidyl)uronium tetrafluoroborate (TSTU; 4.1 mg, 13.6 μmol in 40 μL DMF). The reaction mixture was stirred at rt for 1 h, and DIEA (45 μL) was added followed by the solution of 1-(2-aminoethyl)maleimide hydrochloride (1.6 mg, 9.06 μmol in 30 μL DMF). The mixture was left stirring at rt overnight (18 h), the solvents were then evaporated to dryness and the residue was dried in vacuo. The product was isolated by preparative HPLC (column: Interchim 250×21.2 mm 5 μm Uptisphere Strategy PhC4; gradient 20/80→60/40 A:B, A=acetonitrile, B=50 mM triethylammonium bicarbonate in water, pH=7.0-7.5; detection at 220 nm), fractions containing the product were evaporated (bath temperature 30° C.), and the residue was freeze-dried from aq. dioxane to give 21-Maleimide as yellowish solid (3.8 mg, 68%).

HRMS ($C_{53}H_{50}N_8O_{21}S_2Si$): m/z (positive mode)= 1227.2375 (found [M+H]$^+$), 1227.2374

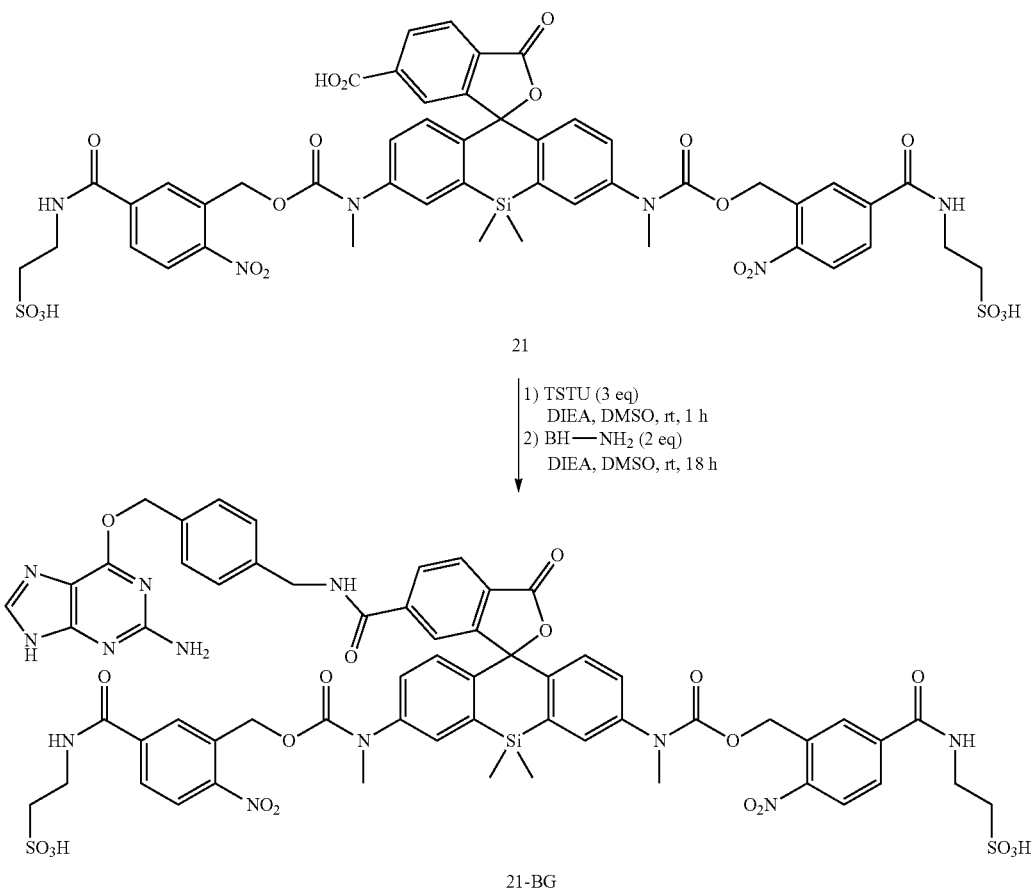

Compound 21-BG. A solution of compound 21 (5 mg, 4.53 μmol) and N,N-ethyldiisopropylamine (DIEA; 45 μL) in DMSO (100 μL) was treated with N,N,N',N'-tetramethyl-O—(N-succinimidyl)uronium tetrafluoroborate (TSTU; 4.1 mg, 13.6 μmol in 40 μL DMF). The reaction mixture was stirred at rt for 1 h, and DIEA (45 μL) was added followed by the solution of 6-((4-(aminomethyl)benzyloxy)-7H-purin-2-amine (BG-NH$_2$; 2.4 mg, 9.06 μmol in 70 μL DMSO). The mixture was left stirring at rt overnight (18 h), the solvents were then evaporated to dryness and the residue was dried in vacuo. The product was isolated by preparative HPLC (column: Interchim 250×21.2 mm 5 μm Uptisphere Strategy PhC4; gradient 20/80→60/40 A:B, A=acetonitrile, B=50 mM triethylammonium bicarbonate in water, pH=7.0-7.5; detection at 220 nm), fractions containing the product were evaporated (bath temperature 30° C.), and the residue was freeze-dried from aq. dioxane to give 21-BG as white solid (3.2 mg, 52%).

HRMS (C$_{60}$H$_{56}$N$_{12}$O$_{20}$S$_2$Si): m/z (positive mode)= 1357.3021 (found [M+H]$^+$), 1357.3017

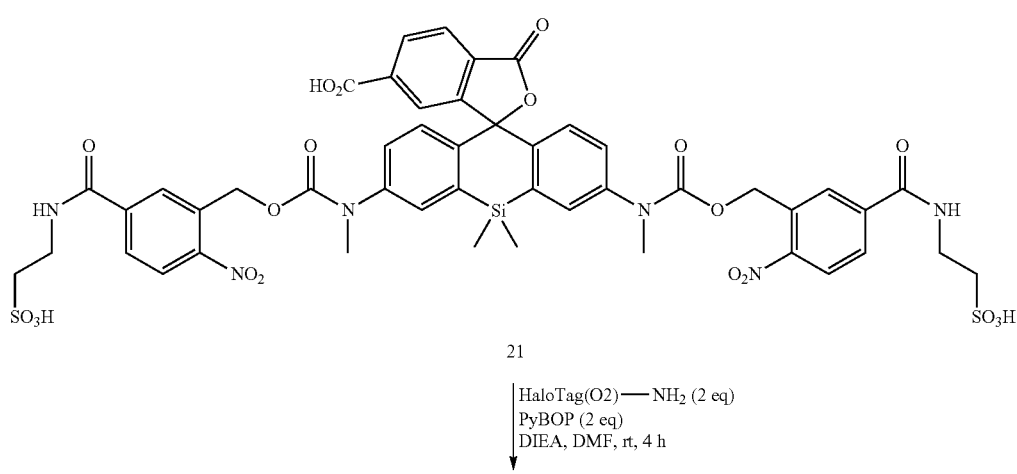

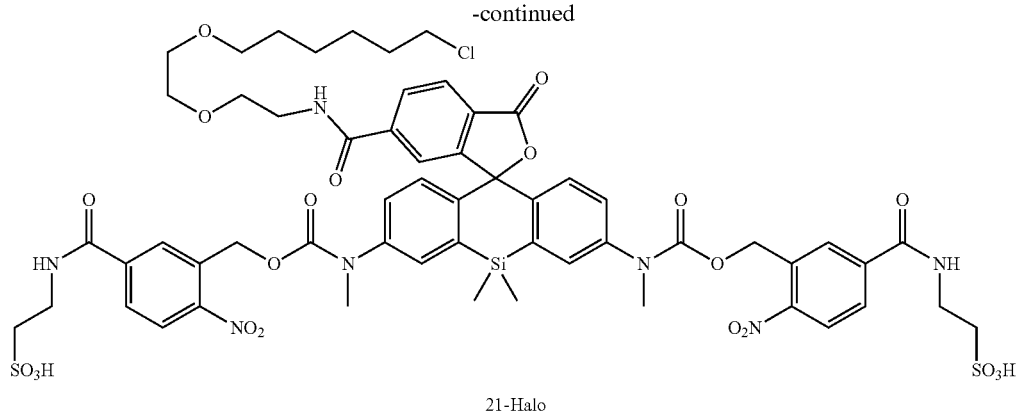

21-Halo

Compound 21-Halo. A solution of compound 21 (5 mg, 4.53 µmol) and N,N-ethyldiisopropylamine (DIEA; 30 µL) in DMF (100 µL) was treated with HaloTag(O2)-NH$_2$ ligand (2 mg, 9.1 µmol in 25 µL DMF) and (benzotriazol-1-yloxy)tripyrrolidinophosphonium hexafluorophosphate (PyBOP; 4.7 mg, 9.1 µmol in 30 µL DMF). The resulting light yellow clear solution was stirred at rt for 4 h, the solvents were then evaporated to dryness and the residue was dried in vacuo. The product was isolated by preparative HPLC (column: Interchim 250×21.2 mm 5 µm Uptisphere Strategy PhC4; gradient 20/80→70/30 A:B, A=acetonitrile, B=50 mM ammonium formate in water, pH=3.5-4.0; detection at 220 nm), fractions containing the product were evaporated (bath temperature 30° C.), and the residue was freeze-dried from aq. dioxane to give 21-Halo as white solid (4.9 mg, 83%).

HRMS (C$_{57}$H$_{64}$ClN$_7$O$_{21}$S$_2$Si): m/z (positive mode)= 1310.3126 (found [M+H]$^+$), 1310.3127

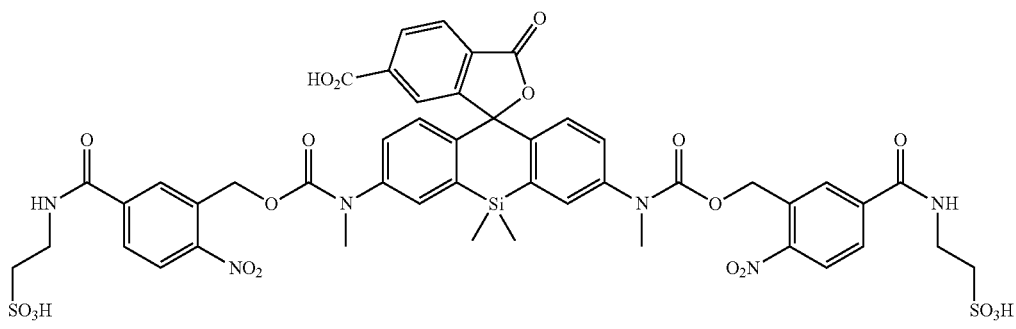

21

1) TSTU (3 eq)
   DIEA, DMF, rt, 1 h
2) 5 (2.5 eq)
   DIEA, DMF, rt, 18 h

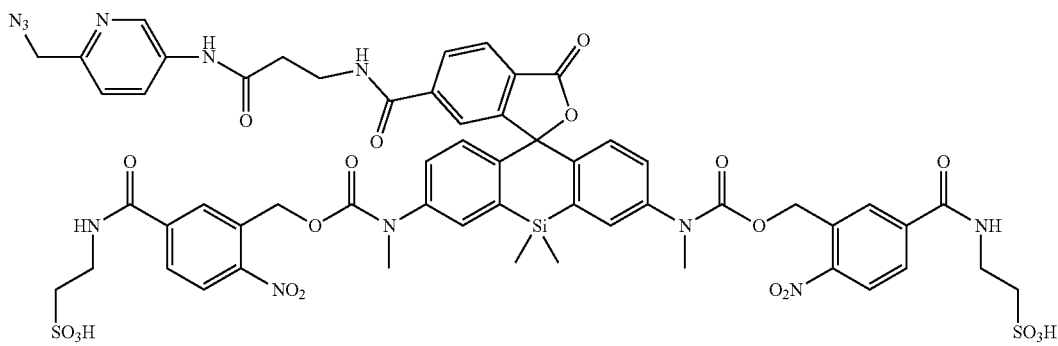

21-Picolyl azide

Compound 21-Picolyl azide. A solution of compound 21 (5 mg, 4.53 μmol) and N,N-ethyldiisopropylamine (DIEA; 45 μL) in DMF (100 μL) was treated with N,N,N',N'-tetramethyl-O—(N-succinimidyl)uronium tetrafluoroborate (TSTU; 4.1 mg, 13.6 μmol in 40 μL DMF). The reaction mixture was stirred at rt for 1 h, and DIEA (45 μL) was added followed by the solution of 5 (5 mg, 11.2 μmol in 30 μL DMF). The mixture was left stirring at rt overnight (18 h), the solvents were then evaporated to dryness and the residue was dried in vacuo. The product was isolated by preparative HPLC (column: Interchim 250×21.2 mm 5 μm Uptisphere Strategy PhC4; gradient 10/90→60/40 A:B A=0.1% v/v HCO$_2$H in acetonitrile, B=0.1% v/v HCO$_2$H in water; detection at 220 nm), fractions containing the product were evaporated (bath temperature 30° C.), and the residue was freeze-dried from aq. dioxane to give 21-Picolyl azide as off-white solid (4.9 mg, 83%).

HRMS (C$_{56}$H$_{54}$N$_{12}$O$_{20}$S$_2$Si): m/z (positive mode)= 1307.2860 (found [M+H]$^+$), 1307.2861 (calc.).

EXAMPLE 3

Characterization of Exemplary Compounds of the Present Invention

General Materials and Methods

All chemical reagents (TCI, Sigma-Aldrich, Alfa Aesar) and dry solvents for synthesis (over molecular sieves, AcroSeal package, Acros Organics) were purchased from reputable suppliers and were used as received without further purification. The products were lyophilized from a suitable solvent system using Alpha 2-4 LDplus freeze-dryer (Martin Christ Gefriertrocknungsanlagen GmbH).

Thin Layer Chromatography

Normal phase TLC was performed on silica gel 60 F$_{254}$ (Merck Millipore, Germany). For TLC on reversed phase silica gel 60 RP-18 F$_{254}$s (Merck Millipore) was used. Compounds were detected by exposing TLC plates to UV-light (254 or 366 nm) or heating with vanillin stain (6 g vanillin and 1.5 mL conc. H$_2$SO$_4$ in 100 mL ethanol), unless indicated otherwise.

Flash Chromatography

Preparative flash chromatography was performed with an automated Isolera One system with Spektra package (Biotage AG) using commercially available cartridges of suitable size as indicated (RediSep Rf series from Teledyne ISCO, Puriflash Silica HP 30 μm series from Interchim).

Nuclear Magnetic Resonance (NMR)

NMR spectra were recorded on a Bruker DPX 400 spectrometer. All spectra are referenced to tetramethylsilane as an internal standard (δ=0.00 ppm). Multiplicities of the signals are described as follows: s=singlet, d=doublet, t=triplet, q=quartet, m=multiplet or overlap of non-equivalent resonances; br=broad signal. Coupling constants $^nJ_{X-Y}$ are given in Hz, where n is the number of bonds between the coupled nuclei X and Y ($J_{H-H}$ are always listed as/without indices).

Mass-Spectrometry (MS)

Low resolution mass spectra (100-1500 m/z) with electrospray ionization (ESI) were obtained on a Shimadzu LC-MS system described below. High resolution mass spectra (HRMS) were obtained on a maXis II ETD (Bruker) with electrospray ionization (ESI) at the Mass Spectrometry Core facility of the Max-Planck Institute for Medical Research (Heidelberg, Germany).

High-Performance Liquid Chromatography (HPLC)

Analytical liquid chromatography-mass spectrometry was performed on an LC-MS system (Shimadzu): 2× LC-20AD HPLC pumps with DGU-20A3R solvent degassing unit, SIL-20ACHT autosampler, CTO-20AC column oven, SPD-M30A diode array detector and CBM-20A communication bus module, integrated with CAMAG TLC-MS interface 2 and LCMS-2020 spectrometer with electrospray ionization (ESI, 100-1500 m/z). Analytical column: Hypersil GOLD 50×2.1 mm 1.9 μm, standard conditions: sample volume 1-2 μL, solvent flow rate 0.5 mL/min, column temperature 30° C. General method: isocratic 95:5 A:B over 2 min, then gradient 95:5-0:100 A:B over 5 min, then isocratic 0:100 A:B over 2 min; solvent A=water+0.1% v/v HCO$_2$H, solvent B=acetonitrile+0.1% v/v HCO$_2$H.

Preparative high-performance liquid chromatography was performed on a Büchi Reveleris Prep system using the suitable preparative columns and conditions as indicated for individual preparations. Method scouting was performed on a HPLC system (Shimadzu): 2× LC-20AD HPLC pumps with DGU-20A3R solvent degassing unit, CTO-20AC column oven equipped with a manual injector with a 20 μL sample loop, SPD-M20A diode array detector, RF-20A fluorescence detector and CBM-20A communication bus module; or on a Dionex Ultimate 3000 UPLC system: LPG-3400SD pump, WPS-3000SL autosampler, TCC-3000SD column compartment with 2×7-port 6-position valves and DAD-3000RS diode array detector. The test runs were performed on analytical columns with matching phases (HPLC: Interchim 250×4.6 mm 10 μm C18HQ, Interchim 250×4.6 mm 5 μm PhC4, solvent flow rate 1.2 mL/min; UPLC: Interchim C18HQ or PhC4 75×2.1 mm 2.2 μm, ThermoFisher Hypersil GOLD 100×2.1 mm 1.9 μm, solvent flow rate 0.5 mL/min).

STED (Stimulated Emission Depletion) Microscopy

STED and confocal counterpart images were acquired using the commercially available STED 595/775 quad scanning microscope (Abberior Instruments, Göttingen, Germany) equipped with an Olympus IX83 microscope stand and an Olympus UplanSApo 100×/1.4 OIL objective. Dyes were excited respective their excitation (with 485 nm, 561 nm or 640 nm laser); the 595 nm and 775 nm STED lasers were pulsed at 40 MHz with a pulse length of ~1 ns. Imaging and image processing was done with ImSpector software, and the images are displayed as raw data.

EXAMPLE 4

STED Optical Microscopy of Cells Using Exemplary Novel Dyes of the Invention Coupled to Antibody Amino-reactive NHS-esters of the present dyes were coupled to secondary antibody using a standard coupling protocol. In brief, the reactive dye (9-NHS, 13-NHS, 17-NHS or 21-NHS; 100 μg) was dissolved in anhydrous DMSO (10 μL), mixed with 1 mg antibody in PBS+0.1 M NaHCO$_3$, stirred for 1 h and purified using a size exclusion column (PD 10, GE Healthcare). U2OS cells, grown on coverslips, were fixed using ice-cold methanol, permeabilzied with Triton X-100, blocked with 2% (w/v) BSA in PBS and treated with primary and secondary antibody in the same buffer with PBS washes in between. The samples were mounted on microscope slides with PBS and sealed with nail polish. In order to activate the dyes, the sample was illuminated with a 405 nm broadband LED for the duration of several seconds.

EXAMPLE 5

STED Optical Microscopy of Cells Using Exemplary Novel Dyes of the Invention with Self-Labelling Enzymes BG- or Halo-derivatives of the dyes of the present invention were dissolved in DMSO. Cells with stable expression of protein fusions with SNAP- or Halo-Tag [Ratz et al. Sci. Rep. 2015, 5, 9592; Butkevich et al. ACS Chem. Biol. 2018, 13(2), 475-480] or transfected cells were grown on coverslips and fixed with 2.4% (w/v) paraformaldehyde in PBS, permeabilized with Triton X-100, and treated with 21-BG or 21-Halo (200 nM in PBS) for one hour. After washing with PBS, the samples were mounted on microscope slides with PBS and sealed with nail polish. The caged dyes were activated by illumination with a 405 nm broadband LED for several seconds.

EXAMPLE 6

STED Optical Microscopy of M13 Bacteriophages Labelled Using Click Chemistry

Figure 4:
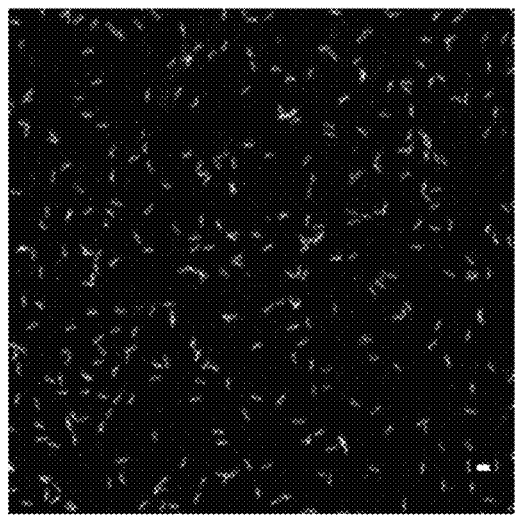
FIG. 4 shows confocal images of M13 bacteriophages: A—obtained by immunostaining with primary antibody (Abcam: ab9225) against g8p (a major coat protein of the phage) and a secondary antibody (Dianova: 515-005-003) labeled with Abberior STAR 488 dye; B,C—obtained by modification of coat proteins with 3-(2-propyn-1-yloxy)propanoic acid N-hydroxysuccinimidyl ester ("Propargyl-N-hydroxysuccinimidyl ester", CAS #1174157-65-3) followed by treatment with 21-Picolyl azide. The images were recorded before irradiation of the sample with a broadband 405 nm LED (B, background before dye uncaging) and after irradiation (C, after uncaging). Scale bar 1 μm.
Figure 4:
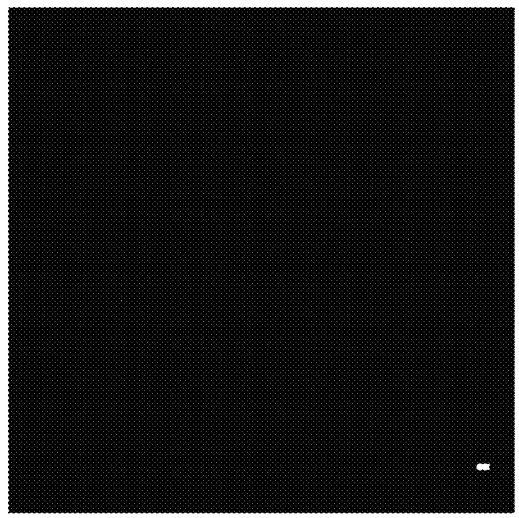
Figure 4:
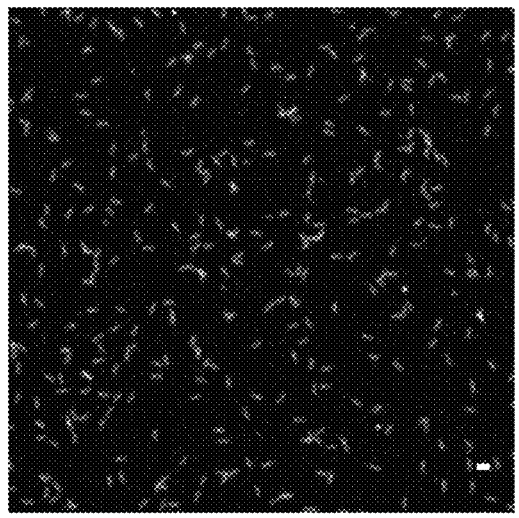
Figure 5:
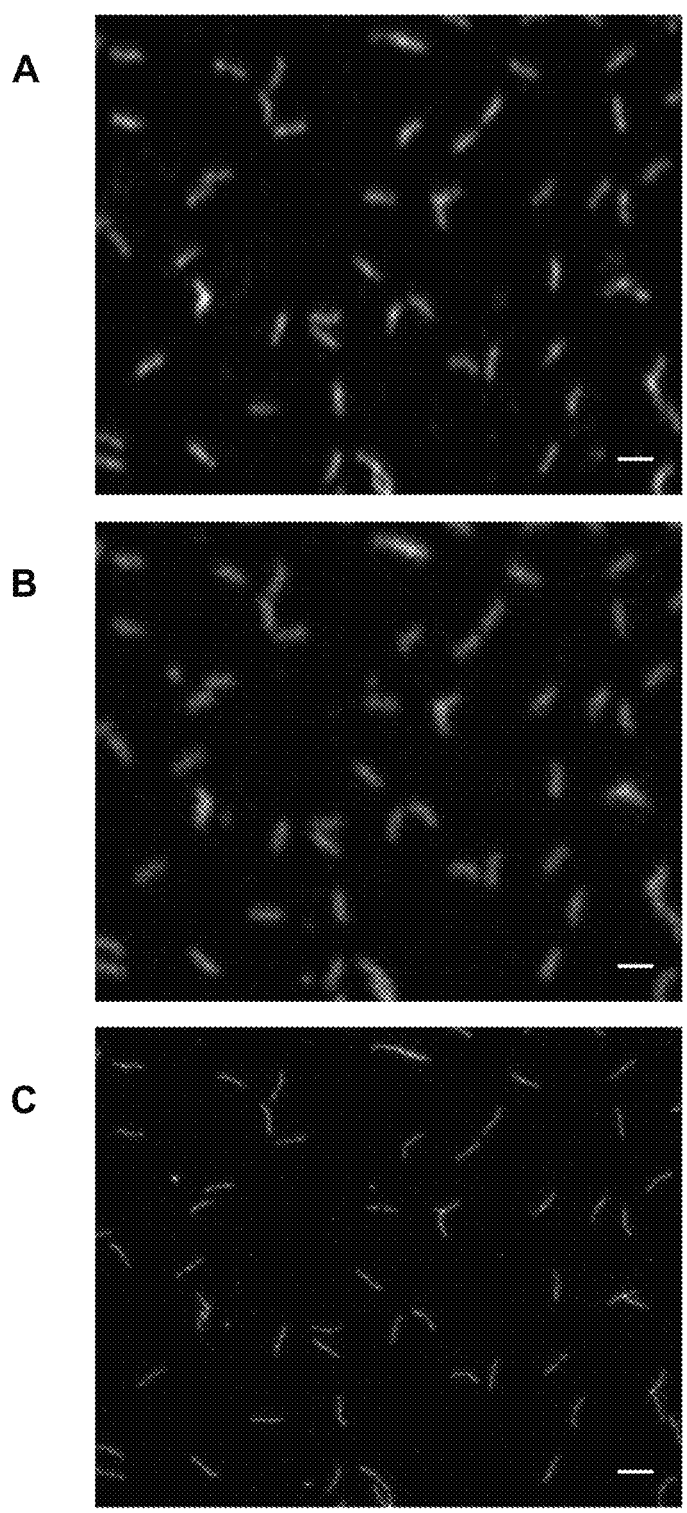
FIG. 5 shows images of M13 bacteriophages: A—confocal, obtained by immunostaining with a primary antibody (Abcam: ab9225) against g8p (a major coat protein of the phage) and a secondary antibody (Dianova: 515-005-003) labeled with Abberior STAR 488 dye; B,C—confocal (B) and STED (775 nm, c) images obtained by modification of coat proteins with 3-(2-propyn-1-yloxy)propanoic acid N-hydroxysuccinimidyl ester ("Propargyl-N-hydroxysuccinimidyl ester", CAS #1174157-65-3) followed by treatment with 21-Picolyl azide and uncaging the label by irradiating the sample with a broadband 405 nm LED. Scale bar 1 μm.

Purified M13 bacteriophages were modified with terminal alkyne groups using 3-(2-propyn-1-yloxy)propanoic acid N-hydroxysuccinimidyl ester ("Propargyl-N-hydroxysuccinimidyl ester", CAS #1174157-65-3) using the same protocol as for the labelling of antibodies. The alkyne modified phages were deposited on poly-L-lysine coated coverslips and treated with the picolyl-azide conjugate of one of the dyes of the present invention (21-Picolyl azide) under standard copper-catalyzed click chemistry conditions [Jiang et al. Bioconjugate Chem. 2014, 25(4), 698-706]. The labelled samples were treated with primary and secondary antibodies before mounting (see FIGS. 4,5). The caged dyes were activated by illumination with a 405 nm broadband LED for several seconds.

What is claimed is:

1. A compound which is a photoactivable fluorescent dye having the structural formula I:

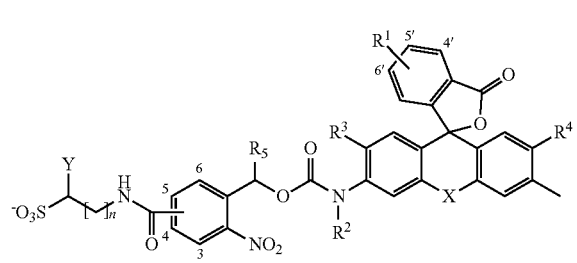

I

-continued

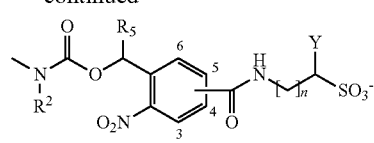

wherein:

n=0, 1, 2, 3;

X is selected from O, CRR', SiRR' and GeRR', where R and R' represent independently alkyl, cycloalkyl, alkenyl, alkynyl or aryl;

Y is H, $SO_3H$ or $SO_3M$, with M being a positively charged counterion;

$R^1$ is H, $CO_2H$, C(O)NH-linker-$CO_2H$, C(O)O-ligand, C(O)NH-ligand or C(O)NH-linker-ligand;

$R^2$ is H, unsubstituted alkyl, substituted alkyl, unsubstituted cycloalkyl or substituted cycloalkyl;

$R^3$ and $R^4$ are independently H or F;

$R^5$ is H, Me, $CO_2H$, C(O)NH-linker-$CO_2H$, C(O)O-ligand, C(O)NH-ligand or C(O)NH-linker-ligand;

wherein the ligand at each occurrence represents a reactive group or tag, capable to form a covalent or non-covalent bond or molecular complex with a target chemical entity or substance;

and wherein

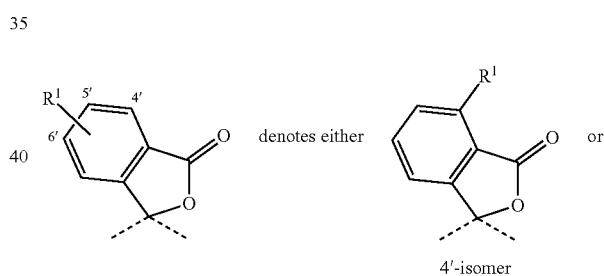

denotes either

4'-isomer or

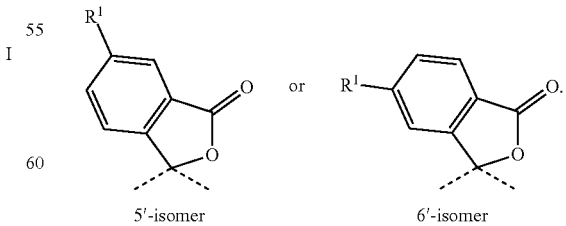

5'-isomer

6'-isomer

2. The compound according to claim 1, which is a 3,3-isomer, a 4,4-isomer or a 5,5-isomer of a compound of type I, as shown in the following structural formulae:

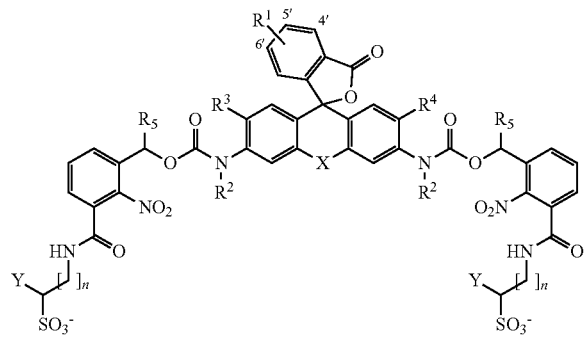

(3,3-isomer)

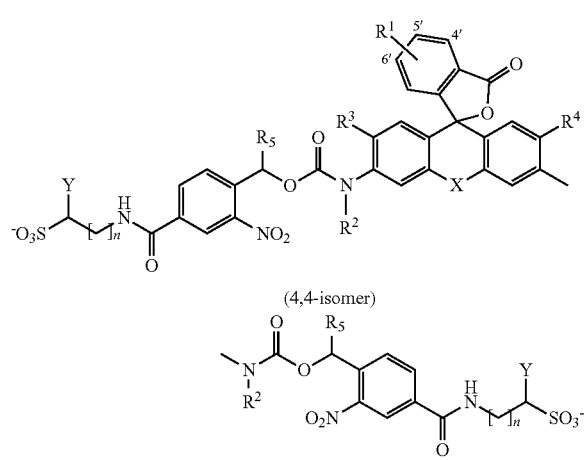

(4,4-isomer)

(5-5-isomer)

wherein n, X, Y, $R^1$, $R^2$, $R^3$, $R^4$ and $R^5$ are defined as in claim 1 above.

3. The compound according to claim 1, wherein the ligand:
   (a) comprises or represents a reactive group which is selected from an activated ester, an activated carbonate, an amine, a thiol, an azide, an alkene or alkyne, including a bicyclic and/or strained alkene or alkyne, a maleimide, and a tetrazine group;
   (b) is selected from the group consisting of a HaloTag ligand, a SNAP-Tag ligand, a CLIP-Tag ligand, a TMPTag ligand and functional analogs thereof; or
   (c) is selected from the group consisting of biotin, a taxoid moiety, phalloidin, and jasplakinolide.

4. The compound according to claim 1, having one of the following formulae IIa-IIj:

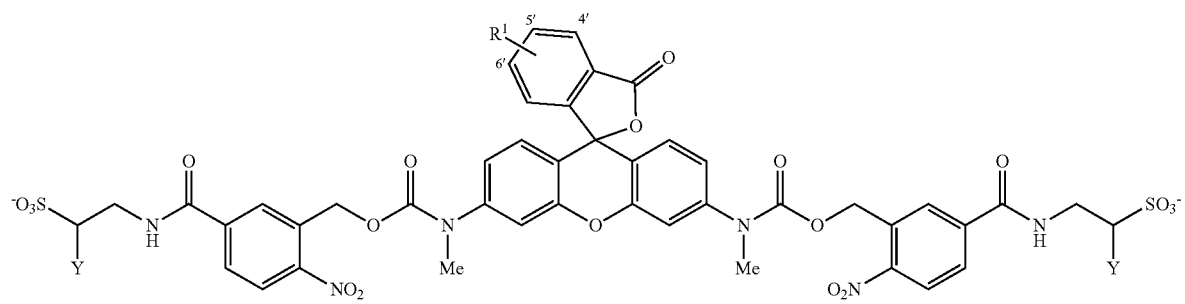

IIa

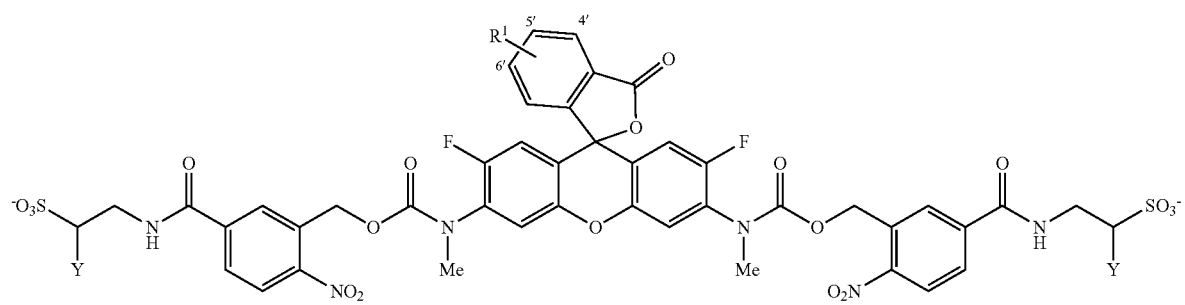

IIb

IIc
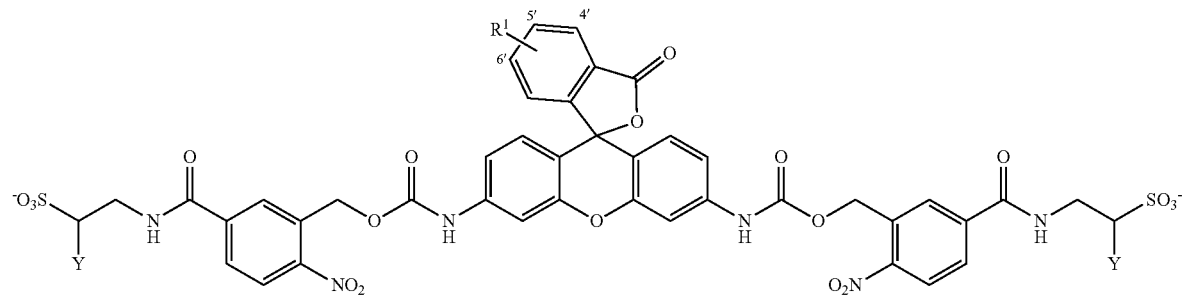
IId
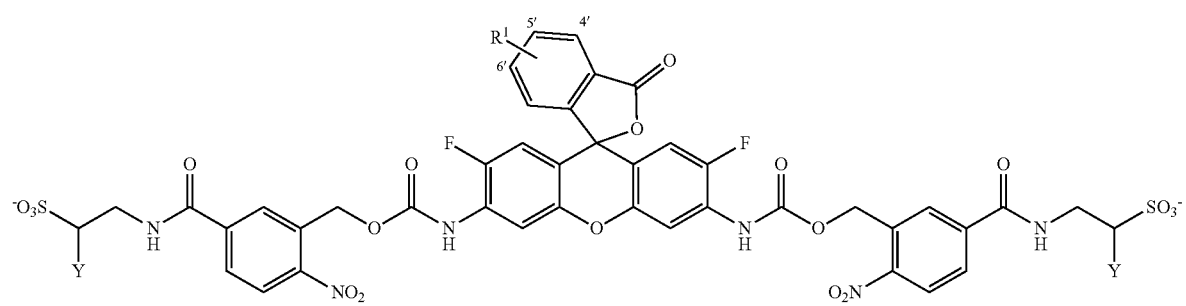
IIe
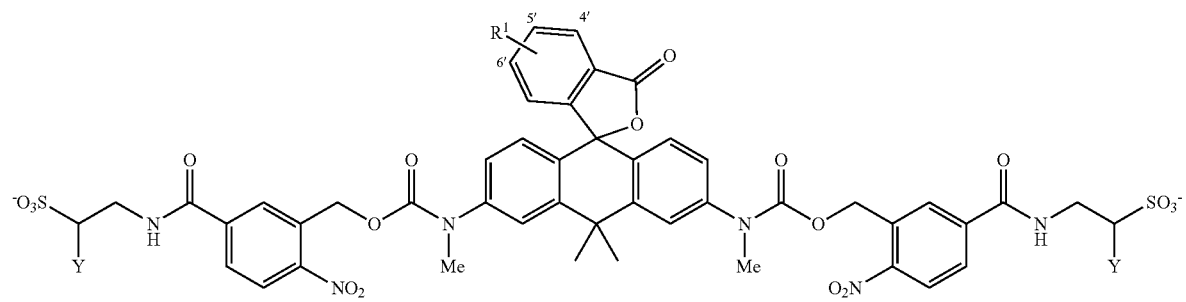
IIf
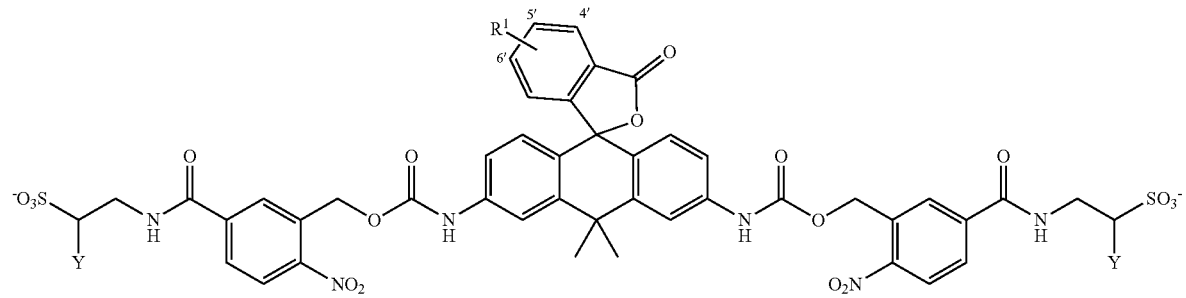

IIg
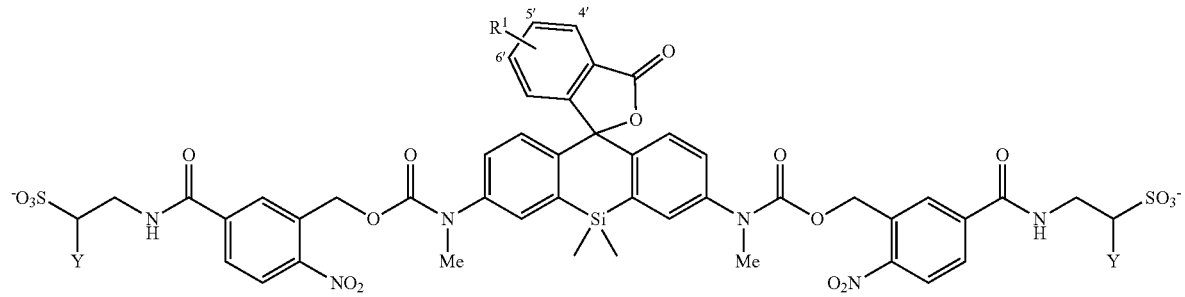
IIh
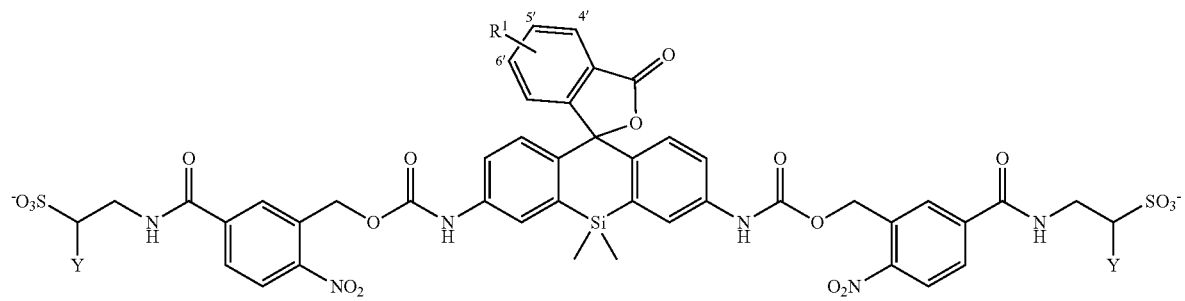
IIi
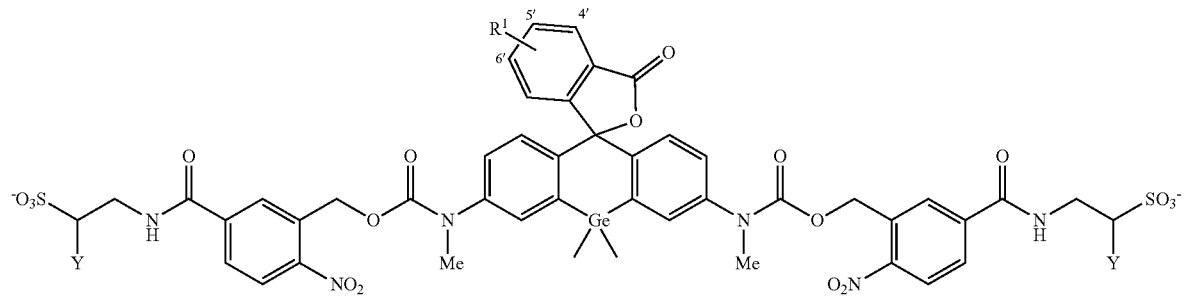
IIj
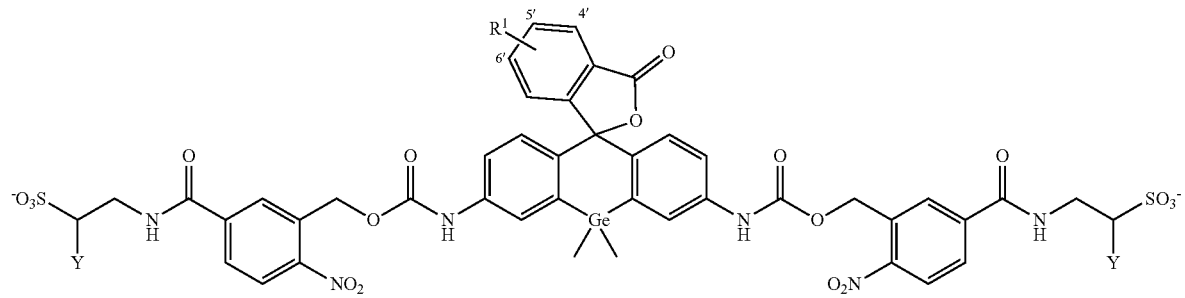
wherein Y and $R^1$ are defined as in claim 1 above.

5. The compound according to claim 3, which is a 4'-isomer, a 5'-isomer or a 6'-isomer of a compound of formulae IIa-IIj wherein $R^1$ represents a substituent group C(O)—Z and Z may represent OH, NH-linker-CO$_2$H, O-ligand, NH-ligand or NH-linker-ligand, and which has one of the following formulae 4'-IIIa-IIIj, 5'-IIIa-IIIj or 6'-IIIa-IIIj:
4'-IIIa
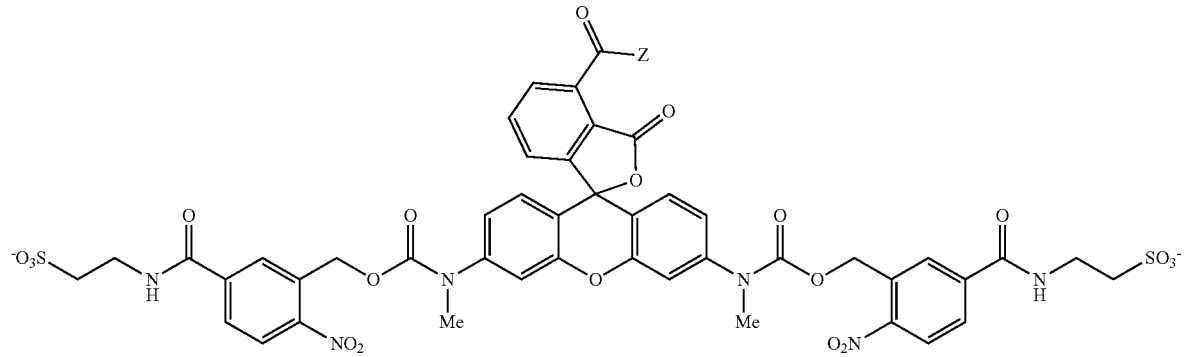
5'-IIIa
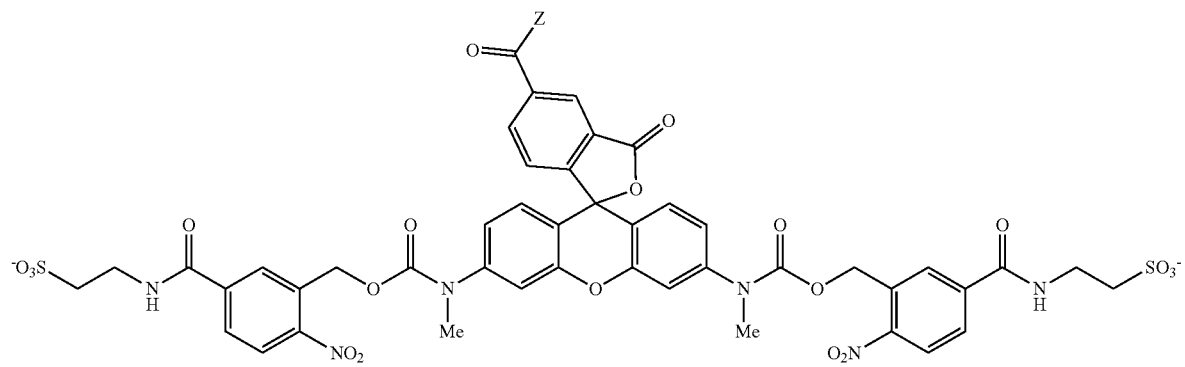
6'-IIIa
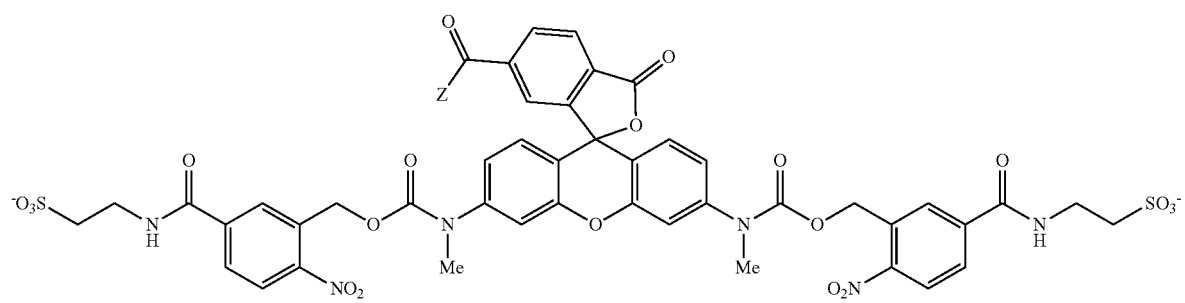
4'-IIIb
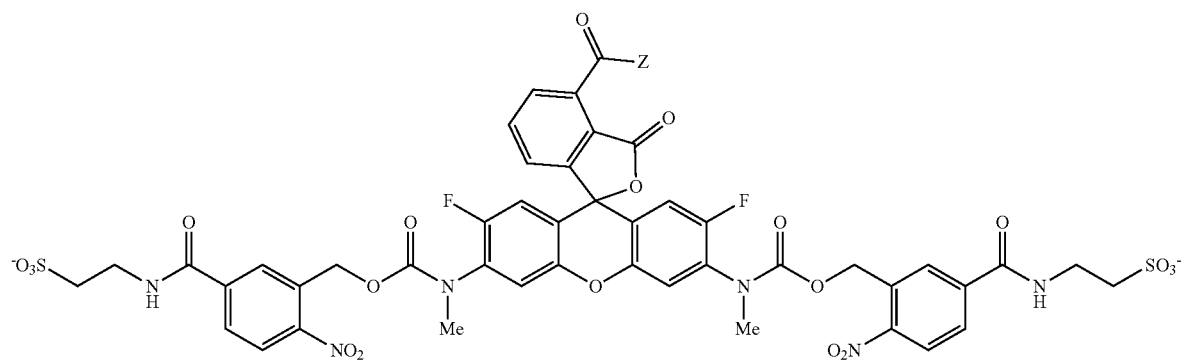

-continued
5'-IIIb
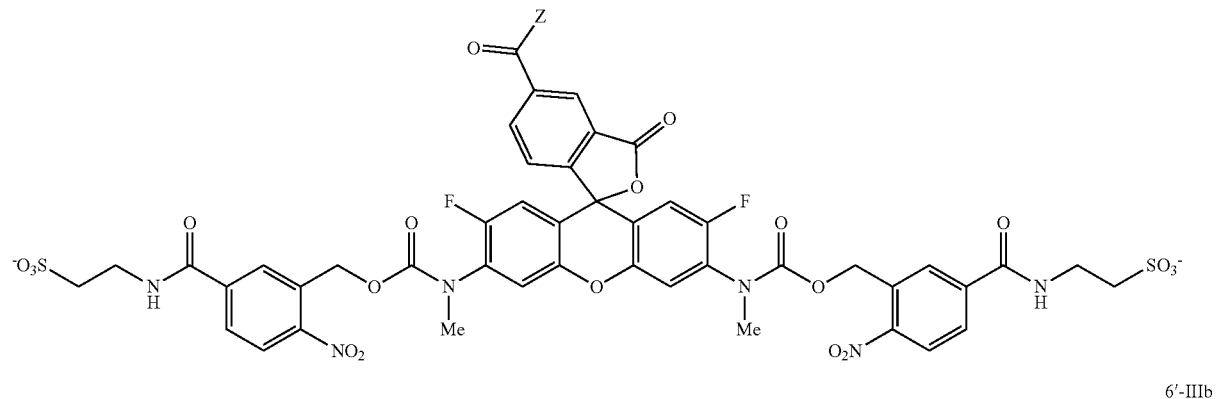
6'-IIIb
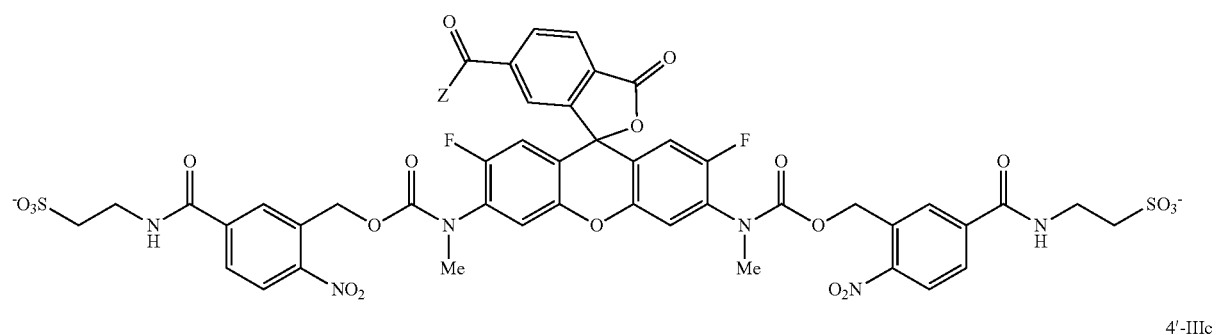
4'-IIIc
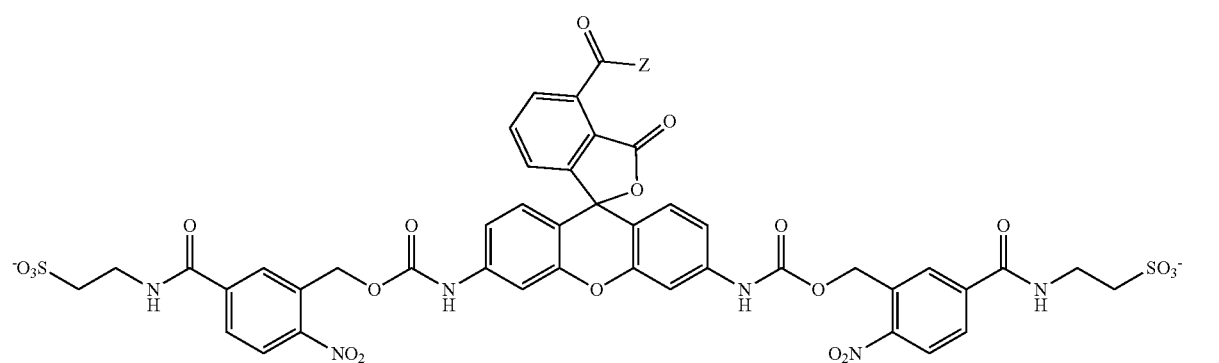
5'-IIIc
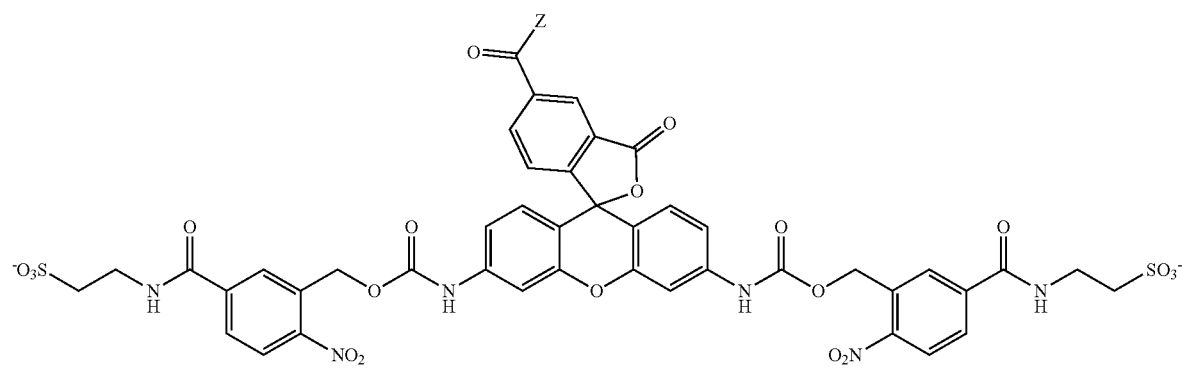

6'-IIIc
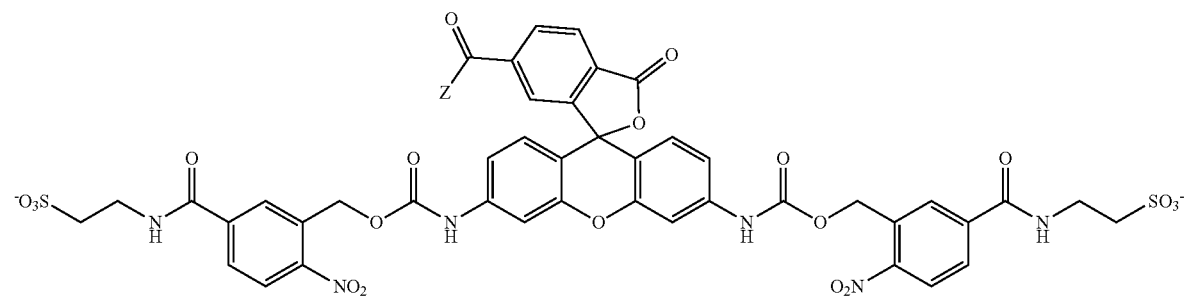
4'-IIId
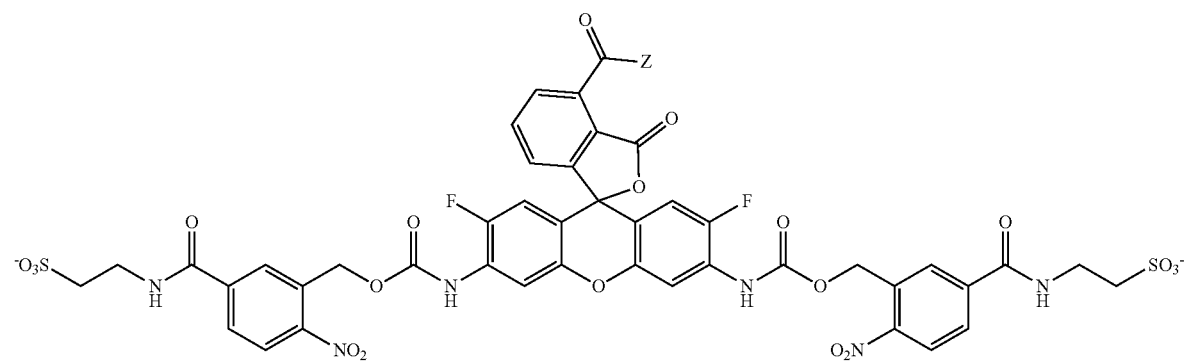
5'-IIId
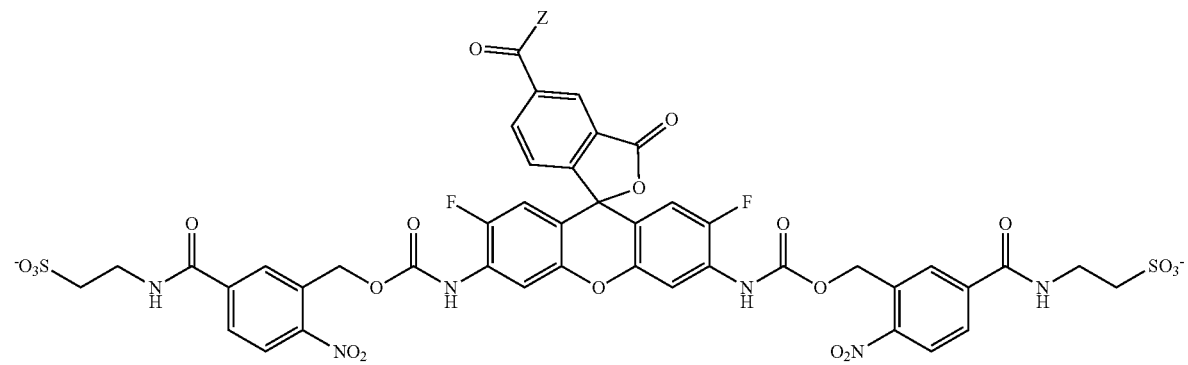
6'-IIId
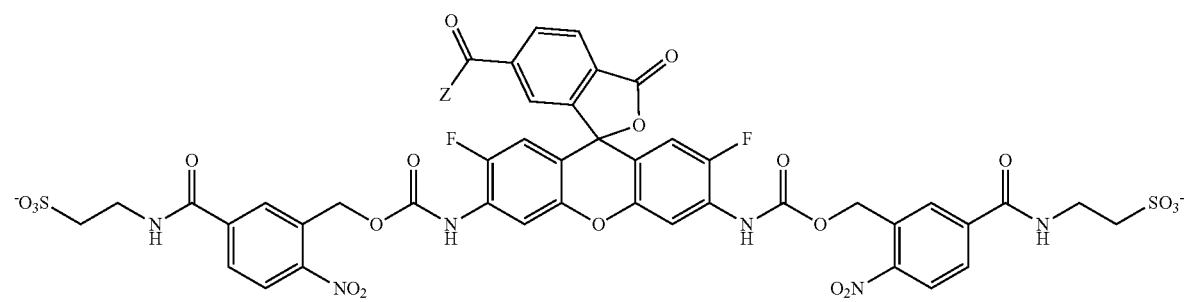

4'-IIIe
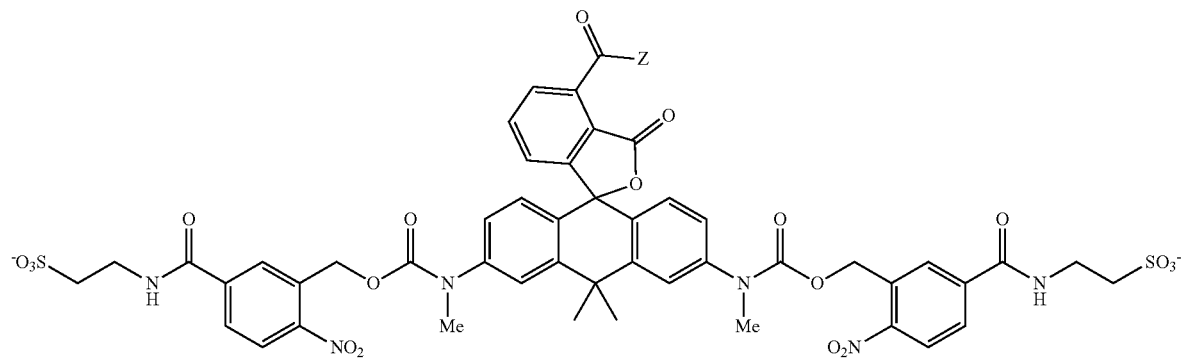
5'-IIIe
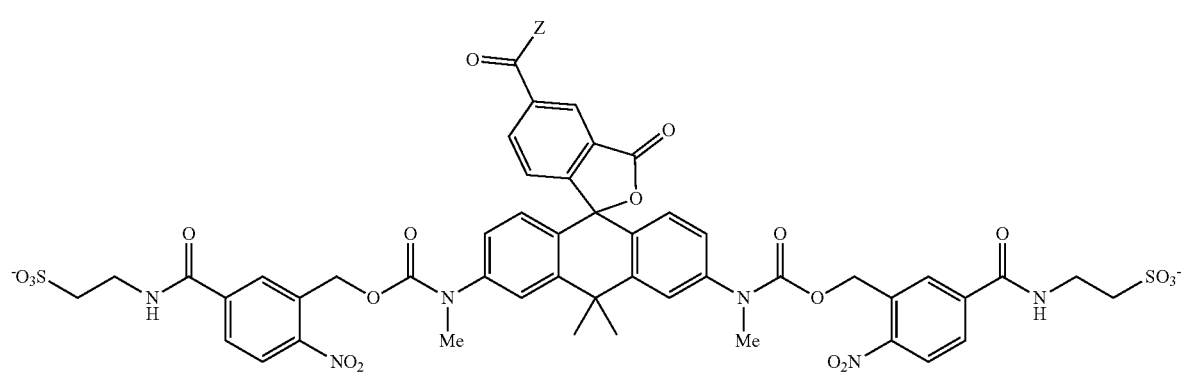
6'-IIIe
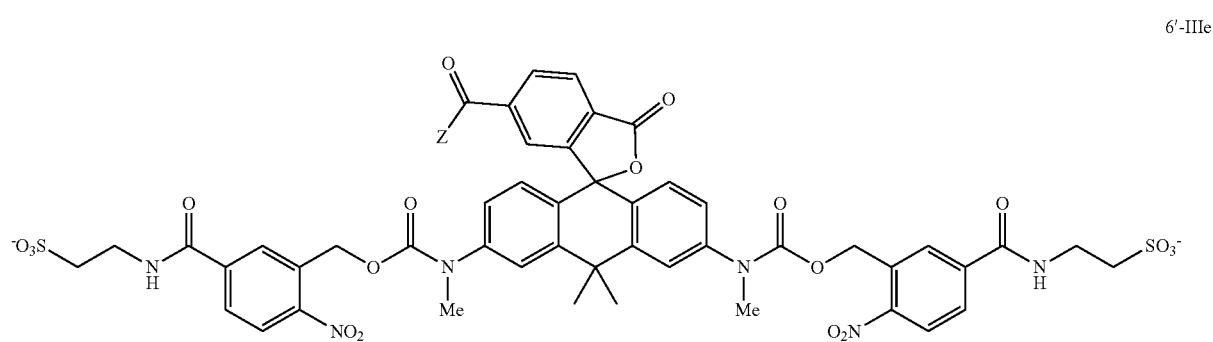
4'-IIIf
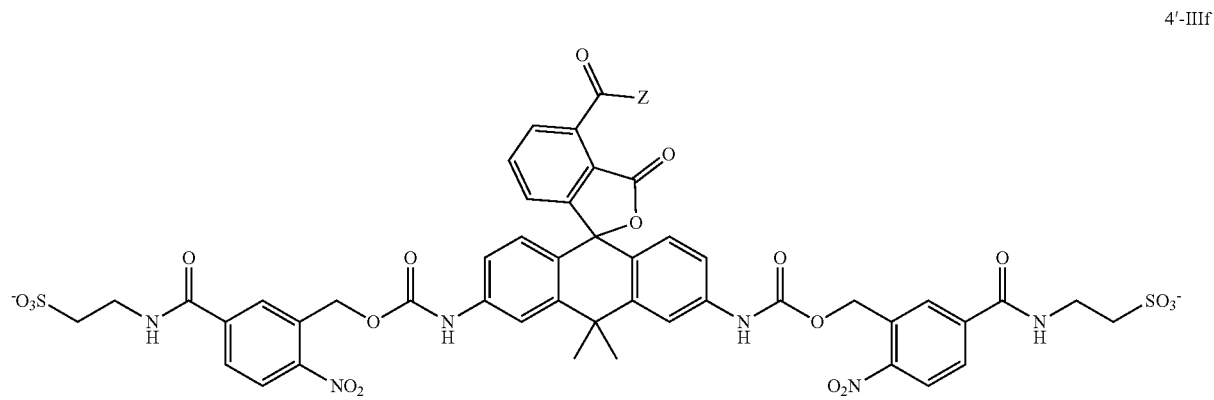

5'-IIIf
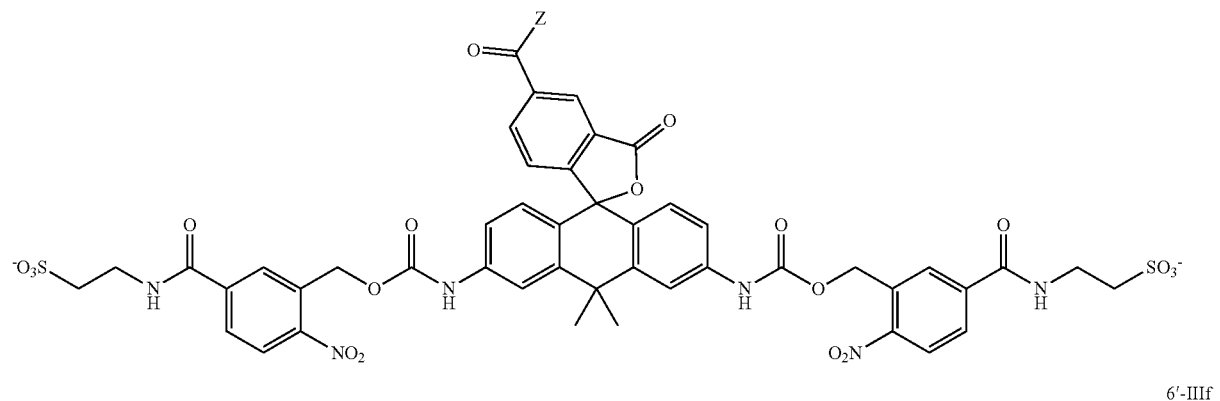
6'-IIIf
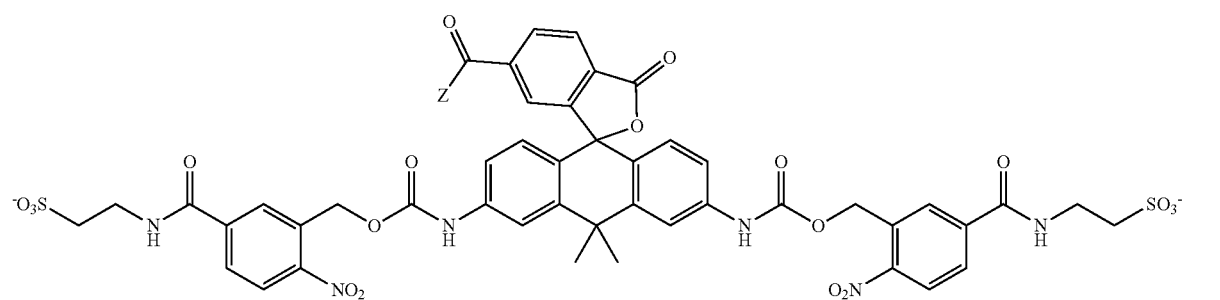
4'-IIIg
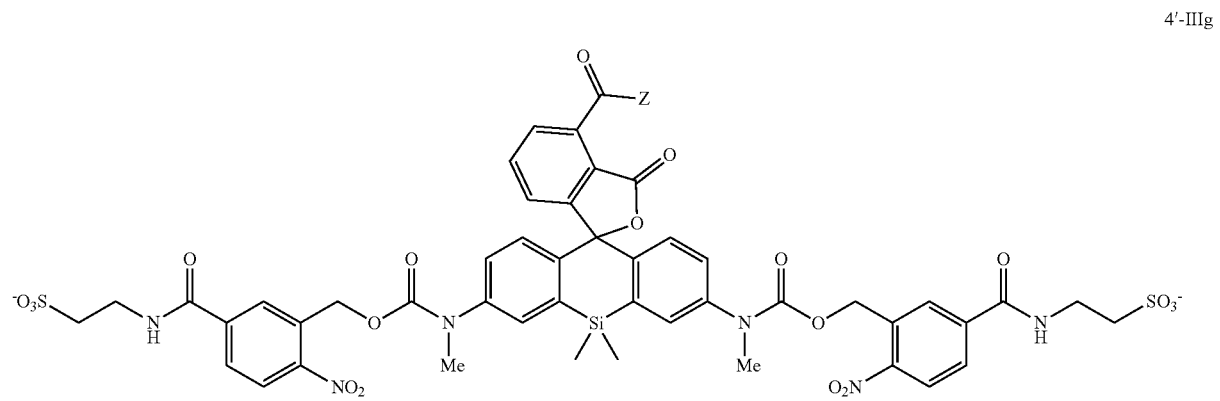
5'-IIIg
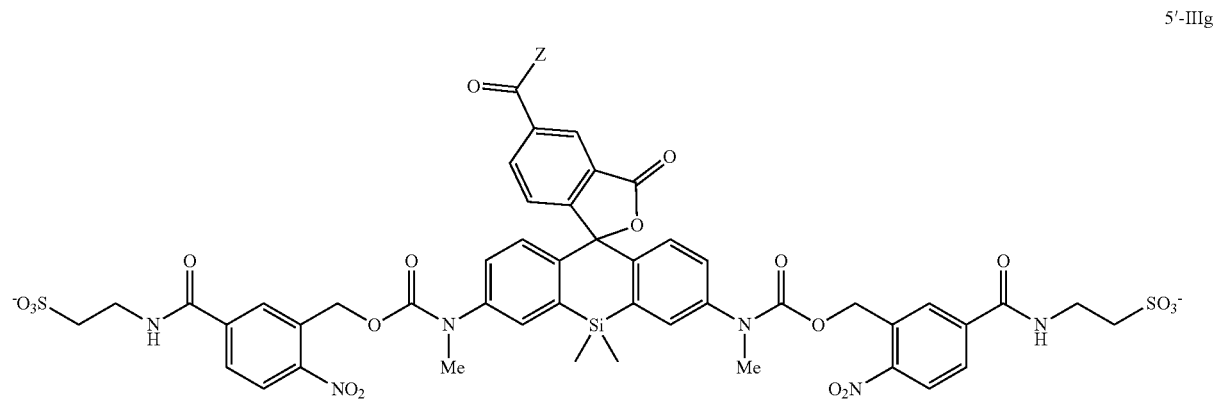

6'-IIIg
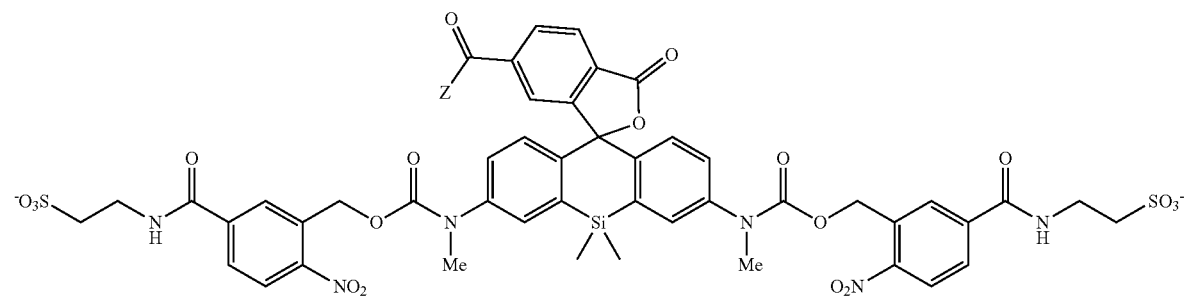
4'-IIIh
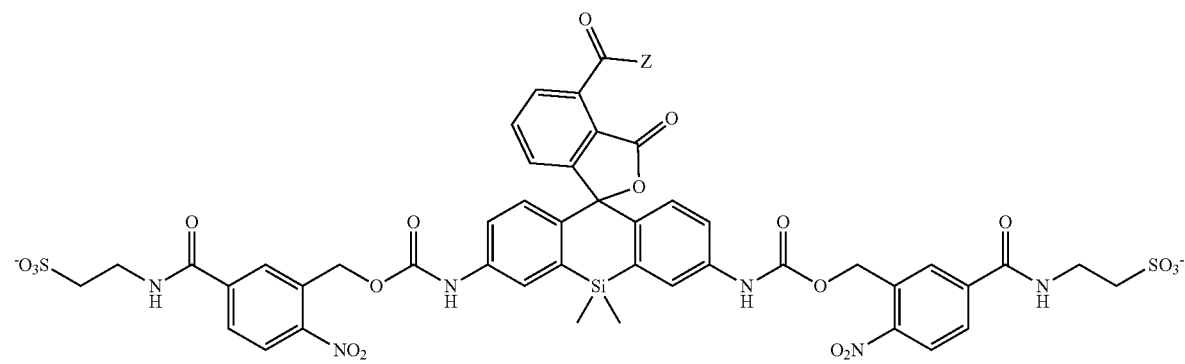
5'-IIIh
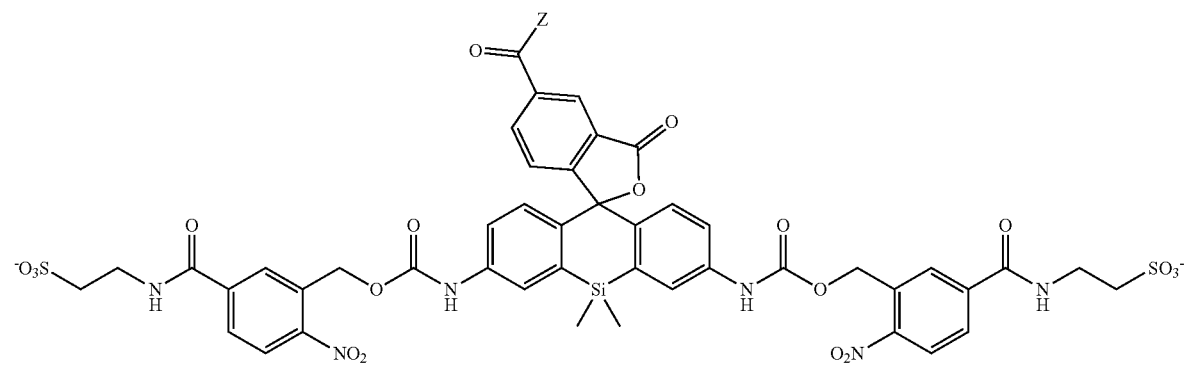
6'-IIIh
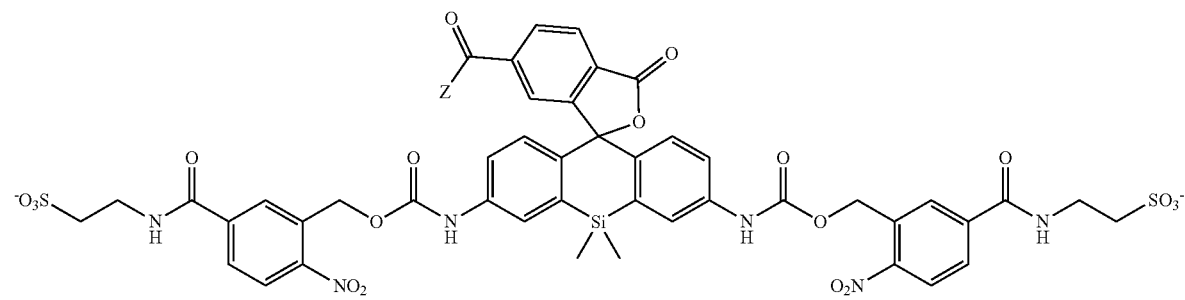

4'-IIIi
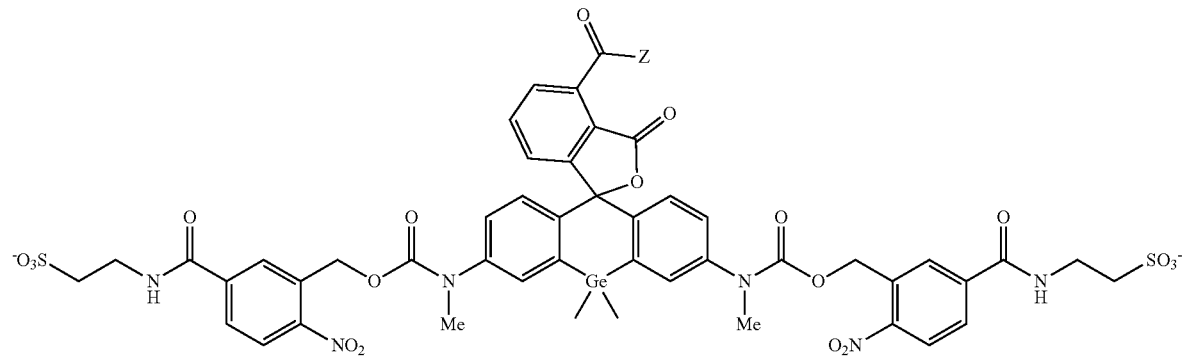
5'-IIIi
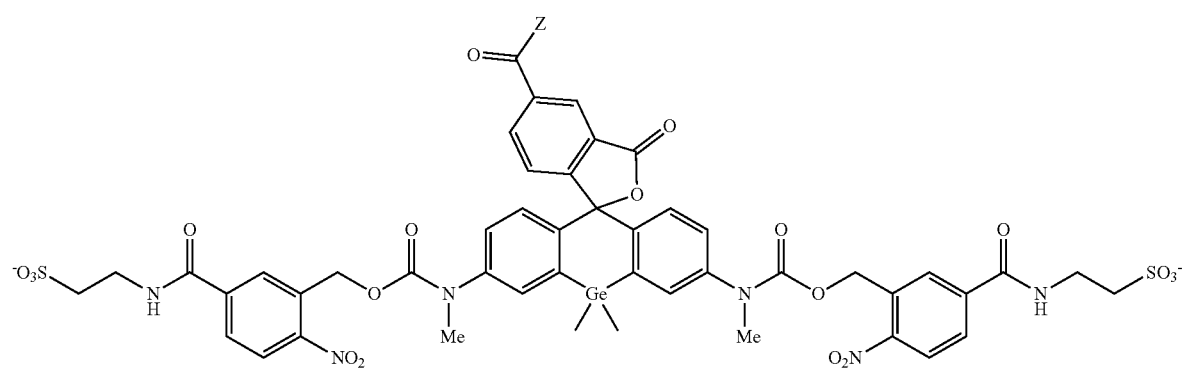
6'-IIIi
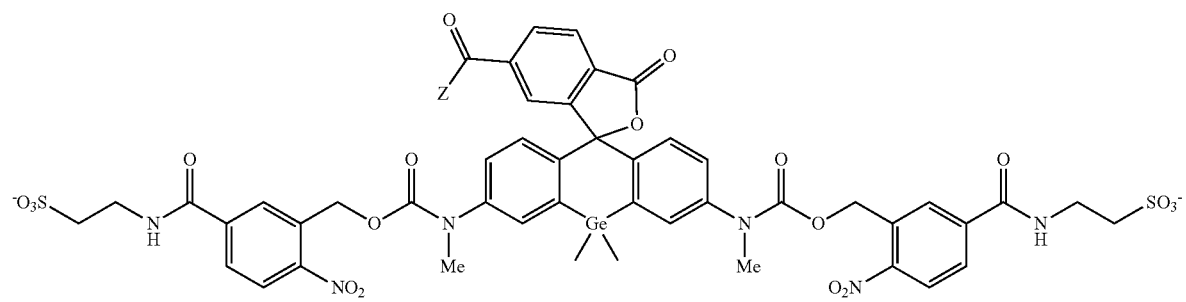
4'-IIIj
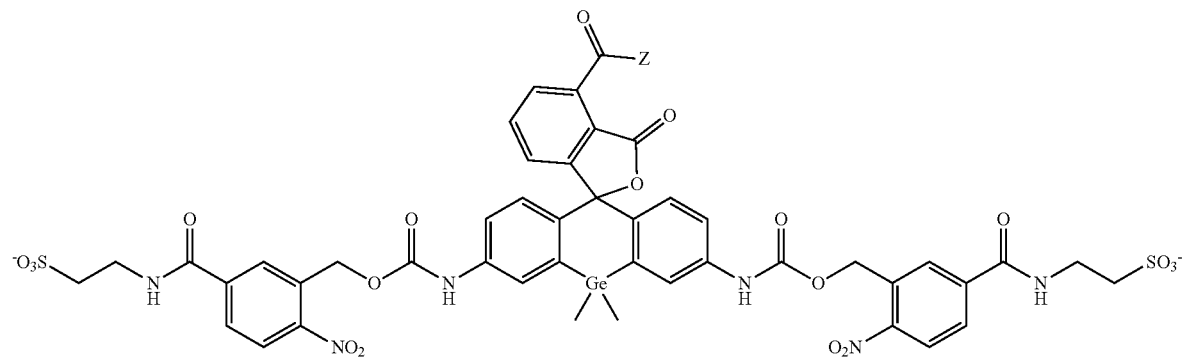

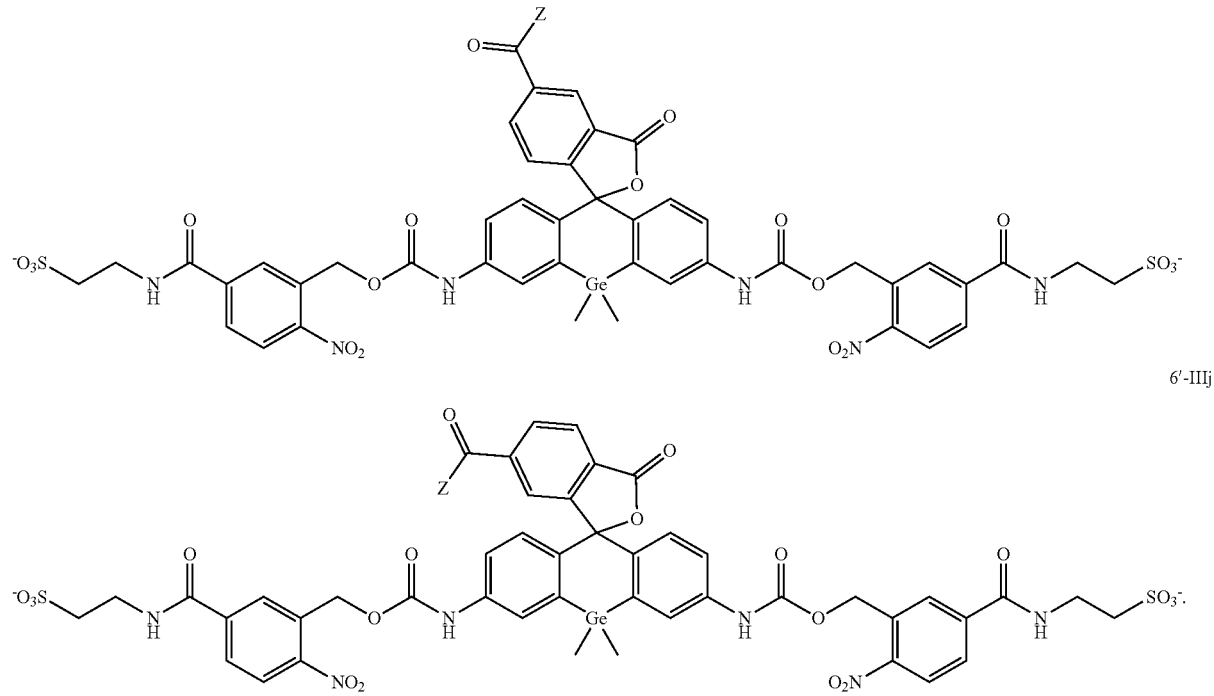

5'-IIIj

6'-IIIj

6. The compound according to claim 5, wherein:
the substituent Z represents a leaving group; or
the substituent Z represents NH-linker-CO₂H or NH-linker-CO—Z', where the substituent Z' represents a leaving group, or
the substituent Z represents O-ligand, NH-ligand or NH-linker-ligand, wherein the ligand is capable to bind covalently or non-covalently to an intra- or extracellular target entity or substance, and the ligand:
(a) comprises or represents a reactive group which is selected from an activated ester, an activated carbonate, an amine, a thiol, an azide, an alkene or alkyne, including a bicyclic and/or strained alkene or alkyne, a maleimide, and a tetrazine group;
(b) is selected from the group consisting of a HaloTag ligand, a SNAP-Tag ligand, a CLIP-Tag ligand, a TMPTag ligand and functional analogs thereof; or
(c) is selected from the group consisting of biotin, a taxoid moiety, phalloidin, and jasplakinolide.

7. The compound according to claim 6, wherein Z and/or Z' is a leaving group selected from the group consisting of azide, fluoride, N-succinimidyloxy, 3-sulfo-N-succinimidyloxy, N-phthalimidyloxy, N-tetrachlorophthalimidyloxy, pentachlorophenoxy, pentafluorophenoxy, 2,3,5,6-tetrafluorophenoxy, 4-(hydroxysulfonyl)-2,3,5,6-tetrafluorophenoxy, 1-benzotriazolyloxy, and cyanomethoxy as shown in the formulae below:

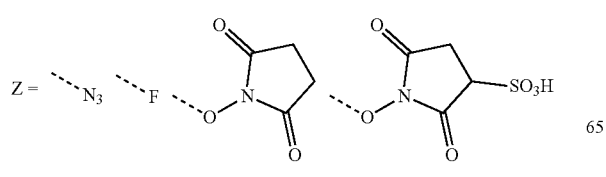

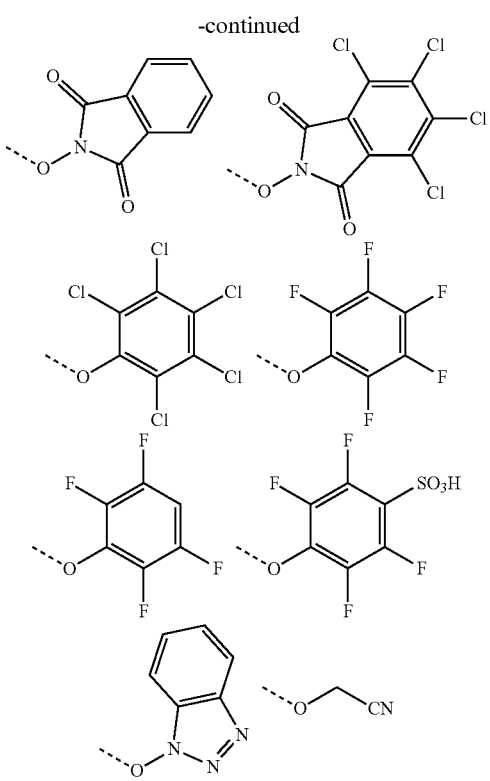

and/or wherein the linker is selected from an alkyl (polymethylene) chain —(CH₂)ₙ—, where n=an integer from 1-20, or a PEG chain having the structural formula —(CH₂CH₂O)ₙ— or —(CH₂CH₂O)ₙ₋₁—CH₂CH₂—, where n=an integer from 1-100.

8. A composition comprising one or more of the compounds of the structures IIa-IIj as defined in claim 4, or their salt forms.

9. A composition comprising one or more of the compounds of the structures 4'-IIIa-IIIj, 5'-IIIa-IIIj or 6'-IIIa-IIIj as their 3,3-, 4,4- or 5,5-isomers, as defined in claim 5, or their salt forms.

10. The compound according to claim 1 which is selected from the group of compounds 9, 13, 17, 21, 9-NHS, 13-NHS, 17-NHS, 21-NHS, 17-Halo, 21-Maleimide, 21-BG, 21-Halo and 21-Picolyl azide below:

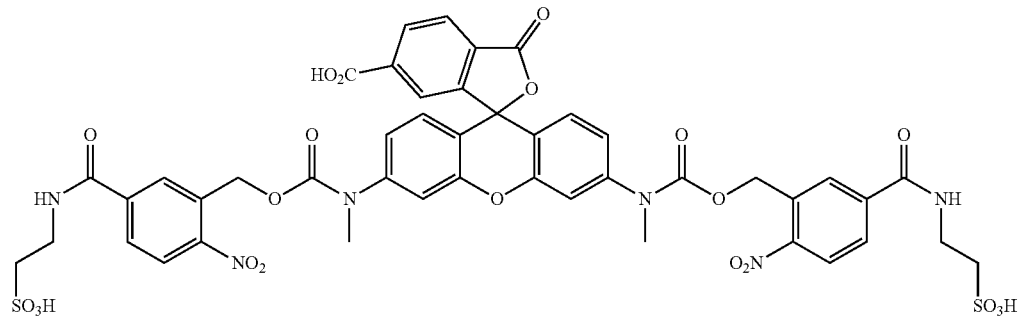

9

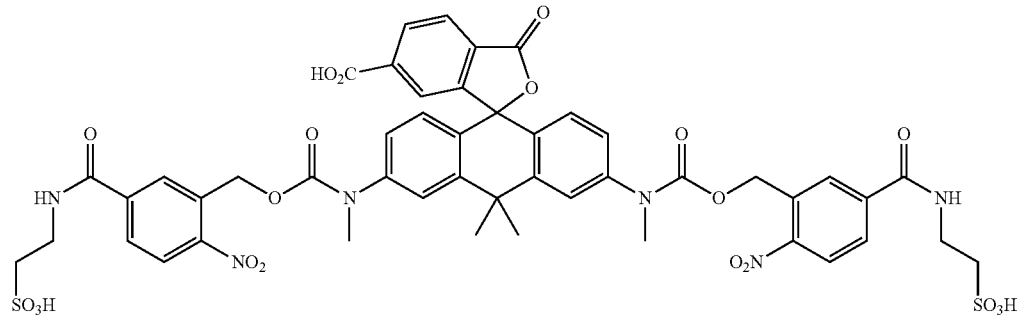

13

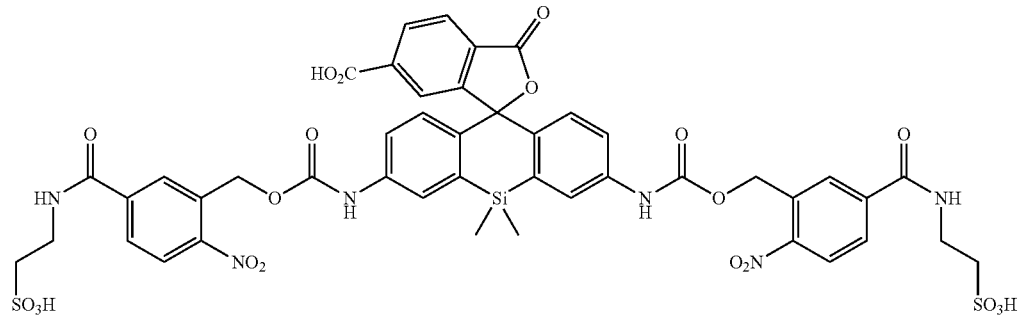

17

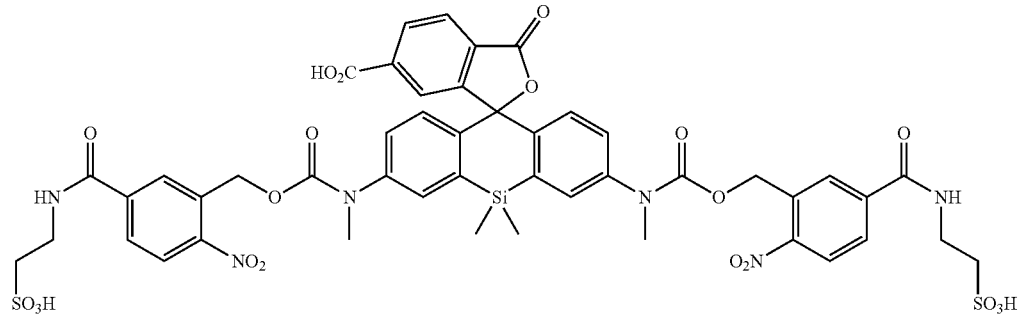

21

-continued
9-NHS
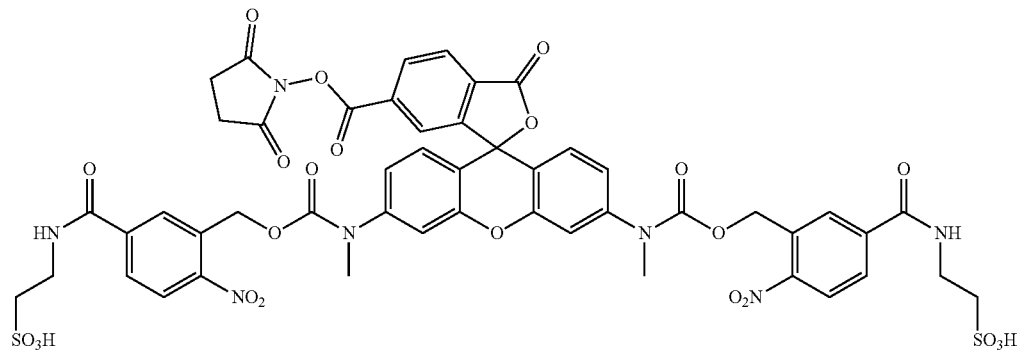
13-NHS
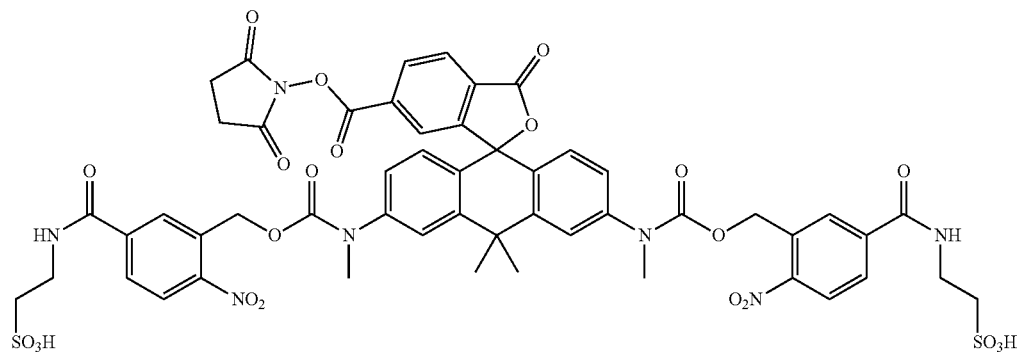
17-NHS
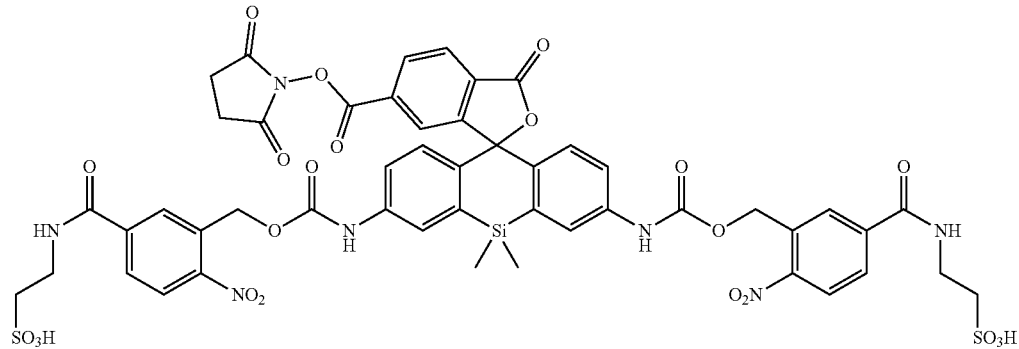
21-NHS
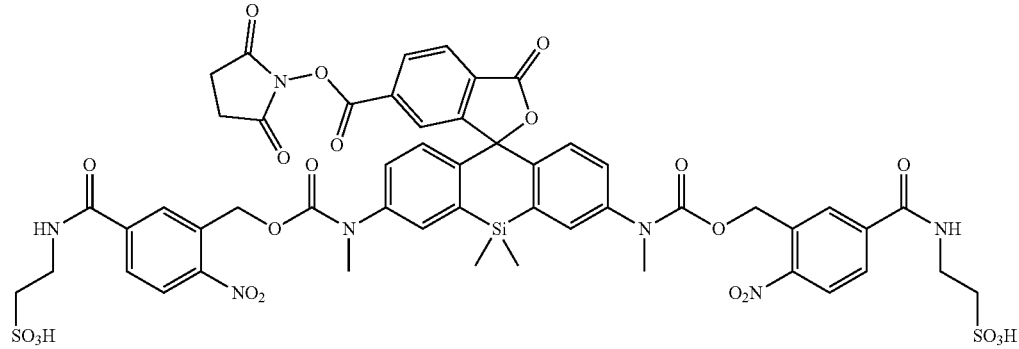

-continued
17-Halo
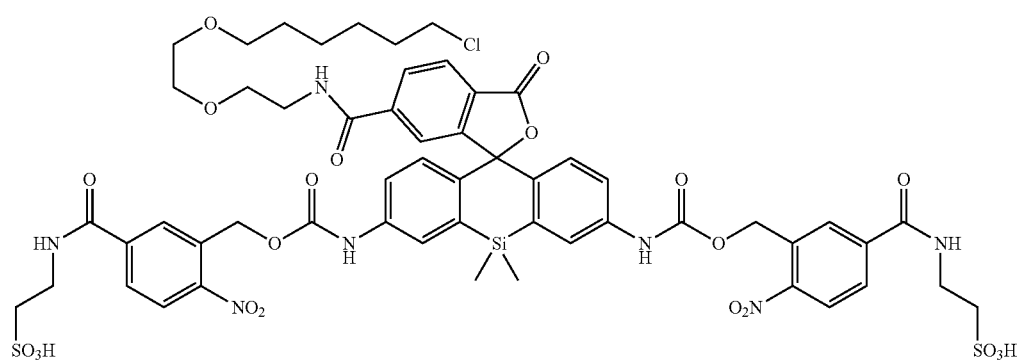
21-Maleimide
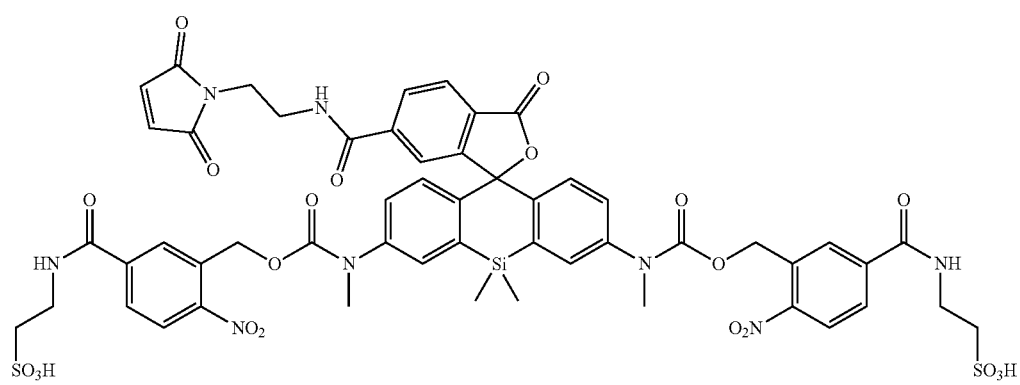
21-BG
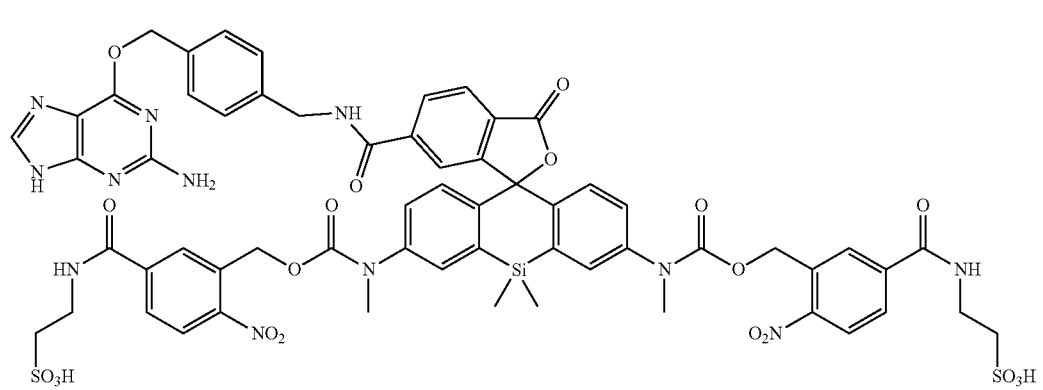
21-Halo
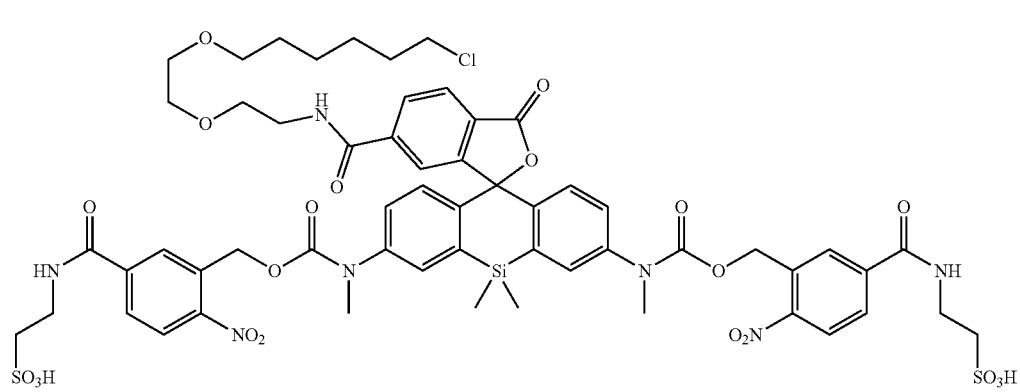

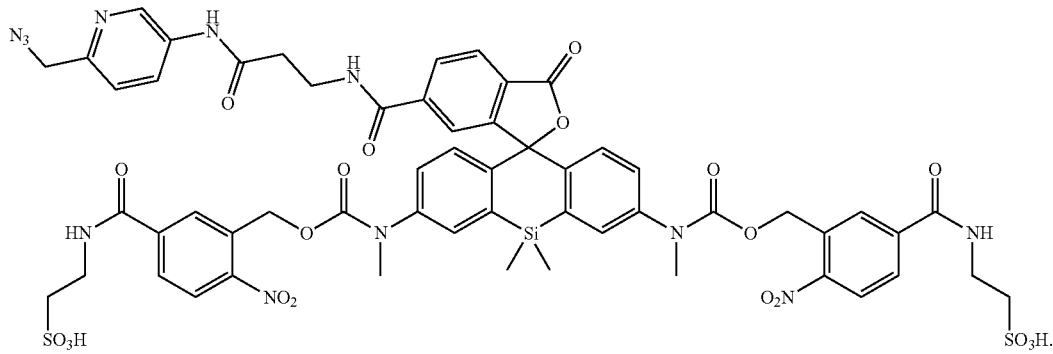

21-Picolyl azide

11. A method of providing a conjugate or a bioconjugate, said method comprising conjugating or bioconjugating a chemical entity or substance using the compound according to claim 1 or a composition thereof as a reagent for the conjugating or bioconjugating.

12. A detection method comprising detecting a target substance using the compound according to claim 1 or a composition thereof with a chemical entity or substance as a photoactivatable fluorescent dye.

13. A cell dyeing method comprising dyeing a cell using the compound according to claim 1, a composition thereof or a conjugate thereof with a chemical entity or substance in an unmasked fluorescent form as a cell membrane-permeant fluorescent dye, capable to penetrate through the membranes of fixed and living cells, or in a masked non-fluorescent form as a cell membrane-impermeant precursor for said cell membrane-permeant fluorescent dye.

14. A tracking and monitoring method comprising tracking and monitoring dynamic processes in a sample or an object, or tracking and monitoring a behavior of single molecules within a sample or an object using the compound according to claim 1, a composition thereof or a conjugate thereof with a chemical entity or substance as such or after photoactivation.

15. The tracking and monitoring method according to claim 14, further comprising detecting changes in a shape, dimensions and/or an intensity of a fluorescence signal obtained after photoactivation of the compound, composition or conjugate, which correspond to changes of the sample or object or of its environment.

16. A detection method comprising detecting a target substance using the compound according to claim 1, a composition thereof or a conjugate thereof with a chemical entity or substance as such or after photoactivation as fluorescent tags, analytical reagents and labels in optical microscopy, imaging techniques, protein tracking, nucleic acid labeling, glycan analysis, capillary electrophoresis, flow cytometry or as a component of biosensors, or as analytical tools or reporters in microfluidic devices or nanofluidic circuitry.

17. The detection method according to claim 16, wherein the compound, composition or conjugate as such or after photoactivation is used as an energy donor or an energy acceptor (reporters) in applications based on a fluorescence energy transfer (FRET) process or as energy acceptors (reporters) in applications based on a bioluminescence resonance energy transfer (BRET) process.

18. The detection method according to claim 16, wherein the optical microscopy and imaging techniques comprise single molecule switching techniques, photoactivation localization microscopy, stochastic optical reconstruction microscopy, minimal photon fluxes or their parallelized implementations, fluorescence correlation spectroscopy, fluorescence recovery after photobleaching, fluorescence lifetime imaging, ground state depletion with individual molecular return and stimulated emission depletion microscopy.

19. The detection method according to claim 18, wherein additional color multiplexing is achieved by using the compound according to claim 1, a composition thereof or a conjugate thereof as such or after photoactivation together with any other fluorescent dyes in a single sample or object under study, or wherein the controlled photoactivation of spatiotemporal subpopulations of molecules of the compound, the composition or the conjugate allows imaging with the uncaged fluorophore molecules while protecting the remaining caged fluorophores from photobleaching, or wherein the controlled photoactivation of the compound, the composition or the conjugate is achieved by a two-photon or multiphoton activation process.

20. A compound which is a photoactivable fluorescent dye having one of the following structural formulae Ia-Id:

Ia

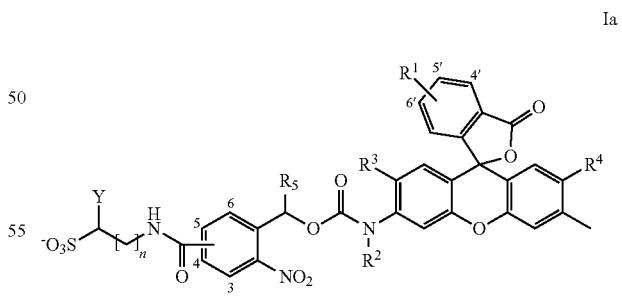

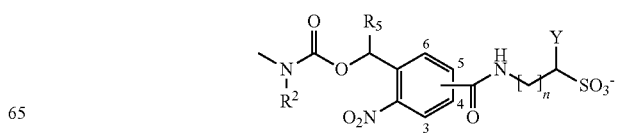

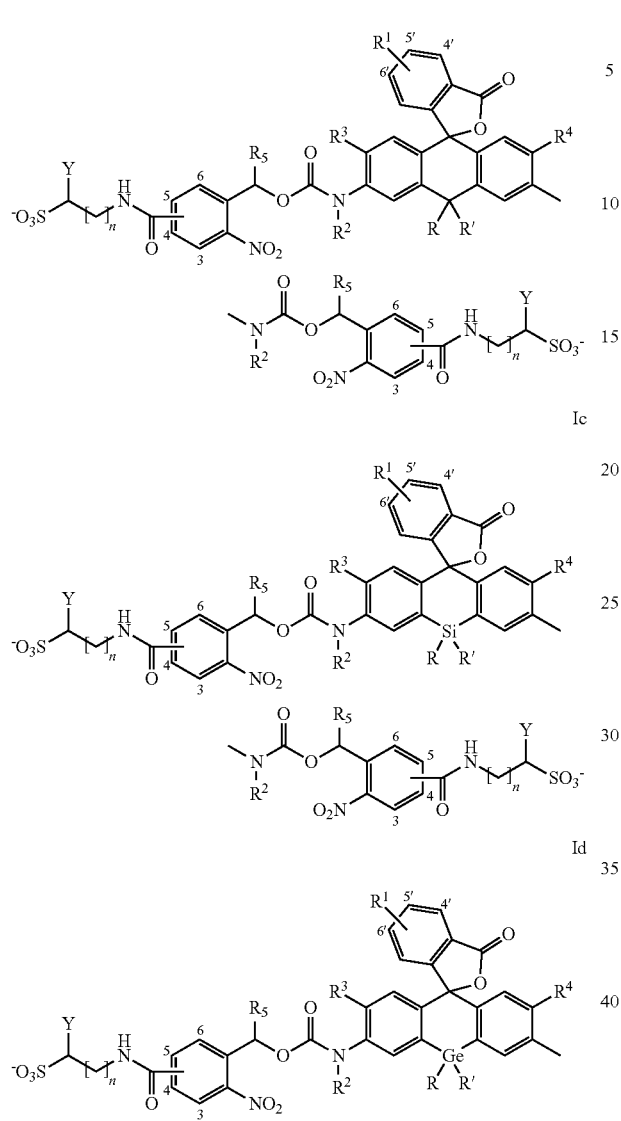

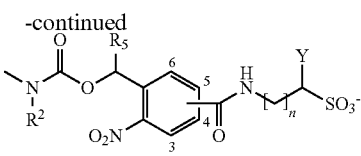

wherein:

n=0, 1, 2, 3;

Y is H, SO$_3$H or SO$_3$M, with M being a positively charged counterion;

R$^1$ is H, CO$_2$H, C(O)NH-linker-CO$_2$H, C(O)O-ligand, C(O)NH-ligand or C(O)NH-linker-ligand;

R$^2$ is H, unsubstituted alkyl, substituted alkyl, unsubstituted cycloalkyl or substituted cycloalkyl;

R$^3$ and R$^4$ are independently H or F; and

R$^5$ is H, Me, CO$_2$H, C(O)NH-linker-CO$_2$H, C(O)O-ligand, C(O)NH-ligand or C(O)NH-linker-ligand;

wherein the ligand at each occurrence represents a reactive group or tag, capable to form a covalent or non-covalent bond or molecular complex with a target chemical entity or substance;

and wherein

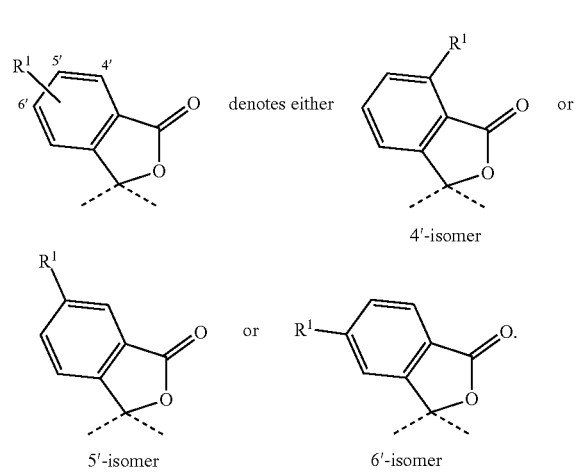

* * * * *